United States Patent
Hartung et al.

(10) Patent No.: US 8,642,611 B2
(45) Date of Patent: Feb. 4, 2014

(54) ALKYNYLPYRIMIDINES AND SALTS THEREOF, PHARMACEUTICAL COMPOSITIONS COMPRISING SAME, METHODS OF PREPARING SAME AND USES OF SAME

(75) Inventors: Ingo Hartung, Berlin (DE); Ulrich Bothe, Berlin (DE); Georg Kettschau, Berlin (DE); Ulrich Luecking, Berlin (DE); Anne Mengel, Berlin (DE); Martin Krueger, Berlin (DE); Karl Thierauch, Berlin (DE); Philip Lienau, Berlin (DE); Ulf Boemer, Glienicke/Nordbahn (DE)

(73) Assignee: Bayer Intellectual Property GmbH, Monheim (DE)

( * ) Notice: Subject to any disclaimer, the term of this patent is extended or adjusted under 35 U.S.C. 154(b) by 1077 days.

(21) Appl. No.: 12/142,279

(22) Filed: Jun. 19, 2008

(65) Prior Publication Data

US 2009/0099219 A1   Apr. 16, 2009

Related U.S. Application Data

(60) Provisional application No. 60/946,523, filed on Jun. 27, 2007.

(30) Foreign Application Priority Data

Jun. 20, 2007   (EP) .................................... 07090125

(51) Int. Cl.
| | | |
|---|---|---|
| A01N 43/54 | (2006.01) |
| A61K 31/505 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 239/02 | (2006.01) |

(52) U.S. Cl.
USPC ........................... 514/272; 544/324; 544/325

(58) Field of Classification Search
None
See application file for complete search history.

(56) References Cited

FOREIGN PATENT DOCUMENTS

| WO | WO 2005/037800 A1 | 4/2005 |
| WO | WO 2005/060969 A1 | 7/2005 |
| WO | WO 2006/082371 A1 | 8/2006 |

OTHER PUBLICATIONS

Vippagunta et. al. Advanced Drug Delivery Reviews 48 (2001) 3-26.*
Wolff et. al., "Burger's Medicinal Chemistry and Drug Discovery," 5th Ed. Part 1, pp. 975-977 (1995).*
Banker, et. al., Modern Pharmaceuticals, (1996) p. 596.*

* cited by examiner

Primary Examiner — Jeffrey Murray

(57) ABSTRACT

The invention relates to alkynylpyrimidines according to the general formula (I):

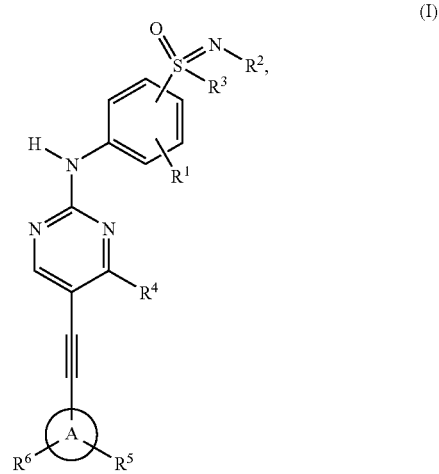

in which A, $R^1$, $R^2$, $R^3$, $R^4$, $R^5$, and $R^6$ are as defined in the claims, and salts, N-oxides, metabolites, solvates, tautomers and prodrugs thereof, to pharmaceutical compositions comprising said alkynylpyrimidines, to methods of preparing said alkynylpyrimidines, as well as to uses thereof for manufacturing a pharmaceutical composition for the treatment of diseases of dysregulated vascular growth or of diseases which are accompanied with dysregulated vascular growth, wherein the compounds effectively interfere with Tie2 and VEGFR2 signalling.

15 Claims, No Drawings

ALKYNYLPYRIMIDINES AND SALTS THEREOF, PHARMACEUTICAL COMPOSITIONS COMPRISING SAME, METHODS OF PREPARING SAME AND USES OF SAME

This application claims the benefit of the filing date of U.S. Provisional Application Ser. No. 60/946,523 filed Jun. 27, 2007.

The present invention relates to alkynylpyrimidines of general formula (I) and salts, N-oxides, metabolites, solvates and prodrugs thereof, to pharmaceutical compositions comprising said alkynylpyrimidines, to methods of preparing said alkynylpyrimidines, as well as to uses thereof.

SCIENTIFIC BACKGROUND

Dysregulated vascular growth plays a critical role in a variety of inflammatory diseases, in particular psoriasis, delayed type hypersensitivity, contact dermatitis, asthma, multiple sclerosis, restenosis, rheumatoid arthritis and inflammatory bowl disease. Aberrant vascular growth is also involved in neovascular ocular diseases such as age-related macular degeneration and diabetic retinopathy. Additionally, sustained vascular growth is accepted as one hallmark of cancer development (Hanahan, D.; Weinberg, R. A. *Cell* 2000, 100, 57). While tumors initially grow either as an avascular mass or by co-opting existing host vessels, growth beyond a few $mm^3$ in size is depending on the induction of vessel neogrowth in order to sufficiently provide the tumor with oxygen and nutrients. Induction of angiogenesis is a prerequisite that the tumor surpasses a certain size (the so called angiogenic switch). An intricate signalling interaction network between cancer cells and the tumor microenvironment triggers the induction of vessel growth from existing vasculature. The dependence of tumors on neovascularization has led to a new treatment paradigm in cancer therapy (Ferrara et al. *Nature* 2005, 438, 967; Carmeliet *Nature* 2005, 438, 932). Blocking tumor neovascularization by small molecule or antibody-mediated inhibition of relevant signal transduction pathways holds a great promise for extending currently available therapy options.

The development of the cardiovascular system involves two basic stages. In the initial vasculogenesis stage, which only occurs during embryonal development, angioblasts differentiate into endothelial cells which subsequently form a primitive vessel network. The subsequent stage, termed angiogenesis, involves the remodeling of the initial vasculature and sprouting of new vessels (Risau, W. *Nature* 1997, 386, 671; Jain, R. K. *Nat. Med.* 2003, 9, 685). Physiologically, angiogenesis occurs in wound healing, muscle growth, the female cycle and in the above mentioned disease states.

It has been found that receptor tyrosine kinases of the vascular endothelial growth factor (VEGF) family and the Tie (tyrosine kinase with immunoglobulin and epidermal growth factor homology domain) receptor tyrosine kinases are essential for both developmental and disease-associated angiogenesis (Ferrara et al *Nat. Med.* 2003, 9, 669; Dumont et al. *Genes Dev.* 1994, 8, 1897; Sato et al. *Nature* 1995, 376, 70).

In adults the Tie2 receptor tyrosine kinase is selectively expressed on endothelial cells (EC) of the adult vasculature (Schlaeger et al. *Proc. Nat. Acad. Sci. USA* 1997, 94, 3058). Immunohistochemical analysis demonstrated the expression of Tie2 in adult rat tissues undergoing angiogenesis. During ovarian folliculogenesis, Tie2 is expressed in neovessels of the developing corpus luteum. Four endogenous ligands—angiopoietins 1 to 4—have been identified for the type 1 transmembrane Tie2 (also named Tek) receptor, while no ligands have been identified so far for the Tie1 receptor. Binding of the extracellular Tie2 domain to the C-terminal fibrinogen-like domains of the various angiopoietins leads to significantly different cellular effects. In addition, heterodimerizations between Tie1 and Tie2 receptors have been postulated to influence ligand binding.

Binding of Ang1 to Tie2 expressed on EC induces receptor cross-phosphorylation and kinase activation thus triggering various intracellular signalling pathways. The intracellular C-terminal tail of the Tie2 protein plays a crucial role in Tie2 signalling (Shewchuk et al. *Structure* 2000, 8, 1105). Upon ligand binding, a conformational change is induced which removes the C-tail out of its inhibitory conformation thus allowing kinase activation by cross-phoshorylation of various Tyr residues in the C-tail, which subsequently function as docking sites for phosphotyrosine-binding (PTB) site possessing down-stream mediators. Cellular effects initiated by Ang1 activation of Tie2 include inhibition of EC apoptosis, stimulation of EC migration and blood vessel reorganization, suppression of inflammatory gene expression and suppression of vascular permeability (Brindle et al. *Circ. Res.* 2006, 98, 1014). In contrast to VEGF-VEGFR signalling in EC, Ang1 activation of Tie2 does not stimulate EC proliferation in the majority of published assay settings.

The anti-apoptotic effect of Tie2 signalling was shown to be mediated mainly by the PI3K-Akt signalling axis which is activated by binding of the regulatory p85 subunit of PI3K to Y1102 in the Tie2 C-tail (DeBusk et al. *Exp. Cell. Res.* 2004, 298, 167; Papapetropoulos et al. *J. Biol. Chem.* 2000, 275, 9102; Kim et al. *Circ. Res.* 2000, 86, 24). In contrast, the chemotactic response downstream of the activated Tie2 receptor requires crosstalk between PI3K and the adaptor protein Dok-R. Membrane localization of Dok-R via binding of its pleckstrin homology (PH) domain to PI3K and simultaneous binding to Y1108 in the Tie2 C-tail via its PTB domain leads to Dok-R phosphorylation and downstream signalling via Nck and Pak-1 (Jones et al. *Mol. Cell. Biol.* 2003, 23, 2658; Master et al. *EMBO J.* 2001, 20, 5919). PI3K-mediated recruitment of the adaptor protein ShcA to Y1102 of the Tie2 C-tail is also believed to induce cellular sprouting and motility effects involving activation of endothelial nitric oxide synthase (eNOS), focal adhesion kinase (FAK) and the GTPases RhoA and Rac1. Other downstream mediators of Tie2 signalling include the adaptor protein Grb2, which mediates Erk1/2 stimulation, and the SHP-2 phosphatase.

In conclusion, basal activation of the Tie2 pathway by Ang1 is believed to maintain quiescence and integrity of the endothelium of the adult vasculature by providing a cell survival signal for ECs and by maintaining the integrity of the EC lining of blood vessels (Peters et al. *Recent Prog. Horm. Res.* 2004, 59, 51).

In contrast to Ang1, Ang2 is not able to activate Tie2 on EC unless Ang2 is present in high concentration or for prolonged periods. However, Ang2 functions as a Tie2 agonist in non-endothelial cells transfected with Tie2. The structural basis for this context-dependence of the Ang2-Tie2 interaction is to date not understood.

In endothelial cells, however, Ang2 functions as Tie2 antagonist and thus blocks the agonistic activity of Ang1 (Maisonpierre et al. *Science* 1997, 277, 55). Ang2 binding to Tie2 prevents Ang1-mediated Tie2 activation which leads to vessel destabilization and results in vessel regression in the absence of pro-angiogenic stimuli such as VEGF. While Ang1 is widely expressed by periendothelial cells in quiescent vasculature such as pericytes or smooth muscle cells, Ang2 expression occurs in areas of ongoing angiogenesis.

Ang2 can be stored in Weibel-Palade bodies in the cytoplasm of EC allowing for a quick vascular response upon stimulation.

Ang1 and Ang2 are expressed in the corpus luteum, with Ang2 localizing to the leading edge of proliferating vessels and Ang1 localizing diffusively behind the leading edge. Ang2 expression is inter alia initiated by hypoxia (Pichiule et al. *J. Biol. Chem.* 2004, 279, 12171). Ang2 is upregulated in the tumor vasculature and represents one of the earliest tumor markers. In the hypoxic tumor tissue, Ang2 expression induces vessel permeability and—in the presence of e.g. pro-angiogenic VEGF—triggers angiogenesis. After VEGF mediated EC proliferation and vessel sprouting maturation of the newly formed vessels again necessitates Tie2 activation by Ang1. Therefore, a subtle balancing of Tie2 activity plays a pivotal role in the early as well as late stages of neovascularization. These observations render the Tie2 RTK an attractive target for anti-angiogenesis therapy in diseases caused by or associated with dysregulated vascular growth. However, it remains to be shown if targeting the Tie2 pathway alone will be sufficient to achieve efficacious blockade of neovascularization. In certain diseases or disease subtypes it might be necessary or more efficacious to block several angiogenesis-relevant signalling pathways simultaneously.

Various theories have been discussed to explain the differential effects of Ang1 and Ang2 on Tie2 downstream signalling events. Binding of Ang1 and Ang2 in a structurally different manner to the Tie2 ectodomain could induce ligand-specific conformational changes of the intracellular kinase domain explaining different cellular effects. Mutational studies however point toward similar binding sites of Ang1 and Ang2. In contrast, various publications have focussed on different oligomerization states of Ang1 vs. Ang2 as basis for different receptor multimerization states upon ligand binding. Only Ang1 present in its tetramer or higher-order structure initiates Tie2 activation in EC while Ang2 was reported to exist as a homodimer in its native state (Kim et al. *J. Biol. Chem.* 2005, 280, 20126; Davis et al. *Nat. Struc. Biol.* 2003, 10, 38; Barton et al. *Structure* 2005, 13, 825). Finally, specific interactions of Ang1 or Ang2 with additional cell-specific co-receptors could be responsible for the different cellular effects of Ang1 vs. Ang2 binding to Tie2. Interaction of Ang1 with integrin α5β1 has been reported to be essential for certain cellular effects (Carlson et al. *J. Biol. Chem.* 2001, 276, 26516; Dallabrida et al. *Circ. Res.* 2005, 96, e8). Integrin α5β1 associates constitutively with Tie2 and increases the receptor's binding affinity for Ang1 resulting in initiation of downstream signalling at lower Ang1 effector concentrations in situations where integrin α5β1 is present. The recently solved crystal structure of the Tie2-Ang2 complex suggests however that neither the oligomerization state nor a different binding mode causes the opposing cellular effects (Barton et al. *Nat. Struc. Mol. Biol.* 2006, 13, 524).

Ang1-Tie2 signalling plays also a role in the development of the lymphatic system and in lymphatic maintenance and sprouting (Tammela et al. *Blood* 2005, 105, 4642). An intimate cross-talk between Tie2 and VEGFR-3 signalling in lymphangiogenesis seems to equal the Tie2-KDR cross-talk in blood vessel angiogenesis.

A multitude of studies have underscored the functional significance of Tie2 signalling in the development and maintenance of the vasculature. Disruption of Tie2 function in Tie2$^{-/-}$ transgenic mice leads to early embryonic lethality between days 9.5 and 12.5 as a consequence of vascular abnormalities. Tie2$^{-/-}$ embryos fail to develop the normal vessel hierachy suggesting a failure of vascular branching and differentiation. The heart and vessels in Tie2$^{-/-}$ embryos show a decreased lining of EC and a loosened interaction between EC and underlying pericyte/smooth muscle cell matrix. Mice lacking functional Ang1 expression and mice overexpressing Ang2 display a phenotype reminiscent of the phenotype of Tie2$^{-/-}$ mice (Suri et al. *Cell* 1996, 87, 1171). Ang2$^{-/-}$ mice have profound defects in the growth and patterning of lymphatic vasculature and fail to remodel and regress the hyaloid vasculature of the neonatal lens (Gale et al. *Dev. Cell* 2002, 3, 411). Ang1 rescued the lymphatic defects, but not the vascular remodeling defects. Therefore, Ang2 might function as a Tie2 antagonist in blood vasculature but as a Tie2 agonist in developing lymph vasculature suggesting redundant roles of Ang1 and Ang2 in lymphatic development.

Aberrant activation of the Tie2 pathway is involved in various pathological settings. Activating Tie2 mutations leading to increased ligand-dependent and ligand-independent Tie2 kinase activity cause inherited venous malformations (Vikkula et al. *Cell* 1996, 87, 1181). Increased Ang1 mRNA and protein levels as well as increased Tie2 activation have been reported in patients with pulmonary hypertension (PH). Increased pulmonary arterial pressure in PH patients results from increased coverage of pulmonary arterioles with smooth muscle cells (Sullivan et al. *Proc. Natl. Acad. Sci. USA* 2003, 100, 12331). In chronic inflammatory diseases, like in psoriasis, Tie2 and the ligands Ang1 and Ang2 are greatly upregulated in lesions, whereas a significant decrease in expression of Tie2 and ligands occur under anti-psoriatic treatment (Kuroda et al. *J. Invest. Dermatol* 2001, 116, 713). Direct association of pathogenesis of disease with Tie2 expression has been demonstrated recently in transgenic mice overexpressing Tie2 (Voskas et al. *Am. J. Pathol.* 2005, 166, 843). In these mice overexpression of Tie2 causes a psoriasis-like phenotype (such as epidermal thickening, rete ridges and lymphocyte infiltration). These skin abnormalities are resolved completely upon suppression of transgene expression, thereby illustrating a complete dependence on Tie2 signalling for disease maintenance and progression. A recent study underscored the connection of the Ang1/Ang2-Tie2 signalling axis to the induction of inflammation (Fiedler et al. *Nat. Med.* 2006, 12, 235). Inhibition of the Tie2 signalling pathway is therefore expected to be useful in the therapy of a broad range of inflammatory diseases.

Tie2 expression was investigated in human breast cancer specimens and Tie2 expression was found in the vascular endothelium both in normal breast tissue as well as in tumor tissue. The proportion of Tie2-positive microvessels was increased in tumors as compared to normal breast tissue (Peters et al. *Br. J. Canc.* 1998, 77, 51). However, significant heterogeneity in endothelial Tie2 expression was observed in clinical specimen from a variety of human cancers (Fathers et al. *Am. J. Path.* 2005, 167, 1753). In contrast, Tie2 and angiopoietins were found to be highly expressed in the cytoplasm of human colorectal adenocarcinoma cells indicating at the potential presence of an autocrine/paracrine growth loop in certain cancers (Nakayama et al. *World J. Gastroenterol.* 2005, 11, 964). A similar autocrine/paracrine Ang1-Ang2-Tie2 loop was postulated for certain human gastric cancer cell lines (Wang et al. *Biochem. Biophys. Res. Comm.* 2005, 337, 386). In addition, it was observed clinically that Ang2 is overexpressed in the bone marrow of AML (acute myelogenous leukemia) patients and Tie2 is additionally overexpressed in leukemic blasts (Schliemann et al. 2006, 91, 1203). Taking into account that Ang1-Tie2 signalling regulates hematopoietic stem cell quiescence in the bone marrow niche, Tie2 inhibition would therefore force promyeloid cells into differentiation resulting in purging the bone marrow from leukemic precursor cells (Arai et al. *Cell* 2004, 118, 149).

The relevance of the Ang1-Tie2 signalling axis was challenged with various biochemical techniques. Inhibition of Ang1 expression by an antisense RNA approach resulted in decreased xenograft tumor growth (Shim et al. *Int. J. Canc.* 2001, 94, 6; Shim et al. *Exp. Cell Research* 2002, 279, 299). However, other studies report that experimental overexpression of Ang1 in tumor models leads to decreased tumor growth (Hayes et al. *Br. J. Canc.* 2000, 83, 1154; Hawighorst et al. *Am. J. Pathol.* 2002, 160, 1381; Stoeltzing et al. *Cancer Res.* 2003, 63, 3370). The latter results can be rationalized by the ligand's ability to stabilize the endothelial lining of vessels rendering vessels less sensitive for angiogenic stimuli. Interference with the dynamics of Ang1-Tie2 signalling either by over-stimulation or by stimulus deprivation seemingly leads to similar phenotypes.

The pharmacological relevance of inhibiting Tie2 signalling was tested applying various non-small molecule approaches. A peptidic inhibitor of Ang1/2 binding to Tie2 was shown to inhibit Ang1-induced HUVEC migration and angiogenesis induction in an in vivo model (Tournaire et al. *EMBO Rep.* 2005, 5, 1). Corneal angiogenesis induced by tumor cell conditioned medium was inhibited by a recombinant soluble Tie2 receptor (sTie2) despite the presence of VEGF (Lin et al. *J. Clin. Invest.* 1997, 100, 2072; see also Singh et al. *Biochem. Biophys. Res. Comm.* 2005, 332, 194). Gene therapy by adenoviral vector delivered sTie2 was capable of reducing tumor growth rates of a murine mammary carcinoma and a murine melanoma and resulted in reduction of metastasis formation (Lin et al. *Proc. Natl. Acad. Sci. USA* 1998, 95, 8829). Similar effects were observed with related sTie2 constructs (Siemeister et al. *Cancer Res.* 1999, 59, 3185) and a Tek-Fc construct (Fathers et al. *Am. J. Path.* 2005, 167, 1753).

Adenovirus-delivered anti-Tie2 intrabodies were shown to inhibit growth of a human Kaposi's sarcoma and a human colon carcinoma upon peritumoral administration (Popkov et al. *Cancer Res.* 2005, 65, 972). Histopathological analysis revealed a marked decrease in vessel density in treated vs. control tumors. Phenotypic simultaneous knockout of KDR and Tie2 by an adenovirus delivered intradiabody resulted in significantly higher growth inhibition of a human melanoma xenograft model than KDR knockout alone (Jendreyko et al. *Proc. Natl. Acad. Sci. USA* 2005, 102, 8293). Similarly, the bispecific Tie2-KDR intradiabody was more active in an in vitro EC tube formation inhibition assay than the two monospecific intrabodies alone (Jendreyko et al. *J. Biol. Chem.* 2003, 278, 47812). Systematic treatment of tumor-bearing mice with Ang2-blocking antibodies and peptide-Fc fusion proteins led to tumor stasis and elimination of tumor burden in a subset of animals (Oliner et al. *Cancer Cell* 2004, 6, 507). For a recent report on an immunization approach, see Luo et al. *Clin. Cancer Res.* 2006, 12, 1813.

However, from the above studies using biochemical techniques to interfere with Tie2 signalling it is not clear, whether similar phenotypes will be observed with small molecule inhibitors of the Tie2 kinase activity. Small molecule inhibitors of kinases by definition block only those cellular effects which are mediated by the receptor's kinase activity and not those which might involve the kinase only as a co-receptor or scaffolding component in multi-enzyme complexes. So far, studies describing in vivo pharmacodynamic effects of small molecule Tie2 inhibitors are rare (Scharpfenecker et al. *J. Cell Sci.* 2005, 118, 771; J. M. Chen, *Medicinal Chemistry and High Speed Synthesis—The Tie-2 story*; presentation held at the centennial AACR meeting, April 2007, Los Angeles, U.S.A). It remains to be shown that small molecule inhibitors of the Tie2 kinase will be as efficacious in inhibiting angiogenesis as e.g. ligand antibodies, soluble decoy receptors or receptor intrabodies.

PRIOR ART

To date, a small number of therapeutic agents with antiangiogenic activity have been approved for cancer treatment. Avastin (Bevacizumab), a VEGF neutralizing antibody, blocks KDR and VEGFR1 signalling and has been approved for first-line treatment of metastatic colorectal cancer. The small molecule multi-targeted kinase inhibitor Nexavar® (Sorafenib) inhibits inter alia members of the VEGFR family and has been approved for the treatment of advanced renal cell carcinoma. Sutent (Sunitinib), another multi-targeted kinase inhibitor with activity vs. VEGFR family members, has been approved by the FDA for treatment of patients with gastrointestinal stromal tumors (GIST) or advanced kidney tumors. Several other small molecule inhibitors of angiogenesis-relevant targets are in clinical and pre-clinical development.

AMG-386, an angiopoietin-targeting recombinant Fc fusion protein, and CE-245677, a small molecular TrkA-Tie2 inhibitor, are in phase I clinical development in patients with solid tumors. Several multi-targeted small molecule inhibitors with activity against Tie2 are (or have been) in preclinical evaluation for cancer therapy, including ABT-869, GW697465A and A-422885.88 (BSF466895).

The diaminopyrimidine core has been used frequently as a template for kinase inhibitors. Diaminopyrimidine-derived compounds have been described as inter alia inhibitors of cyclin-dependent kinases (for example in WO2002096888), of Aurora kinases (WO 2003032997, WO2007003596), of Syk kinase (WO 2003063794), of ZAP-70 kinase (WO 2003078404), of Plk kinase (WO2004074244), of KDR kinase (WO 2003074515), of Lck kinase (WO 2006044823) of PKC theta kinase (US 20060025433) and of Tie2 kinase (WO 2006108695; WO 2006044823; WO 2006103449; WO 2006082373; WO 2006082404) for use in a broad set of pathological conditions. In *Exp. Opin. Ther. Targets* 2005, 9, 975, by Klebl and Mueller, mention is made of a general feature of privileged kinase inhibitor scaffolds: <<Selected derivatives of an identical chemical core structure frequently recognize distinct kinases with different associated therapeutic relevance. This has been shown with the imatinib-like aminopyrimidines, in which the addition of a single methyl group to the aminopyrimidine core led to an unexpected change in selectivity from PKC to Abl. It has become clear that the specificity and selectivity for a target is a function of the derivatization pattern of an underlying core structure.>>

However, potent inhibition of anti-proliferative kinase targets such as, for example, cyclin-dependent kinases, Aurora kinases, Chk1 kinase or Plk1 kinase would limit the use of such a compound as a purely anti-angiogenic drug. The activity against non-angiogenic targets would be expected to increase the risk of dose-limiting toxicities. Compounds with purely anti-angiogenic activity (<<spectrum-selective kinase inhibitors >>) and therefore with low systemic toxicity hold the promise to be applicable in a continuous dosing regime. Such a profile would be highly advantageous to treat diseases of dysregulated vascular growth or diseases which are accompanied with dysregulated vascular growth, in particular solid tumors and metastases thereof, but also for treating non-oncological diseases of dysregulated vascular growth or non-oncological diseases which are accompanied with dysregulated vascular growth, such as, for example, retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel, and diseases such as coronary and peripheral artery disease.

TECHNICAL PROBLEM TO BE SOLVED

There is a great need for small molecule inhibitors of the Tie2 kinase, in particular inhibitors not only of the isolated kinase domain, but more importantly of cellular Tie-2 autophosphorylation. Additive anti-angiogenic activities such as inhibition of, for example, KDR, and tunability of ADMET ("Adsorption, Distribution, Metabolism, Excretion, Toxicity") controlling parameters such as, for example, solubility, membrane permeability, plasma protein binding, tissue distribution, metabolism kinetics, Cyp interaction and/or hERG inhibition will finally allow for choosing compounds of suitable profiles for various diseases caused by or associated with dysregulated vascular growth. Facilitating synthetic accessibility while maintaining potency compared to prior art compounds of a related chemotype would also be of great benefit hence lowering cost of goods for providing potent compounds.

It would be desirable to have compounds at one's disposal which display selectivity within the class of protein kinases since inhibition of a broad spectrum of kinases and side effects resulting thereof would limit pharmaceutical applications of those compounds (see above). It would be especially desirable to have compounds at one's disposal which display potent inhibition of Tie2 and additional angiogenesis-controlling kinases, such as, for example, KDR, while being significantly less active as inhibitors of other kinases, which control the proliferation of non-endothelial cells, such as, for example, cyclin-dependent kinases, Aurora kinases, Chk1, and/or Plk1.

DESCRIPTION OF THE INVENTION

Surprisingly, it was found that compounds of the present invention display potent activity as inhibitors of Tie2 kinase activity and as inhibitors of cellular Tie2 autophosphorylation with a strikingly favourable selectivity profile in favour of inhibiting angiogenesis-controlling kinases while being significantly less active or even inactive against kinases which modulate the cell cycle of proliferating cells. More particularly, compounds of the present invention are potent inhibitors of Tie2 kinase and further angiogenesis-controlling kinases, such as, for example, KDR kinase, while being significantly less active or not active against CDK2, Aurora kinases, and Chk1 kinase. This is even more surprising as prior art compounds from the same chemotype are reported to be primarily active against CDK2 (see for example WO 2005037800), Aurora A and Aurora B kinase (see for example WO2007003596). Preferred compounds of the present invention are potent inhibitors of cellular Tie2 phosphorylation and VEGF-stimulated endothelial cell proliferation while being less or not active against CDK2, Aurora kinases and Chk1. Such a pharmacological profile is highly desirable not only for treating diseases of dysregulated vascular growth or diseases which are accompanied with dysregulated vascular growth, in particular solid tumors and metastases thereof, but also for treating non-oncological diseases of dysregulated vascular growth or non-oncological diseases which are accompanied with dysregulated vascular growth, such as, for example, retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel, and diseases such as coronary and peripheral artery disease, The solution to the above-mentioned novel technical problem is achieved by providing compounds derived, in accordance with the present invention, from a class of alkynylpyrimidines and salts, N-oxides, metabolites, solvates, tautomers and prodrugs thereof, methods of preparing alkynylpyrimidines, a pharmaceutical composition containing said alkynylpyrimidines, use of said alkynylpyrimidines and a method for treating diseases with said alkynylpyrimidines, all in accordance with the description, as defined in the claims of the present application.

The compounds of formula (I) below, salts, N-oxides, metabolites, solvates, tautomers and prodrugs thereof are collectively referred to as "the compounds of the present invention". The invention thus relates to compounds of general formula (I):

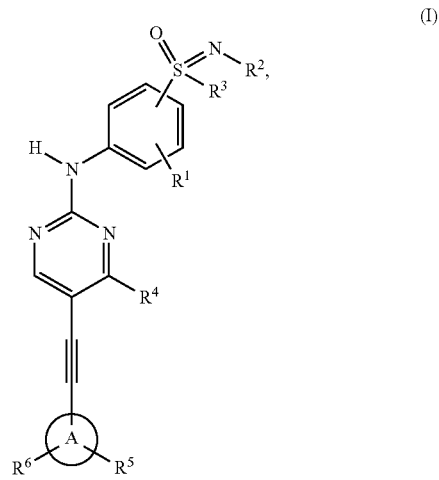

in which:

$R^1$ is selected from the group comprising, preferably consisting of, hydrogen, halogen, nitro, cyano, —$C_1$-$C_6$-alkyl, —$C_1$-$C_6$-alkylthio, —$C_1$-$C_6$-haloalkyl, $C_3$-$C_{10}$-cycloalkyl, —$(CH_2)_mOR^c$, —$(CH_2)_mNR^{d1}R^{d2}$, and —$(CH_2)_mC(O)R^b$;

$R^2$ represents hydrogen, —$C(O)R^b$, —$S(O)_2R^b$, —$P(O)(OR^f)_2$, or —$S(O)_2$—$(CH_2)_2$—$Si(R^hR^kR^j)$, or is selected from the group comprising, preferably consisting of —$C_1$-$C_6$-alkyl, —$C_2$-$C_6$-alkenyl, —$C_2$-$C_6$-alkynyl, —$C_3$-$C_{10}$-cycloalkyl, aryl, heteroaryl and —$C_3$-$C_{10}$-heterocycloalkyl, wherein said residues are unsubstituted or substituted one or more times independently from each other with halogen, nitro, cyano, —$C_1$-$C_6$-alkyl, aryl, heteroaryl, —$OR^c$, —$NR^{d1}R^{d2}$, —$C_1$-$C_6$-haloalkyl, —$C(O)R^b$, or —$S(O)_2R^b$;

$R^3$ is selected from the group comprising, preferably consisting of —$C_1$-$C_6$-alkyl, —$C_2$-$C_6$-alkenyl, —$C_2$-$C_6$-alkynyl, aryl, heteraryl and —$C_3$-$C_{10}$-cycloalkyl, wherein said residues are unsubstituted or substituted one or more times independently from each other with halogen, nitro, cyano, —$C_1$-$C_6$-alkyl, aryl, heteraryl, —$OR^c$, —$NR^{d1}R^{d2}$, —$C_1$-$C_6$-haloalkyl, —$C(O)R^b$, or —$S(O)_2R^b$;

$R^4$ is selected from the group comprising, preferably consisting of, hydrogen, —$OR^7$, —$SR^7$ and —$NR^7R^8$;

$R^5$ is selected from the group comprising, preferably consisting of, hydrogen, halogen, nitro, cyano, —$C_1$-$C_6$-alkyl, —$C_3$-$C_{10}$-cycloalkyl, —$C_1$-$C_6$-haloalkyl, —$C_1$-$C_6$-alkylthio, —$(CH_2)_nOR^f$, —$(CH_2)_nNR^sC(O)R^m$, —$(CH_2)_nNR^sS(O)_2R^m$, —$(CH_2)_nNR^{g1}R^{g2}$, —$(CH_2)_nC(O)R^n$, and —$(CH_2)_nS(O)_2R^n$;

$R^6$ is selected from the group comprising, preferably consisting of, hydrogen, halogen, nitro, cyano, hydroxyl, —$C_1$-$C_6$-alkyl, —$C_3$-$C_{10}$-cycloalkyl, —$C_1$-$C_6$-haloalkyl, —$C_1$-$C_6$-haloalkoxy, —$C_1$-$C_6$-alkoxy, and —$C_1$-$C_6$-alkylthio;

$R^7$, $R^8$ independently from each other are selected from the group comprising, preferably consisting of hydrogen, —$C_1$-$C_6$-alkyl, —$C_2$-$C_6$-alkenyl, —$C_2$-$C_6$-alkynyl, —$C_3$-$C_{10}$-cycloalkyl, —$(CH_2)_p$-aryl, —$(CH_2)_p$-heteroaryl and —$C_3$-$C_{10}$-heterocycloalkyl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, aryl, heteroaryl, —$OR^c$, —$NR^{d1}R^{d2}$, —$C_1$-$C_6$-haloalkyl, —$C(O)R^b$, or —$S(O)_2R^b$; or $R^7$, $R^8$ in the context of a $NR^7R^8$ group together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —$C(O)$—, —$S(O)$—, and/or —$S(O)_2$— group, and can optionally contain one or more double bonds;

$R^a$ is selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^b$ is selected from the group comprising, preferably consisting of, —$OR^c$, —$SR^c$, —$NR^{d1}R^{d2}$, aryl, heteroaryl, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, —$NR^{g1}R^{g2}$ or $C_1$-$C_6$-alkoxy;

$R^c$ is selected from the group comprising, preferably consisting of, hydrogen, —$C(O)R^e$, —$S(O)_2R^e$, —$P(O)(OR^f)_2$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —$OR^f$, —$NR^{d1}R^{d2}$, or —$OP(O)(OR^f)_2$ $R^{d1}$, $R^{d2}$ independently from each other are selected from the group comprising, preferably consisting of, hydrogen, $C_1$-$C_6$-alkyl, $C_3$-$C_{10}$-cycloalkyl, $C_3$-$C_{10}$-heterocycloalkyl, aryl, and heteroaryl, or for a group —$C(O)R^e$ or —$S(O)_2R^e$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$C_1$-$C_6$-alkyl, —$NR^{g1}R^{g2}$, —$OR^f$, —$C(O)R^e$, —$S(O)_2R^e$, or —$OP(O)(OR^f)_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —$C(O)$—, —$S(O)$—, and/or —$S(O)_2$— group, and can optionally contain one or more double bonds;

$R^e$ is selected from the group comprising, preferably consisting of, —$NR^{g1}R^{g2}$, $C_2$-$C_6$-alkyl, $C_3$-$C_6$-cycloalkyl, $C_1$-$C_6$-alkoxy, aryl and heteroaryl;

$R^f$ is selected from the group comprising, preferably consisting of, hydrogen, —$C(O)R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —$C(O)$—, —$S(O)$—, and/or —$S(O)_2$— group, and can optionally contain one or more double bonds;

$R^h$, $R^k$, and $R^i$ independently from each other represent —$C_1$-$C_6$-alkyl or phenyl;

$R^m$ is selected from the group comprising, preferably consisting of, $C_1$-$C_6$-alkyl, $C_3$-$C_{10}$-cycloalkyl and $C_3$-$C_{10}$-heterocycloalkyl;

$R^n$ is selected from the group comprising, preferably consisting of, —$NR^{g1}R^{g2}$, $C_1$-$C_6$-alkyl, $C_3$-$C_6$-cycloalkyl, hydroxyl and $C_1$-$C_6$-alkoxy;

$R^s$ represents hydrogen or $C_1$-$C_6$-alkyl

A represents aryl or heteroaryl;

m represent an integer of 0, 1 or 2;

n represent an integer of 0, 1 or 2;

p represent an integer of 0, 1 or 2;

wherein, when one or more of $R^a$, $R^b$, $R^c$, $R^{d1}$, $R^{d2}$, $R^e$, $R^f$, $R^{g1}$ or $R^{g2}$ is (are) present in one position in the molecule as well as in one or more further positions in the molecule, said $R^a$, $R^b$, $R^c$, $R^{d1}$, $R^{d2}$, $R^e$, $R^f$, $R^{g1}$ or $R^{g2}$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^e$, $R^f$, $R^{g1}$ or $R^{g2}$ within a single molecule to be identical or different. For example, when $OR^c$ is present twice in the molecule, then the meaning of the first $OR^c$ may be O—$C_1$-$C_6$-alkyl, for example, and the meaning of the second $OR^c$ may be O—$C(O)$—$C_3$-$C_{10}$-cycloalkyl, for example.

In accordance with a preferred embodiment, the present invention relates to compounds of general formula (I), in which:

$R^1$ represents hydrogen;

$R^2$ represents hydrogen, —C(O)$R^b$, —S(O)$_2R^b$, —P(O)(O$R^f$)$_2$, or —S(O)$_2$—(CH$_2$)$_2$—Si($R^h R^k R^l$), or is selected from the group comprising, preferably consisting of —C$_1$-C$_6$-alkyl, —C$_2$-C$_6$-alkenyl, —C$_2$-C$_6$-alkynyl, —C$_3$-C$_{10}$-cycloalkyl, aryl, heteroaryl and —C$_3$-C$_{10}$-heterocycloalkyl, wherein said residues are unsubstituted or substituted one or more times independently from each other with halogen, nitro, cyano, —C$_1$-C$_6$-alkyl, aryl, heteroaryl, —O$R^c$, —N$R^{d1}R^{d2}$, —C$_1$-C$_6$-haloalkyl, —C(O)$R^b$, or —S(O)$_2R^b$;

$R^3$ is selected from the group comprising, preferably consisting of —C$_1$-C$_6$-alkyl, —C$_2$-C$_6$-alkenyl, —C$_2$-C$_6$-alkynyl, aryl, hetaryl and —C$_3$-C$_{10}$-cycloalkyl, wherein said residues are unsubstituted or substituted one or more times independently from each other with halogen, nitro, cyano, —C$_1$-C$_6$-alkyl, aryl, hetaryl, —O$R^c$, —N$R^{d1}R^{d2}$, —C$_1$-C$_6$-haloalkyl, —C(O)$R^b$, or —S(O)$_2R^b$;

$R^4$ is selected from the group comprising, preferably consisting of, hydrogen, —O$R^7$, —S$R^7$ and —N$R^7R^8$;

$R^5$ is selected from the group comprising, preferably consisting of, hydrogen, halogen, nitro, cyano, —C$_1$-C$_6$-alkyl, —C$_3$-C$_{10}$-cycloalkyl, —C$_1$-C$_6$-haloalkyl, —C$_1$-C$_6$-alkylthio, —(CH$_2$)$_n$O$R^f$, —(CH$_2$)$_n$N$R^s$C(O)$R^m$, —(CH$_2$)$_n$N$R^s$S(O)$_2R^m$, —(CH$_2$)$_n$N$R^{g1}R^{g2}$, —(CH$_2$)$_n$C(O)$R^n$, and —(CH$_2$)$_n$S(O)$_2R^n$;

$R^6$ is selected from the group comprising, preferably consisting of, hydrogen, halogen, nitro, cyano, hydroxyl, —C$_1$-C$_6$-alkyl, —C$_3$-C$_{10}$-cycloalkyl, —C$_1$-C$_6$-haloalkyl, —C$_1$-C$_6$-haloalkoxy, —C$_1$-C$_6$-alkoxy, and —C$_1$-C$_6$-alkylthio;

$R^7$, $R^8$ independently from each other are selected from the group comprising, preferably consisting of, hydrogen, —C$_1$-C$_6$-alkyl, —C$_2$-C$_6$-alkenyl, —C$_2$-C$_6$-alkynyl, —C$_3$-C$_{10}$-cycloalkyl, —(CH$_2$)$_p$-aryl, —(CH$_2$)$_p$-heteroaryl and —C$_3$-C$_{10}$-heterocycloalkyl, wherein said residues are unsubstituted or substituted one or more times independently from each other with halogen, nitro, cyano, —C$_1$-C$_6$-alkyl, —C$_3$-C$_{10}$-cycloalkyl, —C$_3$-C$_{10}$-heterocycloalkyl, aryl, heteroaryl, —O$R^c$, —N$R^{d1}R^{d2}$, —C$_1$-C$_6$-haloalkyl, —C(O)$R^b$, or —S(O)$_2R^b$; or $R^7$, $R^8$ in the context of a N$R^7R^8$ group together with the nitrogen atom to which they are attached, form a 3 to 10 membered heterocycloalkyl ring, which is optionally substituted one or more times, the same way or differently, with C$_1$-C$_6$-alkyl, —N$R^{g1}R^{g2}$, —O$R^f$, —C(O)$R^e$, —S(O)$_2R^e$, or —OP(O)(O$R^f$)$_2$; whereby the carbon backbone of this heterocycloalkyl ring can optionally be interrupted one or more times, the same way or differently, by a member of the group comprising, preferably consisting of, NH, N$R^a$, oxygen or sulphur, and can optionally be interrupted one or more times, the same way or differently, with a —C(O)—, —S(O)—, and/or —S(O)$_2$— group, and can optionally contain one or more double bonds;

$R^a$ is selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl, wherein C$_1$-C$_6$-alkyl, and C$_3$-C$_{10}$-cycloalkyl are optionally substituted one or more times with hydroxyl, halogen, or C$_1$-C$_6$-alkoxy;

$R^b$ is selected from the group comprising, preferably consisting of, —O$R^c$, —S$R^c$, —N$R^{d1}R^{d2}$, aryl, heteroaryl, C$_1$-C$_6$-alkyl, and C$_3$-C$_{10}$-cycloalkyl, wherein C$_1$-C$_6$-alkyl, and C$_3$-C$_{10}$-cycloalkyl are optionally substituted one or more times with hydroxyl, halogen, —N$R^{g1}R^{g2}$ or C$_1$-C$_6$-alkoxy;

$R^c$ is selected from the group comprising, preferably consisting of, hydrogen, —C(O)$R^e$, —S(O)$_2R^e$, —P(O)(O$R^f$)$_2$, C$_1$-C$_6$-alkyl, C$_1$-C$_6$-haloalkyl C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with halogen, aryl, —O$R^f$, —N$R^{d1}R^{d2}$, or —OP(O)(O$R^f$)$_2$;

$R^{d1}R^{d2}$ independently from each other are selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl, or for a group —C(O)$R^e$ or —S(O)$_2R^e$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —C$_1$-C$_6$-alkyl, —N$R^{g1}R^{g2}$, —O$R^f$, —C(O)$R^e$, —S(O)$_2R^e$, or —OP(O)(O$R^f$)$_2$; or $R^{d1}$ and $R^{d2}$ together with the nitrogen atom to which they are attached, form a 3 to 10 membered heterocycloalkyl ring, which is optionally substituted one or more times, the same way or differently, with C$_1$-C$_6$-alkyl, —N$R^{g1}R^{g2}$, —O$R^f$, C(O)$R^e$, —S(O)$_2R^e$, or —OP(O)(O$R^f$)$_2$; whereby the carbon backbone of this heterocycloalkyl ring can optionally be interrupted one or more times, the same way or differently, by a member of the group comprising, preferably consisting of, NH, N$R^a$, oxygen or sulphur, and can optionally be interrupted one or more times, the same way or differently, with a —C(O)—, —S(O)—, and/or —S(O)$_2$— group, and can optionally contain one or more double bonds;

$R^e$ is selected from the group comprising, preferably consisting of, —N$R^{g1}R^{g2}$, C$_1$-C$_6$-alkyl, C$_3$-C$_6$-cycloalkyl, C$_1$-C$_6$-alkoxy, aryl and heteroaryl;

$R^f$ is selected from the group comprising, preferably consisting of, hydrogen, —C(O)$R^e$, C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, C$_1$-C$_6$-alkoxy, aryl, or —N$R^{g1}R^{g2}$;

$R^{g1}$, $R^{g2}$ independently from each other are selected from the group comprising, preferably consisting of, hydrogen, C$_1$-C$_6$-alkyl, C$_3$-C$_{10}$-cycloalkyl, C$_3$-C$_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with C$_1$-C$_6$-alkyl, —C$_1$-C$_6$-alkoxy, or hydroxy; whereby the carbon backbone of this heterocycloalkyl ring can optionally be interrupted one or more times, the same way or differently, by a member of the group comprising, preferably consisting of, NH, N$R^a$, oxygen or sulphur, and can optionally be interrupted one or more times, the same way or differently, with a —C(O)—, —S(O)—, and/or —S(O)$_2$— group, and can optionally contain one or more double bonds;

$R^h$, $R^k$, and $R^l$ independently from each other represent —C$_1$-C$_6$-alkyl or phenyl;

$R^m$ is selected from the group comprising, preferably consisting of, C$_1$-C$_6$-alkyl, C$_3$-C$_{10}$-cycloalkyl and C$_3$-C$_{10}$-heterocycloalkyl;

$R^n$ is selected from the group comprising, preferably consisting of, —N$R^{g1}R^{g2}$, C$_1$-C$_6$-alkyl, C$_3$-C$_6$-cycloalkyl, hydroxyl and C$_1$-C$_6$-alkoxy;

$R^s$ represents hydrogen or $C_1$-$C_6$-alkyl

A represents aryl or heteroaryl;

n represent an integer of 0, 1 or 2;

p represent an integer of 0, 1 or 2;

wherein, when one or more of $R^a$, $R^b$, $R^c$, $R^{d1}$, $R^{d2}$, $R^e$, $R^f$, $R^{g1}$ or $R^{g2}$ is (are) present in one position in the molecule as well as in one or more further positions in the molecule, said $R^a$, $R^b$, $R^c$, $R^{d1}$, $R^{d2}$, $R^e$, $R^f$, $R^{g1}$ or $R^{g2}$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^e$, $R^f$, $R^{g1}$ or $R^{g2}$ within a single molecule to be identical or different. For example, when $OR^c$ is present twice in the molecule, then the meaning of the first $OR^c$ may be O—$C_1$-$C_6$-alkyl, for example, and the meaning of the second $OR^c$ may be O—C(O)—$C_3$-$C_{10}$-cycloalkyl, for example;

or a salt, an N-oxide, a solvate, tautomer, or prodrug thereof.

In accordance with a more preferred embodiment, the present invention relates to compounds of general formula (I), in which:

$R^1$ represents hydrogen;

$R^2$ represents hydrogen, —C(O)$R^b$, or is selected from the group comprising, preferably consisting of —$C_1$-$C_6$-alkyl, —$C_3$-$C_6$-cycloalkyl, aryl and —$C_3$-$C_6$-heterocycloalkyl, wherein said residues are unsubstituted or substituted once with halogen, cyano, —$C_1$-$C_6$-alkyl, —$OR^c$, —$NR^{d1}R^{d2}$, —$C_1$-$C_6$-haloalkyl;

$R^3$ is selected from the group comprising, preferably consisting of —$C_1$-$C_6$-alkyl, —$C_2$-$C_6$-alkenyl, —$C_2$-$C_6$-alkynyl, aryl, heteroaryl and —$C_3$-$C_{10}$-cycloalkyl, wherein said residues are unsubstituted or substituted one or more times independently from each other with halogen, nitro, cyano, —$C_1$-$C_6$-alkyl, aryl, hetararyl, —$OR^c$, —$NR^{d1}R^{d2}$, —$C_1$-$C_6$-haloalkyl, —C(O)$R^b$, or —S(O)$_2R^b$;

$R^4$ is selected from the group comprising, preferably consisting of, hydrogen, —$OR^7$, —$SR^7$ and —$NR^7R^8$;

$R^5$ is selected from the group comprising, preferably consisting of, hydrogen, halogen, nitro, cyano, —$C_1$-$C_6$-alkyl, —$C_3$-$C_{10}$-cycloalkyl, —$C_1$-$C_6$-haloalkyl, —$C_1$-$C_6$-alkylthio, —(CH$_2$)$_n$$OR^f$, —(CH$_2$)$_n$$NR^sC(O)R^m$, —(CH$_2$)$_n$$NR^sS(O)_2R^m$, —(CH$_2$)$_n$$NR^{g1}R^{g2}$, —(CH$_2$)$_n$C(O)$R^n$, and —(CH$_2$)$_n$S(O)$_2R^n$;

$R^6$ is selected from the group comprising, preferably consisting of, hydrogen, halogen, nitro, cyano, hydroxyl, —$C_1$-$C_6$-alkyl, —$C_3$-$C_{10}$-cycloalkyl, —$C_1$-$C_6$-haloalkyl, —$C_1$-$C_6$-haloalkoxy, —$C_1$-$C_6$-alkoxy, and —$C_1$-$C_6$-alkylthio;

$R^7$, $R^8$ independently from each other are selected from the group comprising, preferably consisting of hydrogen, —$C_1$-$C_6$-alkyl, —$C_2$-$C_6$-alkenyl, —$C_2$-$C_6$-alkynyl, —$C_3$-$C_{10}$-cycloalkyl, —(CH$_2$)$_p$-aryl, —(CH$_2$)$_p$-heteroaryl and —$C_3$-$C_{10}$-heterocycloalkyl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, aryl, heteraryl, —$OR^c$, —$NR^{d1}R^{d2}$, —$C_1$-$C_6$-haloalkyl, —C(O)$R^b$, or —S(O)$_2R^b$; or $R^7$, $R^8$ in the context of a $NR^7R^8$ group together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —C(O)$R^e$, —S(O)$_2R^e$, or —OP(O)($OR^f$)$_2$; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

$R^a$ is selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^b$ is selected from the group comprising, preferably consisting of, —$OR^c$, —$SR^c$, —$NR^{d1}R^{d2}$, aryl, heteroaryl, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, —$NR^{g1}R^{g2}$ or $C_1$-$C_6$-alkoxy;

$R^c$ is selected from the group comprising, preferably consisting of, hydrogen, —C(O)$R^e$, —S(O)$_2R^e$, —P(O)($OR^f$)$_2$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —$OR^f$, —$NR^{d1}R^{d2}$, or —OP(O)($OR^f$)$_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, or for a group —C(O)$R^e$ or —S(O)$_2R^e$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$C_1$-$C_6$-alkyl, —$NR^{g1}R^{g2}$, —$OR^f$, —C(O)$R^e$, —S(O)$_2R^e$, or —OP(O)($OR^f$)$_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, C(O)$R^e$, —S(O)$_2R^e$, or —OP(O)($OR^f$)$_2$; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

$R^e$ is selected from the group comprising, preferably consisting of, —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is selected from the group comprising, preferably consisting of, hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, and/or —S(O)$_2$— group, and can optionally contain one or more double bonds;

R$^m$ is selected from the group comprising, preferably consisting of, C$_1$-C$_6$-alkyl, C$_3$-C$_{10}$-cycloalkyl and C$_3$-C$_{10}$-heterocycloalkyl;

R$^n$ is selected from the group comprising, preferably consisting of, —NR$^{g1}$R$^{g2}$, C$_1$-C$_6$-alkyl, C$_3$-C$_6$-cycloalkyl, hydroxyl and C$_1$-C$_6$-alkoxy;

R$^s$ represents hydrogen or C$_1$-C$_6$-alkyl

A represents aryl or heteroaryl;

n represent an integer of 0, 1 or 2;

p represent an integer of 0, 1 or 2;

wherein, when one or more of R$^a$, R$^b$, R$^c$, R$^{d1}$, R$^{d2}$, R$^e$, R$^f$, R$^{g1}$ or R$^{g2}$ is (are) present in one position in the molecule as well as in one or more further positions in the molecule, said R$^a$, R$^b$, R$^c$, R$^{d1}$, R$^{d2}$, R$^e$, R$^f$, R$^{g1}$ or R$^{g2}$ has (have), independently from each other, the same meanings as defined above in said first position in the molecule and in said second or further positions in the molecule, it being possible for the two or more occurrences of R$^a$, R$^b$, R$^c$, R$^{d1}$, R$^{d2}$, R$^e$, R$^f$, R$^{g1}$ or R$^{g2}$ within a single molecule to be identical or different. For example, when OR$^c$ is present twice in the molecule, then the meaning of the first OR$^c$ may be O—C$_1$-C$_6$-alkyl, for example, and the meaning of the second OR$^c$ may be O—C(O)—C$_3$-C$_{10}$-cycloalkyl, for example;

or a salt, an N-oxide, a solvate, tautomer, or prodrug thereof.

In accordance with a more particularly preferred embodiment, the present invention relates to compounds of general formula (I), in which R$^1$ represents hydrogen;

R$^2$ represents hydrogen, —C(O)R$^b$, or is selected from the group comprising, preferably consisting of —C$_1$-C$_6$-alkyl, —C$_3$-C$_6$-cycloalkyl, aryl and —C$_3$-C$_6$-heterocycloalkyl, wherein said residues are unsubstituted or substituted once with halogen, cyano, —C$_1$-C$_6$-alkyl, —OR$^c$, —NR$^{d1}$R$^{d2}$, —C$_1$-C$_6$-haloalkyl;

R$^3$ is selected from the group comprising, preferably consisting of —C$_1$-C$_6$-alkyl, phenyl and —C$_3$-C$_6$-cycloalkyl, wherein said residues are unsubstituted or substituted once with halogen, cyano, —C$_1$-C$_6$-alkyl, —OR$^c$, —NR$^{d1}$R$^{d2}$, —C$_1$-C$_6$-haloalkyl;

R$^4$ is selected from the group comprising, preferably consisting of, hydrogen, —OR$^7$, —SR$^7$ and —NR$^7$R$^8$;

R$^5$ is selected from the group comprising, preferably consisting of, hydrogen, halogen, nitro, cyano, —C$_1$-C$_6$-alkyl, —C$_3$-C$_{10}$-cycloalkyl, —C$_1$-C$_6$-haloalkyl, —C$_1$-C$_6$-alkylthio, —(CH$_2$)$_n$OR$^f$, —(CH$_2$)$_n$NR$^s$C(O)R$^m$, —(CH$_2$)$_n$NR$^s$S(O)$_2$R$^m$, —(CH$_2$)$_n$NR$^{g1}$R$^{g2}$, —(CH$_2$)$_n$C(O)R$^n$, and —(CH$_2$)$_n$S(O)$_2$R$^n$;

R$^6$ is selected from the group comprising, preferably consisting of, hydrogen, halogen, nitro, cyano, hydroxyl, —C$_1$-C$_6$-alkyl, —C$_3$-C$_{10}$-cycloalkyl, —C$_1$-C$_6$-haloalkyl, —C$_1$-C$_6$-haloalkoxy, —C$_1$-C$_6$-alkoxy, and —C$_1$-C$_6$-alkylthio;

R$^7$, R$^8$ independently from each other are selected from the group comprising, preferably consisting of hydrogen, —C$_1$-C$_6$-alkyl, —C$_2$-C$_6$-alkenyl, —C$_2$-C$_6$-alkynyl, —C$_3$-C$_{10}$-cycloalkyl, —(CH$_2$)$_p$-aryl, —(CH$_2$)$_p$-heteroaryl and —C$_3$-C$_{10}$-heterocycloalkyl, wherein said residues are unsubstituted or substituted one or more times independently from each other with halogen, nitro, cyano, —C$_1$-C$_6$-alkyl, —C$_3$-C$_{10}$-cycloalkyl, —C$_3$-C$_{10}$-heterocycloalkyl, aryl, heteroaryl, —OR$^c$, —NR$^{d1}$R$^{d2}$, —C$_1$-C$_6$-haloalkyl, —C(O)R$^b$, or —S(O)$_2$R$^b$; or R$^7$, R$^8$ in the context of a NR$^7$R$^8$ group together with the nitrogen atom to which they are attached, form a 3 to 10 membered heterocycloalkyl ring, which is optionally substituted one or more times, the same way or differently, with C$_1$-C$_6$-alkyl, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, and/or —S(O)$_2$— group, and can optionally contain one or more double bonds;

R$^a$ is selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl, wherein C$_1$-C$_6$-alkyl, and C$_3$-C$_{10}$-cycloalkyl are optionally substituted one or more times with hydroxyl, halogen, or C$_1$-C$_6$-alkoxy;

R$^b$ is selected from the group comprising, preferably consisting of, —OR$^c$, —SR$^c$, —NR$^{d1}$R$^{d2}$, aryl, heteroaryl, C$_1$-C$_6$-alkyl, and C$_3$-C$_{10}$-cycloalkyl, wherein C$_1$-C$_6$-alkyl, and C$_3$-C$_{10}$-cycloalkyl are optionally substituted one or more times with hydroxyl, halogen, —NR$^{g1}$R$^{g2}$ or C$_1$-C$_6$-alkoxy;

R$^c$ is selected from the group comprising, preferably consisting of, hydrogen, —C(O)R$^e$, —S(O)$_2$R$^e$, —P(O)(OR$^f$)$_2$, C$_1$-C$_6$-alkyl, C$_1$-C$_6$-haloalkyl C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with halogen, aryl, —OR$^f$, —NR$^{d1}$R$^{d2}$, or —OP(O)(OR$^f$)$_2$;

R$^{d1}$, R$^{d2}$ independently from each other are selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl, or for a group —C(O)R$^e$ or —S(O)$_2$R$^e$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —C$_1$-C$_6$-alkyl, —NR$^{g1}$R$^{g2}$, —OR$^f$, —C(O)R$^e$, —S(O)$_2$R$^e$, or —OP(O)(OR$^f$)$_2$; or R$^{d1}$ and R$^{d2}$ together with the nitrogen atom to which they are attached, form a 3 to 10 membered heterocycloalkyl ring, which is optionally substituted one or more times, the same way or differently, with C$_1$-C$_6$-alkyl, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, and/or —S(O)$_2$— group, and can optionally contain one or more double bonds;

R$^e$ is selected from the group comprising, preferably consisting of, —NR$^{g1}$R$^{g2}$, C$_2$-C$_6$-alkyl, C$_3$-C$_6$-cycloalkyl, C$_1$-C$_6$-alkoxy, aryl and heteroaryl;

R$^f$ is selected from the group comprising, preferably consisting of, hydrogen, —C(O)R$^e$, C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, C$_1$-C$_6$-alkoxy, aryl, or —NR$^{g1}$R$^{g2}$;

$R^{g1}$, $R^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

$R^m$ is selected from the group comprising, preferably consisting of, $C_1$-$C_6$-alkyl, $C_3$-$C_{10}$-cycloalkyl and $C_3$-$C_{10}$-heterocycloalkyl;

$R^n$ is selected from the group comprising, preferably consisting of, —$NR^{g1}R^{g2}$, $C_1$-$C_6$-alkyl, $C_3$-$C_6$-cycloalkyl, hydroxyl and $C_1$-$C_6$-alkoxy;

$R^s$ represents hydrogen or $C_1$-$C_6$-alkyl

A represents aryl or heteroaryl;

n represent an integer of 0, 1 or 2;

p represent an integer of 0, 1 or 2;

wherein, when one or more of $R^a$, $R^b$, $R^c$, $R^{d1}$, $R^{d2}$, $R^e$, $R^f$, $R^{g1}$ or $R^{g2}$ is (are) present in one position in the molecule as well as in one or more further positions in the molecule, said $R^a$, $R^b$, $R^c$, $R^{d1}$, $R^{d2}$, $R^e$, $R^f$, $R^{g1}$ or $R^{g2}$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^e$, $R^f$, $R^{g1}$ or $R^{g2}$ within a single molecule to be identical or different. For example, when $OR^c$ is present twice in the molecule, then the meaning of the first $OR^c$ may be O—$C_1$-$C_6$-alkyl, for example, and the meaning of the second $OR^c$ may be O—C(O)—$C_3$-$C_{10}$-cycloalkyl, for example;

or a salt, an N-oxide, a solvate, tautomer, or prodrug thereof.

In accordance with a yet more particularly preferred embodiment, the present invention relates to compounds of general formula (I), in which:

$R^1$ represents hydrogen;

$R^2$ represents hydrogen, —C(O)$R^b$, or is selected from the group comprising, preferably consisting of —$C_1$-$C_6$-alkyl, —$C_3$-$C_6$-cycloalkyl, wherein said residues are unsubstituted or substituted once with $C_1$-$C_6$-alkyl, —$OR^c$, or —$NR^{d1}R^{d2}$;

$R^3$ is selected from the group comprising, preferably consisting of —$C_1$-$C_6$-alkyl, phenyl and —$C_3$-$C_6$-cycloalkyl, wherein said residues are unsubstituted or substituted once with halogen, —$C_1$-$C_6$-alkyl, —$OR^c$, or $NR^{d1}R^{d2}$;

$R^4$ is selected from the group comprising, preferably consisting of, hydrogen, —$OR^7$, —$SR^7$ and —$NR^7R^8$;

$R^5$ is selected from the group comprising, preferably consisting of, hydrogen, halogen, nitro, cyano, —$C_1$-$C_6$-alkyl, —$C_3$-$C_{10}$-cycloalkyl, —$C_1$-$C_6$-haloalkyl, —$C_1$-$C_6$-alkylthio, —(CH$_2$)$_n$$OR^f$, —(CH$_2$)$_n$$NR^sC(O)R^m$, —(CH$_2$)$_n$$NR^sS(O)_2R^m$, —(CH$_2$)$_n$$NR^{g1}R^{g2}$, —(CH$_2$)$_n$$C(O)R^n$, and —(CH$_2$)$_n$$S(O)_2R^n$;

$R^6$ is selected from the group comprising, preferably consisting of, hydrogen, halogen, nitro, cyano, hydroxyl, —$C_1$-$C_6$-alkyl, —$C_3$-$C_{10}$-cycloalkyl, —$C_1$-$C_6$-haloalkyl, —$C_1$-$C_6$-haloalkoxy, —$C_1$-$C_6$-alkoxy, and —$C_1$-$C_6$-alkylthio;

$R^7$, $R^8$ independently from each other are selected from the group comprising, preferably consisting of hydrogen, —$C_1$-$C_6$-alkyl, —$C_2$-$C_6$-alkenyl, —$C_2$-$C_6$-alkynyl, —$C_3$-$C_{10}$-cycloalkyl, —(CH$_2$)$_p$-aryl, —(CH$_2$)$_p$-heteroaryl and —$C_3$-$C_{10}$-heterocycloalkyl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, aryl, heteroaryl, —$OR^c$, —$NR^{d1}R^{d2}$, —$C_1$-$C_6$-haloalkyl, —C(O)$R^b$, or —S(O)$_2R^b$; or $R^7$, $R^8$ in the context of a $NR^7R^8$ group together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —C(O)$R^e$, —S(O)$_2R^e$, or —OP(O)(O$R^f$)$_2$; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

$R^a$ is selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^b$ is selected from the group comprising, preferably consisting of, —$OR^c$, —$SR^c$, —$NR^{d1}R^{d2}$, aryl, heteroaryl, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, —$NR^{g1}R^{g2}$ or $C_1$-$C_6$-alkoxy;

$R^c$ is selected from the group comprising, preferably consisting of, hydrogen, —C(O)$R^e$, —S(O)$_2R^e$, —P(O)(O$R^f$)$_2$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —$OR^f$, —$NR^{d1}R^{d2}$, or —OP(O)(O$R^f$)$_2$;

$R^{d1}$, $R^{d2}$ independently from each other are selected from the group comprising, preferably consisting of, hydrogen, $C_1$-$C_6$-alkyl, $C_3$-$C_{10}$-cycloalkyl, $C_3$-$C_{10}$-heterocycloalkyl, aryl, and heteroaryl, or for a group —C(O)$R^e$ or —S(O)$_2R^e$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$C_1$-$C_6$-alkyl, —$NR^{g1}R^{g2}$, —$OR^f$, —C(O)$R^e$, —S(O)$_2R^e$, or —OP(O)(O$R^f$)$_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —C(O)$R^e$, —S(O)$_2R^e$, or —OP(O)(O$R^f$)$_2$; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

$R^e$ is selected from the group comprising, preferably consisting of, —$NR^{g1}R^{g2}$, $C_2$-$C_6$-alkyl, $C_3$-$C_6$-cycloalkyl, $C_1$-$C_6$-alkoxy, aryl and heteroaryl;

$R^f$ is selected from the group comprising, preferably consisting of, hydrogen, —C(O)R$^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —NR$^{g1}$R$^{g2}$;

$R^{g1}$, $R^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, and/or —S(O)$_2$— group, and can optionally contain one or more double bonds;

$R^m$ is selected from the group comprising, preferably consisting of, $C_1$-$C_6$-alkyl, $C_3$-$C_{10}$-cycloalkyl and $C_3$-$C_{10}$-heterocycloalkyl;

$R^n$ is selected from the group comprising, preferably consisting of, —NR$^{g1}$R$^{g2}$, $C_1$-$C_6$-alkyl, $C_3$-$C_6$-cycloalkyl, hydroxyl and $C_1$-$C_6$-alkoxy;

$R^s$ represents hydrogen or $C_1$-$C_6$-alkyl

A represents aryl or heteroaryl;

n represent an integer of 0, 1 or 2;

p represent an integer of 0, 1 or 2;

wherein, when one or more of $R^a$, $R^b$, $R^c$, $R^{d1}$, $R^{d2}$, $R^e$, $R^f$, $R^{g1}$ or $R^{g2}$ is (are) present in one position in the molecule as well as in one or more further positions in the molecule, said $R^a$, $R^b$, $R^c$, $R^{d1}$, $R^{d2}$, $R^e$, $R^f$, $R^{g1}$ or $R^{g2}$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^e$, $R^f$, $R^{g1}$ or $R^{g2}$ within a single molecule to be identical or different. For example, when OR$^c$ is present twice in the molecule, then the meaning of the first OR$^c$ may be O—$C_1$-$C_6$-alkyl, for example, and the meaning of the second OR$^c$ may be O—C(O)—$C_3$-$C_{10}$-cycloalkyl, for example;

or a salt, an N-oxide, a solvate, tautomer, or prodrug thereof.

Definitions

Within the context of the present application, the terms as mentioned in this description and in the claims have preferably the following meanings:

The term "alkyl" is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and isomers thereof.

The term "haloalkyl" is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "alkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and isomers thereof.

The term "alkylthio" is to be understood as preferably meaning branched and unbranched alkylthio, meaning e.g. methylthio, ethylthio, propylthio, iso-propylthio, butylthio, iso-butylthio, tert-butylthio, sec-butylthio, pentylthio, iso-pentylthio, hexylthio, heptylthio, octylthio, nonylthio, decylthio, undecylthio and dodecylthio and the isomers thereof.

The term "haloalkoxy" is to be understood as preferably meaning branched and unbranched alkoxy, as defined supra, in which one or more of the hydrogen substituents is replaced in the same way or differently with halogen, e.g. chloromethoxy, fluoromethoxy, pentafluoroethoxy, fluoropropyloxy, difluoromethyloxy, trichloromethoxy, 2,2,2-trifluoroethoxy, bromobutyloxy, trifluoromethoxy, iodoethoxy, and isomers thereof.

The term "cycloalkyl" is to be understood as preferably meaning a $C_3$-$C_{10}$ cycloalkyl group, more particularly a saturated cycloalkyl group of the indicated ring size, meaning e.g. a cyclopropyl, cyclobutyl, cyclopentyl, cyclohexyl, cycloheptyl, cyclooctyl, cyclononyl, or cyclodecyl group; and also as meaning an unsaturated cycloalkyl group containing one or more double bonds in the C-backbone, e.g. a $C_3$-$C_{10}$ cycloalkenyl group, such as, for example, a cyclopropenyl, cyclobutenyl, cyclopentenyl, cyclohexenyl, cycloheptenyl, cyclooctenyl, cyclononenyl, or cyclodecenyl group, wherein the linkage of said cycloalkyl group to the rest of the molecule can be provided to the double or single bond; and also as meaning such a saturated or unsaturated cycloalkyl group being optionally substituted one or more times, independently from each other, with a $C_1$-$C_6$-alkyl group and/or a hydroxyl group and/or a dimethylamino group, such as, for example, a 2-methyl-cyclopropyl group, a 2,2-dimethylcyclopropyl group, a 2,2-dimethylcyclobutyl group, a 3-hydroxycyclopentyl group, a 3-hydroxycyclohexyl group, a 3-dimethylaminocyclobutyl group, a 3-dimethylaminocyclopentyl group or a 4-dimethylaminocyclohexyl group.

The term "heterocycloalkyl" is to be understood as preferably meaning a $C_3$-$C_{10}$ cycloalkyl group, as defined supra, featuring the indicated number of ring atoms, wherein one or more ring atom(s) is (are) (a) heteroatom(s) such as NH, NR$^a$, O, S, or (a) group(s) such as a C(O), S(O), S(O)$_2$, or, otherwise stated, in a $C_n$-cycloalkyl group, (wherein n is an integer of 3, 4, 5, 6, 7, 8, 9, or 10), one or more carbon atom(s) is (are) replaced by said heteroatom(s) or said group(s) to give such a $C_n$ cycloheteroalkyl group; and also as meaning an unsaturated heterocycloalkyl group containing one or more double bonds in the C-backbone, wherein the linkage of said heterocyclolalkyl group to the rest of the molecule can be provided to the double or single bond; and also as meaning such a saturated or unsaturated heterocycloalkyl group being optionally substituted one or more times, independently from each other, by a $C_1$-$C_6$ alkyl group and/or a hydroxyl group and/or a dimethylamino group. Thus, said $C_n$ cycloheteroalkyl group refers, for example, to a three-membered heterocycloalkyl, expressed as $C_3$-heterocycloalkyl, such as oxiranyl ($C_3$). Other examples of heterocycloalkyls are oxetanyl ($C_4$), aziridinyl ($C_3$), azetidinyl ($C_4$), tetrahydrofuranyl ($C_5$), pyrrolidinyl ($C_5$), morpholinyl ($C_6$), dithianyl ($C_6$), thiomorpholinyl ($C_6$), piperidinyl ($C_6$), tetrahydropyranyl ($C_6$), piperazinyl ($C_6$), trithianyl ($C_6$) and chinuclidinyl ($C_8$).

The term "halogen" or "Hal" is to be understood as preferably meaning fluorine, chlorine, bromine, or iodine.

The term "alkenyl" is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group, and isomers thereof.

The term "alkynyl" is to be understood as preferably meaning branched and unbranched alkynyl, e.g. an ethynyl, prop-1-yn-1-yl, but-1-yn-1-yl, but-2-yn-1-yl, or but-3-yn-1-yl group, and isomers thereof.

As used herein, the term "aryl" is defined in each case as having 3-12 carbon atoms, preferably 6-12 carbon atoms, such as, for example, cyclopropenyl, phenyl, tropyl, indenyl, naphthyl, azulenyl, biphenyl, fluorenyl, anthracenyl etc, phenyl being preferred.

As used herein, the term "heteroaryl" is understood as meaning an aromatic ring system which comprises 3-16 ring atoms, preferably 5 or 6 or 9 or 10 atoms, and which contains at least one heteroatom which may be identical or different, said heteroatom being such as nitrogen, NH, $NR^a$, oxygen, or sulphur, and can be monocyclic, bicyclic, or tricyclic, and in addition in each case can be benzocondensed. It is to be understood that the term "heteroaryl" is intended to include 3-16-membered bi- or tricyclic ring systems, containing at least one heteroatom as defined above, in which part of the polycyclic ring system is saturated. It is to be further understood that "heteroaryl" also means those ring systems which can form an equilibrium of tautomeric forms in which one tautomeric form possesses aromatic characteristics. More particularly, meaning a monocyclic, bicyclic or tricyclic (partially) unsaturated ring system which contains one (or more) $-C(O)NR^a-$ group(s), such as, for example, a pyridone, a pyrimidinone, or benzocondensed analogues thereof, and also including pyranones and benzocondensed derivatives thereof. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl; pyridonyl, or pyrimidonyl.

The term "alkylene", as used herein in the context of the compounds of general formula (I) is to be understood as meaning an optionally substituted alkyl chain or "tether", having 1, 2, 3, 4, 5, or 6 carbon atoms, i.e. an optionally substituted $-CH_2-$ ("methylene" or "single membered tether") or e.g. $-C(Me)_2-$, or $-CH(Me)-$ [(R)— or (S)-isomers], $-CH_2-CH_2-$ ("ethylene", "dimethylene", or "two-membered tether"), $-CH_2-CH_2-CH_2-$ ("propylene", "trimethylene", or "three-membered tether"), $-CH_2-CH_2-CH_2-CH_2-$ ("butylene", "tetramethylene", or "four-membered tether"), $-CH_2-CH_2-CH_2-CH_2-CH_2-$ ("pentylene", "pentamethylene" or "five-membered ether"), or $-CH_2-CH_2-CH_2-CH_2-CH_2-CH_2-$ ("hexylene", "hexamethylene", or six-membered tether") group. Preferably, said alkylene tether is 1, 2, 3, 4, or 5 carbon atoms, more preferably 1 or 2 carbon atoms.

The term "cycloalkylene", as used herein in the context of the compounds of general formula (I) is to be understood as meaning an optionally substituted cycloalkyl ring, having 3, 4, 5, 6, 7, 8, 9 or 10, preferably 3, 4, 5, or 6, carbon atoms, i.e. an optionally substituted cyclopropyl, cyclobutyl, cyclopentyl, cyclohexyl, cycloheptyl, cyclooctyl, cyclononyl, or cyclodecyl ring, preferably a cyclopropyl, cyclobutyl, cyclopentyl or cyclohexyl ring.

The term "heterocycloalkylene", as used herein in the context of the compounds of general formula (I) is to be understood as meaning a cycloalkylene ring, as defined supra, but which contains at least one heteroatom which may be identical or different, said heteroatom being such as O, NH, $NR^a$, S, S(O) or $S(O)_2$.

The term "arylene", as used herein in the context of the compounds of general formula (I) is to be understood as meaning a tether, (otherwise known as a "linker" or a "spacer"), formed by an optionally substituted monocyclic or polycyclic arylene aromatic system e.g. arylene, naphthylene and biarylene, preferably an optionally substituted phenyl ring, having 6 or 10 carbon atoms. More preferably, said arylene tether is a ring having 6 carbon atoms, i.e. a "phenylene" ring. If the term "arylene" or e.g. "phenylene" is used it is to be understood that the linking residues can be arranged to each other in ortho-, para- and meta-position, eg. an optionally substituted moiety of structure:

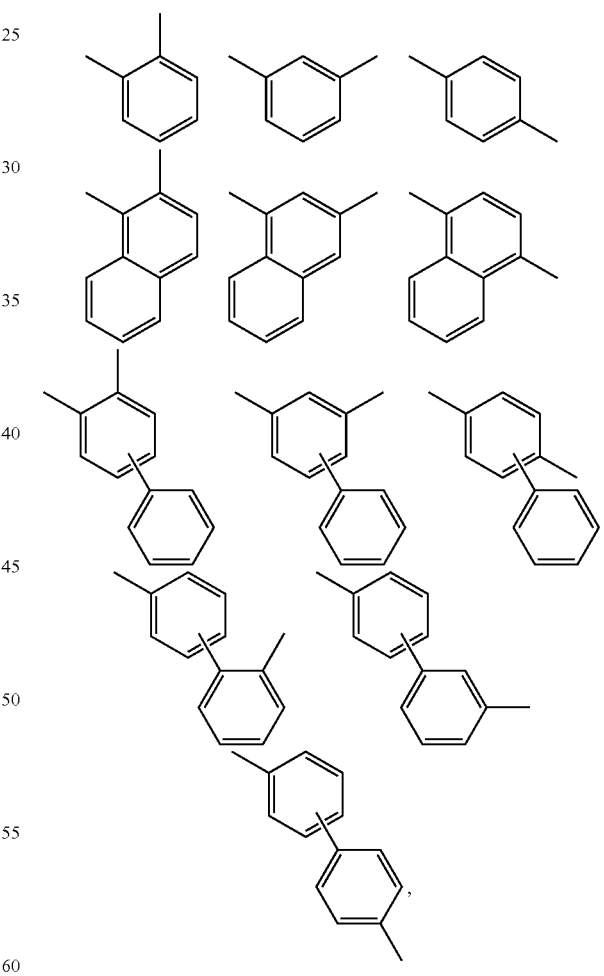

in which linking positions on the rings are shown as non-attached bonds.

The term "heterocyclic", as used herein in the context of the compounds of general formula (I) is to be understood as meaning a tether, (otherwise known as a "linker" or a "spacer"), formed by an optionally substituted monocyclic or polycyclic heteroarylene aromatic system, e.g. heteroarylene, benzoheteroarylene, preferably an optionally substituted 5-membered heterocycle, such as, for example, furan, pyrrole, thiazole, oxazole, isoxazole, or thiophene, or a 6-membered heterocycle, such as, for example, pyridine, pyrimidine, pyrazine, pyridazine. More preferably, said heteroarylene tether is a ring having 6 atoms, e.g. an optionally substituted structure as shown supra for the arylene moieties, but which contains at least one heteroatom which may be identical or different, said heteroatom being such as nitrogen, NH, $NR^a$, oxygen, or sulphur. If the term "heteroarylene" is used it is to be understood that the linking residues can be arranged to each other in ortho-, para- and meta-position.

As used herein, the term "$C_1$-$C_6$", as used throughout this text, e.g. in the context of the definition of "$C_1$-$C_6$-alkyl", or "$C_1$-$C_6$-alkoxy", is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_2$, $C_1$-$C_3$, $C_1$-$C_4$, $C_1$-$C_5$, $C_1$-$C_6$; more preferably $C_1$-$C_3$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; preferably $C_2$-$C_3$.

As used herein, the term "$C_3$-$C_{10}$", as used throughout this text, e.g. in the context of the definitions of "$C_3$-$C_{10}$-cycloalkyl" or "$C_3$-$C_{10}$-heterocycloalkyl", is to be understood as meaning a cycloalkyl group having a finite number of carbon atoms of 3 to 10, i.e. 3, 4, 5, 6, 7, 8, 9 or 10 carbon atoms, preferably 3, 4, 5 or 6 carbon atoms. It is to be understood further that said term "$C_3$-$C_{10}$" is to be interpreted as any sub-range comprised therein, e.g. $C_3$-$C_{10}$, $C_4$-$C_9$, $C_5$-$C_8$, $C_6$-$C_7$; preferably $C_3$-$C_6$.

As used herein, the term "$C_3$-$C_6$", as used throughout this text, e.g. in the context of the definitions of "$C_3$-$C_6$-cycloalkyl" or "$C_3$-$C_6$-heterocycloalkyl", is to be understood as meaning a cycloalkyl group having a finite number of carbon atoms of 3 to 6, i.e. 3, 4, 5, or 6 carbon atoms. It is to be understood further that said term "$C_3$-$C_6$" is to be interpreted as any sub-range comprised therein, e.g. $C_3$-$C_4$, $C_4$-$C_6$, $C_5$-$C_6$.

As used herein, the term "$C_6$-$C_{11}$", as used throughout this text, e.g. in the context of the definitions of "$C_6$-$C_{11}$-aryl", is to be understood as meaning an aryl group having a finite number of carbon atoms of 5 to 11, i.e. 5, 6, 7, 8, 9, 10 or 11 carbon atoms, preferably 5, 6, or 10 carbon atoms. It is to be understood further that said term "$C_6$-$C_{11}$" is to be interpreted as any sub-range comprised therein, e.g. $C_5$-$C_{10}$, $C_6$-$C_9$, $C_7$-$C_8$; preferably $C_5$-$C_6$.

As used herein, the term "$C_5$-$C_{10}$", as used throughout this text, e.g. in the context of the definitions of "$C_5$-$C_{10}$-heteroaryl", is to be understood as meaning a heteroaryl group having a finite number of carbon atoms of 5 to 10, in addition to the one or more heteroatoms present in the ring i.e. 5, 6, 7, 8, 9, or 10 carbon atoms, preferably 5, 6, or 10 carbon atoms. It is to be understood further that said term "$C_5$-$C_{10}$" is to be interpreted as any sub-range comprised therein, e.g. $C_6$-$C_9$, $C_7$-$C_8$, $C_7$-$C_8$; preferably $C_5$-$C_6$.

As used herein, the term "$C_1$-$C_3$", as used throughout this text, e.g. in the context of the definitions of "$C_1$-$C_3$-alkylene", is to be understood as meaning an alkylene group as defined supra having a finite number of carbon atoms of 1 to 3, i.e. 1, 2, or 3. It is to be understood further that said term "$C_1$-$C_3$" is to be interpreted as any sub-range comprised therein, e.g. $C_1$-$C_2$, or $C_2$-$C_3$.

As used herein, the term "one or more times", e.g. in the definition of the substituents of the compounds of the general formulae of the present invention, is understood as meaning "one, two, three, four or five times, particularly one, two, three or four times, more particularly one, two or three times, more particularly one or two times".

The term "isomers" is to be understood as meaning chemical compounds with the same number and types of atoms as another chemical species. There are two main classes of isomers, constitutional isomers and stereoisomers.

The term "constitutional isomers" is to be understood as meaning chemical compounds with the same number and types of atoms, but they are connected in differing sequences. There are functional isomers, structural isomers, tautomers or valence isomers.

In "stereoisomers", the atoms are connected sequentially in the same way, such that condensed formulae for two isomeric molecules are identical. The isomers differ, however, in the way the atoms are arranged in space. There are two major sub-classes of stereoisomers; conformational isomers, which interconvert through rotations around single bonds, and configurational isomers, which are not readily interconvertable.

Configurational isomers are, in turn, comprised of enantiomers and diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers.

The term "tautomer" is understood as meaning a compound which is interconvertible, by tautomerisation, to another compound by a migration of a hydrogen atom accompanied by a switch of an adjacent conjugated double bond. In cases where tautomerisation is possible, a chemical equilibrium of the tautomers can be reached. The exact ratio of the tautomers depends on several factors, including temperature, solvent, and pH. Within the context of the present invention, the term "tautomer" is understood as meaning a single tautomer, or a mixture of tautomers in any ratio.

The term "metabolite" is understood as meaning a compound produced in a living organism or in a cell culture by one (or more) metabolic transformation(s) of a compound of general formula I. Metabolic transformations in this context include, but are not limited to, hydroxylations, oxygenations, oxidations, reductions, demethylations, deacylations, acylations, sulfonylations, glucuronidations, eliminations, hydrations, hydrolysis reactions, ipso substitutions, saponifications, desaminations, aminations and amide saponifications.

In order to limit different types of isomers from each other reference is made to IUPAC Rules Section E (*Pure Appl Chem* 45, 11-30, 1976).

Further Embodiments

The compounds of the present invention according to Formula (I) can exist in free form or in a salt form. A suitable pharmaceutically acceptable salt of the alkynylpyrimidines of the present invention may be, for example, an acid-addition salt of a alkynylpyrimidines of the invention which is sufficiently basic, for example, an acid-addition salt with, for example, an inorganic or organic acid, for example hydrochloric, hydrobromic, sulfuric, phosphoric, trifluoroacetic, para-toluenesulfonic, methylsulfonic, citric, tartaric, lactic, succinic or maleic acid. In addition, another suitable pharmaceutically acceptable salt of a alkynylpyrimidines of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, 1,6-hexadiamine, ethanolamine, glucosamine, sarcosine, serinol, tris-hydroxy-methyl-aminomethane, aminopropandiol, sovak-base, 1-amino-2,3,4-butantriol.

The compounds of the present invention according to Formula (I) can exist as N-oxides which are defined in that at least one nitrogen of the compounds of the general Formula (I) may be oxidized.

The compounds of the present invention according to Formula (I) or salts or N-oxides thereof can exist as solvates, in particular as hydrates, wherein compounds of the present invention according to Formula (I) or salts or N-oxides thereof may contain polar solvents, in particular water, as structural element of the crystal lattice of the compounds. The amount of polar solvents, in particular water, may exist in a stoichiometric or unstoichiometric ratio. In case of stoichiometric solvates, e.g. hydrates, hemi-, (semi-), mono-, sesqui-, di-, tri-, tetra-, penta- etc. solvates or hydrates are possible.

The compounds of the present invention according to Formula (I) can exist as prodrugs, e.g. as an in vivo cleavable derivative of a compound of general formula I, for example, as an in vivo hydrolysable esters. As used herein, the term "in vivo hydrolysable ester" is understood as meaning an in vivo hydrolysable ester of a compound of formula (I) containing a carboxy or hydroxyl group, for example, a pharmaceutically acceptable ester which is hydrolysed in the human or animal body to produce the parent acid or alcohol. Suitable pharmaceutically acceptable esters for carboxy groups include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_{10}$ cycloalkoxycarbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of formula (I) containing a hydroxyl group includes inorganic esters such as phosphate esters and α-acyloxyalkyl ethers and related compounds which as a result of the in vivo hydrolysis of the ester breakdown to give the parent hydroxyl group. Examples of α-acyloxyalkyl ethers include acetoxymethoxy and 2,2-dimethylpropionyloxymethoxy. A selection of in vivo hydrolysable ester forming groups for hydroxyl include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention according to Formula (I) can exist as tautomers.

The compounds of the present invention according to Formula (I) and salts, solvates, metabolites, N-oxides and prodrugs thereof may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred stereoisomers are those with the configuration which produces the more desirable biological activity. Separated, pure or partially purified configurational isomers or racemic mixtures of the compounds of this invention are also included within the scope of the present invention. The purification of said isomers and the separation of said isomeric mixtures can be accomplished by standard techniques known in the art.

Another embodiment of the present invention relates to the use of a compound of general formula 6 as mentioned below for the preparation of a compound of general formula (I) as defined supra.

Another embodiment of the present invention relates to the use of a compound of general formula 5 as mentioned below for the preparation of a compound of general formula (I) as defined supra.

Another embodiment of the present invention relates to the use of a compound of general formula 5' as mentioned below for the preparation of a compound of general formula (I) as defined supra.

Another embodiment of the present invention relates to the use of a compound of general formula Ia as mentioned below for the preparation of a compound of general formula Ib as defined supra.

The compounds of the present invention can be used in treating diseases of dysregulated vascular growth or diseases which are accompanied with dysregulated vascular growth. Especially, the compounds effectively interfere with cellular Tie2 and VEGFR2 signalling.

Therefore, another aspect of the present invention is a use of the compound of general formula (I) described supra for manufacturing a pharmaceutical composition for the treatment of diseases of dysregulated vascular growth or of diseases which are accompanied with dysregulated vascular growth.

In particular, said use is in the treatment of diseases, wherein the diseases are tumors and/or metastases thereof. The compounds of the present invention can be used in particular in therapy and prevention of tumor growth and metastases, especially in solid tumors of all indications and stages with or without pre-treatment if the tumor growth is accompanied with persistent angiogenesis, principally including all solid tumors, e.g. breast, colon, renal, ovarian, prostate, head, neck, pancreas, GI tract, thyroid, lung and/or brain tumors, melanoma, or metastases thereof.

Additionally, said use is in the treatment of chronic myelogeneous leukaemia (or "CML"), acute myelogenous leukaemia (or "AML"), acute lymphatic leukaemia, acute lymphocytic leukaemia (or "ALL"), chronic lymphocytic leukaemia, chronic lymphatic leukaemia (or "CLL") as well as other myeloid precursor hyperplasias such as polycythemia vera and myelofibrosis.

Another use is in the treatment of diseases, wherein the diseases are retinopathy, other angiogenesis dependent diseases of the eye, in particular cornea transplant rejection or age-related macular degeneration.

Yet another use is in the treatment of rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and inflammatory diseases of the bowel, such as, for example, Crohn's disease.

A further use is in the suppression of the development of atherosclerotic plaque formation and for the treatment of coronary and peripheral artery disease.

Another use is in the treatment of diseases associated with stromal proliferation or characterized by pathological stromal reactions and for the treatment of diseases associated with deposition of fibrin or extracellular matrix, such as, for example, fibrosis, cirrhosis and carpal tunnel syndrome.

Yet another use is in the treatment of gynaecological diseases where inhibition of angiogenic, inflammatory and stromal processes with pathological character can be inhibited, such as, for example, endometriosis, pre-eclampsia, postmenopausal bleeding and ovarian hyperstimulation.

Another use is in the treatment of diseases, wherein the diseases are ascites, oedema such as brain tumor associated oedema, high altitude trauma, hypoxia induced cerebral oedema, pulmonary oedema and macular oedema or oedema following burns and trauma, chronic lung disease, adult respiratory distress syndrome, bone resorption and for the treatment of benign proliferating diseases such as myoma and benign prostate hyperplasia.

A further use is in wound healing for the reduction of scar formation, and for the reduction of scar formation during regeneration of damaged nerves.

Yet another aspect of the invention is a method of treating a disease of dysregulated vascular growth or diseases which are accompanied with dysregulated vascular growth, by administering an effective amount of a compound of general formula (I) described supra.

In particular, the diseases of said method are tumors and/or metastases thereof, in particular solid tumors of all indications and stages with or without pre-treatment if the tumor growth is accompanied with persistent angiogenesis, principally including all solid tumors, e.g. breast, colon, renal, ovarian, prostate, head, neck, pancreas, GI tract, thyroid, lung and/or brain tumors, melanoma, or metastases thereof.

Additionally, diseases of said method are chronic myelogeneous leukaemia (or "CML"), acute myelogenous leukaemia (or "AML"), acute lymphatic leukaemia, acute lymphocytic leukaemia (or "ALL"), chronic lymphocytic leukaemia, chronic lymphatic leukaemia (or "CLL") as well as other myeloid precursor hyperplasias such as polycythemia vera and myelofibrosis.

Further diseases of said method are retinopathy, other angiogenesis dependent diseases of the eye, in particular cornea transplant rejection or age-related macular degeneration.

Further diseases of said method are rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and inflammatory diseases of the bowel, such as, for example, Crohn's disease.

Further diseases of said method are the development of atherosclerotic plaques and coronary and peripheral artery diseases.

Further diseases of said method are diseases associated with stromal proliferation or characterized by pathological stromal reactions and diseases associated with deposition of fibrin or extracellular matrix, such as, for example, fibrosis, cirrhosis and carpal tunnel syndrome.

Further diseases of said method are gynaecological diseases where inhibition of angiogenic, inflammatory and stromal processes with pathological character can be inhibited, such as, for example, endometriosis, pre-eclampsia, postmenopausal bleeding and ovarian hyperstimulation.

Further diseases of said method are ascites, oedema such as brain tumor associated oedema, high altitude trauma, hypoxia induced cerebral oedema, pulmonary oedema and macular oedema or oedema following burns and trauma, chronic lung disease, adult respiratory distress syndrome, bone resorption and benign proliferating diseases such as myoma and benign prostate hyperplasia.

Another aspect of the present invention is a pharmaceutical composition which comprises a compound of general formula (I) as defined above, or as obtainable by a method described in this invention, or a pharmaceutically acceptable salt or an N-oxide or a solvate or a prodrug or a tautomer of said compound, and a pharmaceutically acceptable diluent or carrier, the composition being particularly suited for the treatment of diseases of dysregulated vascular growth or of diseases which are accompanied with dysregulated vascular growth as explained above.

In order to use the compounds of the present invention as pharmaceutical products, the compounds or mixtures thereof may be provided in a pharmaceutical composition, which, as well as the compounds of the present invention for enteral, oral or parenteral application contains suitable pharmaceutically acceptable organic or inorganic inert base material, e.g. purified water, gelatine, gum Arabic, lactate, starch, magnesium stearate, talcum, vegetable oils, polyalkyleneglycol, etc.

The pharmaceutical compositions of the present invention may be provided in a solid form, e.g. as tablets, dragees, suppositories, capsules or in liquid form, e.g. as a solution, suspension or emulsion. The pharmaceutical composition may additionally contain auxiliary substances, e.g. preservatives, stabilisers, wetting agents or emulsifiers, salts for adjusting the osmotic pressure or buffers.

For parenteral applications, (including intravenous, subcutaneous, intramuscular, intravascular or infusion), sterile injection solutions or suspensions are preferred, especially aqueous solutions of the compounds in polyhydroxyethoxy containing castor oil.

The pharmaceutical compositions of the present invention may further contain surface active agents, e.g. salts of gallenic acid, phospholipids of animal or vegetable origin, mixtures thereof and liposomes and parts thereof.

For oral application tablets, dragees or capsules with talcum and/or hydrocarbon-containing carriers and binders, e.g. lactose, maize and potato starch, are preferred. Further application in liquid form is possible, for example as juice, which contains sweetener if necessary.

The dosage will necessarily be varied depending upon the route of administration, age, weight of the patient, the kind and severity of the illness being treated and similar factors. A dose can be administered as unit dose or in part thereof and distributed over the day. Accordingly the optimum dosage may be determined by the practitioner who is treating any particular patient.

It is possible for compounds of general formula (I) of the present invention to be used alone or, indeed in combination with one or more further drugs, particularly anti-cancer drugs or compositions thereof. Particularly, it is possible for said combination to be a single pharmaceutical composition entity, e.g. a single pharmaceutical formulation containing one or more compounds according to general formula (I) together with one or more further drugs, particularly anti-cancer drugs, or in a form, e.g. a "kit of parts", which comprises, for example, a first distinct part which contains one or more compounds according to general formula (I), and one or more further distinct parts each containing one or more further drugs, particularly anti-cancer drugs. More particularly, said first distinct part may be used concomitantly with said one or more further distinct parts, or sequentially. In addition, it is possible for compounds of general formula (I) of the present invention to be used in combination with other treatment paradigms, particularly other anti-cancer treatment paradigms, such as, for example, radiation therapy.

Another aspect of the present invention is a method which may be used for preparing the compounds according to the present invention.

Experimental Details and General Processes

The following table lists the abbreviations used in this paragraph and in the Examples section as far as they are not explained within the text body. NMR peak forms are stated as they appear in the spectra, possible higher order effects have not been considered. Assignments of substitution degrees (e.g. $CH_3$, $CH_2$, CH or Cq signals) of carbon atoms in $^{13}C$-NMR spectra are based on $^{13}C$-DEPT NMR analysis. Chemical names were generated by or in analogy to AutoNom2000 as implemented in MDL ISIS Draw. In some cases generally accepted names of commercially available reagents were used in place of AutoNom2000 generated names. It is furthermore made reference to the point that, as is clear to the person skilled in the art, a compound which contains a —S(=O)(=NH)— functional group (or a substituted derivative thereof), is referred to as a "sulfoximine", whereas a compound with such a functional group can also be designated as "sulfoximide" or "sulphoximine" or "sulphoximide" or by the prefix "-sulfonimidoyl-". Certain compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash $NH_2$ silica gel in combination with a Flashmaster II autopurifier (Argonaut/Biotage) and eluents such as gradients of hexane/EtOAc or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid or aqueous ammonia. Purification of compounds by HPLC may give rise to their isolation as salts, such as, for example, as TFA salts, as formic acid salts or as ammonium salts. Conversion of such a salt into the respective free base can be accomplished by standard laboratory procedures as known to the person skilled in the art. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. Compounds or reaction mixtures may be analysed by means of HPLC/MS to give purity data based on UV/DAD detection, retention times and MS, in particular ESI data which may be utilised to characterise compounds. More specifically, certain compounds of the invention have been analysed using the following conditions:

Analytical HPLC/MS Conditions A (Hereinafter HPLC Method A)

HPLC/MS analyses were run by using a 1525μ binary HPLC pump, a Micromass ZQ MS detector, and a MUX UV 2488 detector (all by Waters, Inc.). As HPLC column, a Purospher Star RP C18 4.6×125 5 μm (Merck) was employed; detection wavelength 214 nm; flow rate 1 ml/min; eluents A: 0.1% TFA in $H_2O$, B $CH_3CN$; gradient in each case based on B: 5% to 95% (10').

Analytical HPLC/MS Conditions B (Hereinafter HPLC Method B)

HPLC/MS analyses were run by using a 1525μ binary HPLC pump, a Micromass ZQ MS detector, and a MUX UV 2488 detector (all by Waters, Inc.). As HPLC column, a XBridge C18 4.6×50 3.5 μM (Waters) was employed; detection wavelength 214 nm; flow rate 2 ml/min; eluents A: 0.1% TFA in $H_2O$, B $CH_3CN$; gradient based on B: 1% to 91% (7').

| Abbreviation | Meaning |
| --- | --- |
| Ac | Acetyl |
| Boc | tert-butyloxycarbonyl |
| br | Broad |
| c- | cyclo- |
| CI | chemical ionisation |
| d | doublet |
| DAD | Diode array detector |
| dd | doublet of doublet |
| DCM | dichloromethane |
| DIPEA | N,N-diisopropylethyl amine |
| DMF | N,N-dimethylformamide |
| DMSO | dimethyl sulphoxide |
| eq. | Equivalent |
| ESI | electrospray ionisation |
| GP | general procedure |
| HPLC | high performance liquid chromatography |
| LC-MS | liquid chromatography mass spectrometry |
| m | Multiplet |
| mc | centred multiplet |
| mCPBA | meta-chloroperbenzoic acid |
| MS | mass spectrometry |
| NMR | nuclear magnetic resonance spectroscopy: chemical shifts (δ) are given in ppm. |
| Ns | nitrophenylsulfonyl- |
| OTf | trifluoromethylsulfonyl- |
| 1-PrOH | 1-propanol |
| q | Quartet |
| rf | at reflux |
| r.t. or rt | room temperature |
| s | Singlet |
| sept. | Septet |
| t | Triplet |
| TBAF | tetrabutylammonium fluoride |
| TEA | Triethylamine |
| TFA | trifluoroacetic acid |
| THF | tetrahydrofuran |
| TMS | trimethylsilyl- |
| $t_R$ | Retention time |
| Ts | toluenesulfonyl- |
| UV | ultraviolet |

The following schemes and general procedures illustrate general synthetic routes to the compounds of general formula I of the invention and are not intended to be limiting. The order of transformations as exemplified in Schemes 1 to 6 can be modified in various ways as it is obvious to the person skilled in the art. The order of transformations exemplified in Schemes 1 to 6 is therefore not intended to be limiting. More particularly, it is possible to combine single steps of the general processes described below in different ways than exemplified in order to prepare intermediates and compounds of the present invention. These alternative combinations of general processes and/or chemical transformations comprising those are therefore intended to be included into the scope of this invention. In addition, interconversion of substituents, for example of residues $R^1$, $R^2$, $R^3$, $R^4$, $R^5$, $R^6$, $R^7$ and $R^8$ can be achieved before and/or after the exemplified transformations. These modifications can be such as, but not limited to, the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis, 3rd* edition, Wiley 1999).

One of the most important methods for the preparation of sulfoximines is the reaction of a sulfoxide with hydrazoic acid, which is generated in situ e.g. from the reaction of sodium azide and conc. sulfuric acid (M. Reggelin, C. Zur, *Synthesis* 2000, 1, 1). The reaction can be performed in an organic solvent, such as chloroform. Further methods for the synthesis of sulfoximines are for example the reaction of sulfoxides with a) $TsN_3$ ((a) R. Tanaka, K. Yamabe, *Chem. Commun.* 1983, 329; (b) H. Kwart, A. A. Kahn, *J. Am. Chem. Soc.* 1967, 89, 1959)).

b) N-tosylimino phenyl iodinane and catalytic amounts of Cu(I) triflate (J. F. K. Müller, P. Vogt, *Tetrahedron Lett.* 1998, 39, 4805).

c) Boc-azide and catalytic amounts of iron(II) chloride (T. Bach, C. Korber, *Tetrahedron Lett.* 1998, 39, 5015).

d) o-Mesitylensulfonylhydroxylamine (MSH) (C. R. Johnson, R. A. Kirchhoff, H. G. Corkins, *J. Org. Chem.* 1974, 39, 2458).

e) [N-(2-(trimethylsilyl)ethanesulfonyl)imino]phenyliodinane (PhI=NSes) (S. Cren, T. C. Kinahan, C. L. Skinner and H. Tye, *Tetrahedron Lett.* 2002, 43, 2749).

f) Trifluoracetamide or sulfonylamides in combination with iodobenzene diacetate, magnesium oxide and catalytic amounts of rhodium(II) acetate dimer (H. Okamura, C. Bolm, *Organic Letters* 2004, 6, 1305.

g) Sulfonylamides in combination with iodobenzene diacetate and catalytic amounts of a chelating ligand and silver salts (G. Y. Cho, C. Bolm, *Org. Lett.* 2005, 7, 4983).

h) $NsNH_2$ and iodobenzene diacetate (G. Y. Cho, C. Bolm, *Tetrahedron Lett.* 2005, 46, 8007).

As regards structure and configuration, sulfoximines as a rule are highly stable (C. Bolm, J. P. Hildebrand, *J. Org. Chem.* 2000, 65, 169). These properties of the functional group often allow even drastic reaction conditions and enable the simple derivatization of the sulfoximines on the imine nitrogen and the α-carbon. Enantiomerically pure sulfoximines are also used as auxiliaries in diastereoselective synthesis ((a) S. G. Pyne, *Sulphur Reports* 1992, 12, 57; (b) C. R. Johnson, *Aldrichchimica Acta* 1985, 18, 3). The preparation of enantiomerically pure sulfoximines can be accomplished for example via racemate separation with enantiomerically pure camphor-10-sulfonic acid ((a) C. R. Johnson, C. W. Schroeck, *J. Am. Chem. Soc.* 1973, 95, 7418; (b) C. S. Shiner, A. H. Berks, *J. Org. Chem.* 1988, 53, 5543) or via racemate separation by chiral HPLC. A further method for the preparation of optically active sulfoximines consists in the stereoselective imination of optically active sulfoxides ((a) C. Bolm, P. Müller, K. Harms, *Acta Chem. Scand.* 1996, 50, 305; (b) Y. Tamura, J. Minamikawa, K. Sumoto, S. Fujii, M. Ikeda, *J. Org. Chem.* 1973, 38, 1239; (c) (H. Okamura, C. Bolm, *Organic Letters* 2004, 6, 1305).

Scheme 1

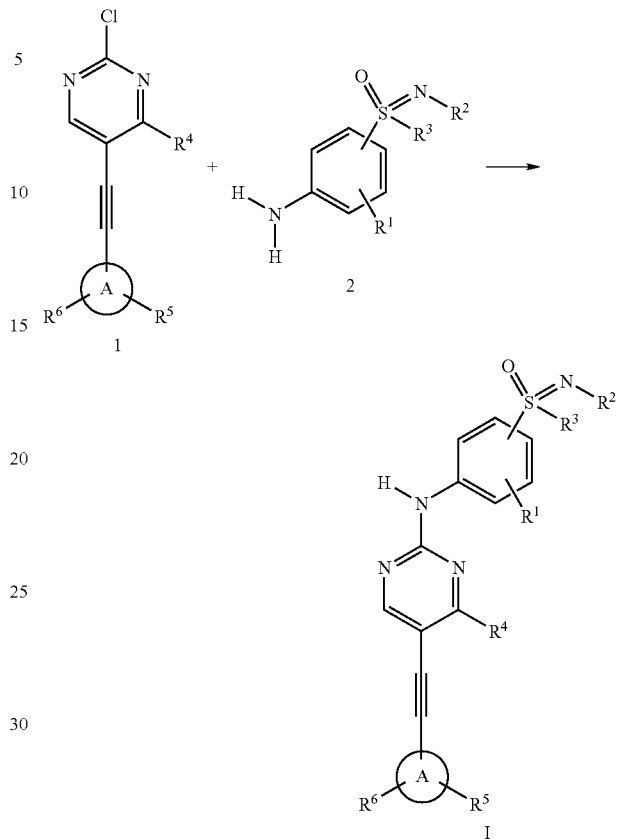

General preparation of compounds of the present invention of general formula I by coupling of a 2-chloropyrimidine of general formula 1 with an aniline of general formula 2, in which $R^1$, $R^2$, $R^3$, $R^4$, $R^5$, $R^6$ and A are as defined in the claims and description of this invention.

According to Scheme 1,2-chloropyrimidines of general formula 1 and anilines of formula 2 can be reacted, for example under acidic conditions, to give compounds of the present invention 1. As acid, for example, hydrogen chloride is suitable. Various solvents or solvent mixtures can be used. Particularly suitable, for example, is the use of acetonitrile or acetonitrile/water mixtures. The reaction temperature can be varied in the range from room temperature to reflux depending on the reactivity of the compounds 1 and 2, and of the acid used and of the solvent used. For acetonitrile and acetonitrile/water mixtures in combination with hydrogen chloride as acid, the temperature range from 60-90° C. is particularly suitable.

Scheme 2

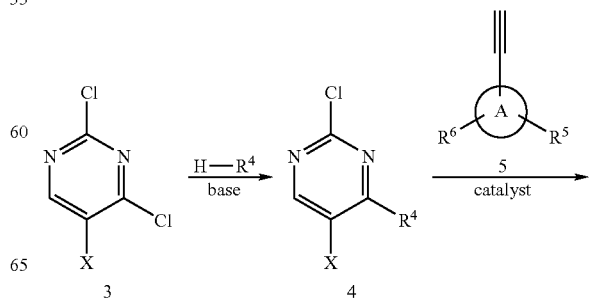

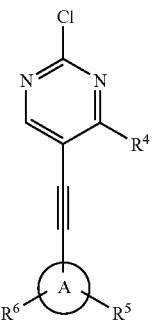

General preparation of interediates of general formula 1 by nucleophilic addition of H—R⁴ groups to 5-halo-2, 4-dichloropyrimidines of general formula 3 and subsequent Sonogashira couplings with alkynes of general formula 5, in which X is Br or I and R¹, R², R³, R⁴, R⁵, R⁶ and A are as defined in the claims and description of this invention with the restriction that R⁴ ≠ H.

5-bromo-2,4-dichloropyrimidine or 2,4-dichloro-5-iodopyrimidine (3) can be converted to compounds of general formula 4 (with R⁴≠H) by reaction with nucleophiles of the type H-R⁴ under basic conditions (see e.g.: a) U. Lücking, M. Krüger, R. Jautelat, G. Siemeister, WO 2005037800; b) U. Lücking, M. Krueger, R. Jautelat, O. Prien, G. Siemeister, A. Ernst, WO 2003076437; c) T. Brumby, R. Jautelat, O. Prien, M. Schäfer, G. Siemeister, U. Lücking, C. Huwe, WO 2002096888). For N-nucleophiles (R⁴=—NR⁷R⁸), acetonitrile is particularly suitable as the solvent and triethylamine as the base. The reaction preferably takes place at room temperature. For O-nucleophiles (R⁴=—OR⁷), THF is particularly suitable as the solvent and sodium hydride as the base. The reaction preferably takes place at 0° C. to room temperature. For S-nucleophiles (R⁴=—SR⁷), acetonitrile is particularly suitable as the solvent and triethylamine as the base. The reaction preferably takes place at −20° C. to room temperature.

The derivatives of the general formula 4 can then, for example, be reacted to give compounds of formula 1 by metal-catalyzed coupling reactions with respectively substituted alkynes of general formula 5. More particularly, compounds of formula 1 can be prepared from intermediates of formula 4 by Pd-catalyzed Sonogashira coupling and Sonogashira-type coupling reactions (including Stephens-Castro couplings and Heck alkynylations) with alkynes of formula 5. Alternatively, halo intermediates of formula 4 can be coupled with trialkylsilyl-protected alkynes of general formula 5' (see Scheme 3) to yield compounds of general formula 1 under conditions which are for example exemplified below. Transition metal-catalyzed couplings of (hetero)aryl halides with alkynes and trialkylsilyl alkynes are well known to the person skilled in the art (see for example (a) Chinchilla, R.; Najera, C. *Chem. Rev.* 2007, 107, 874; (b) Negishi, E.-i., Anastasia, L. *Chem. Rev.* 2003, 103, 1979; see also: (c) *Eur. J. Org. Chem.* 2005, 20, 4256; (d) *J. Org. Chem.* 2006, 71, 2535 and references therein; (e) *Chem. Commun.* 2004, 17, 1934). In the so called Sonogashira coupling, reaction of terminal alkynes with (hetero)aryl halides is triggered by catalytic amounts of a Pd salt in the presence of a copper salt and a base. Various Pd-catalyst/co-catalyst/ligand/base/solvent combinations have been published in the scientific literature which allow a fine-tuning of the required reaction conditions in order to allow for a broad set of additional functional groups on both coupling partners (see references in the above cited reviews). Additionally, recently developed procedures employing e.g. zinc acetylides, alkinyl magnesium salts or alkinyl trifluoroborate salts further broaden the scope of this process.

Alternatively to the coupling with functionalized (hetero) aryl alkynes of general formula 5, halides of formula 4 can be coupled first to mono-protected acetylene, such as, for example, to TMS-acetylene, under conditions as described before. Cleavage of the protecting group under conditions known to the person skilled in the art, such as, for example treatment with TBAF or K₂CO₃/MeOH in the case of a TMS protecting group, allows for a subsequent second coupling reaction of the so formed alkyne to a (hetero)aryl halide under conditions as described before hence giving rise to compounds of the present invention. Alternatively to the coupling of halides of general formula 4 with protected acetylene and subsequent deprotection, pyrimidines with a —C≡C—H substituent at the 5 position are accessible, for example, from the respective C5-carbaldehydes by various C1-homologation procedures as known to the person skilled in the art (see below).

Intermediates of formula 1 (Scheme 2) with R⁴=H are directly accessible from 5-halo-2-chloropyrimidines by Sonogashira and Sonogashira-type couplings as described before. 5-Halo-2,4-chloropyrimidines and 5-halo-2-chloropyrimidines are accessible e.g. from 5-halouracils or 4-desoxy-5-halouracils by reaction with, for example, POCl₃.

Scheme 3

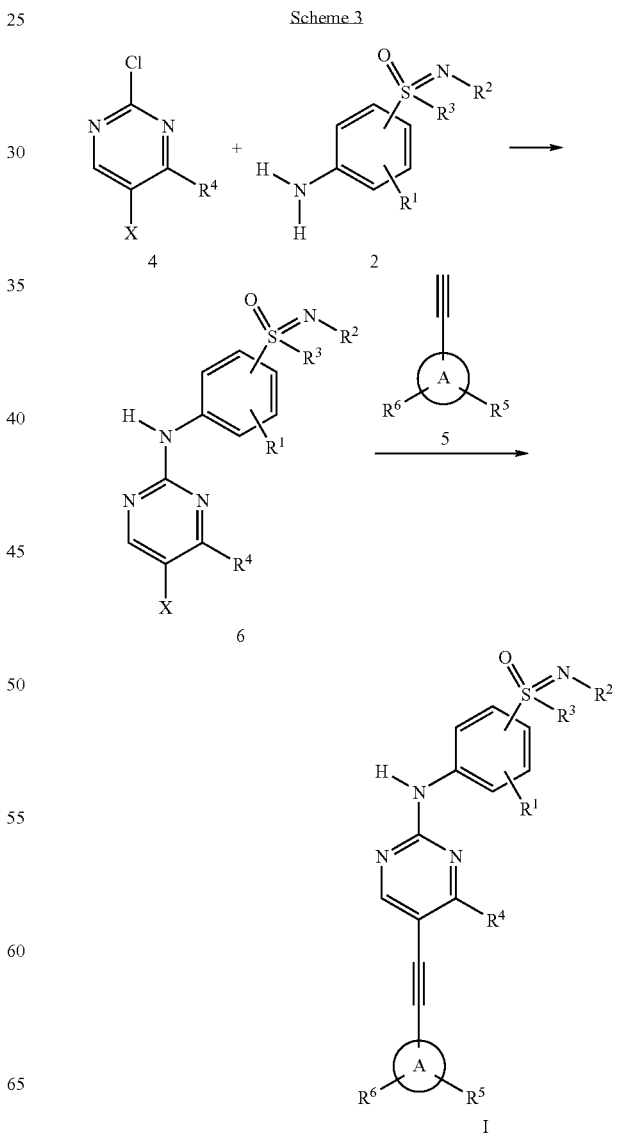

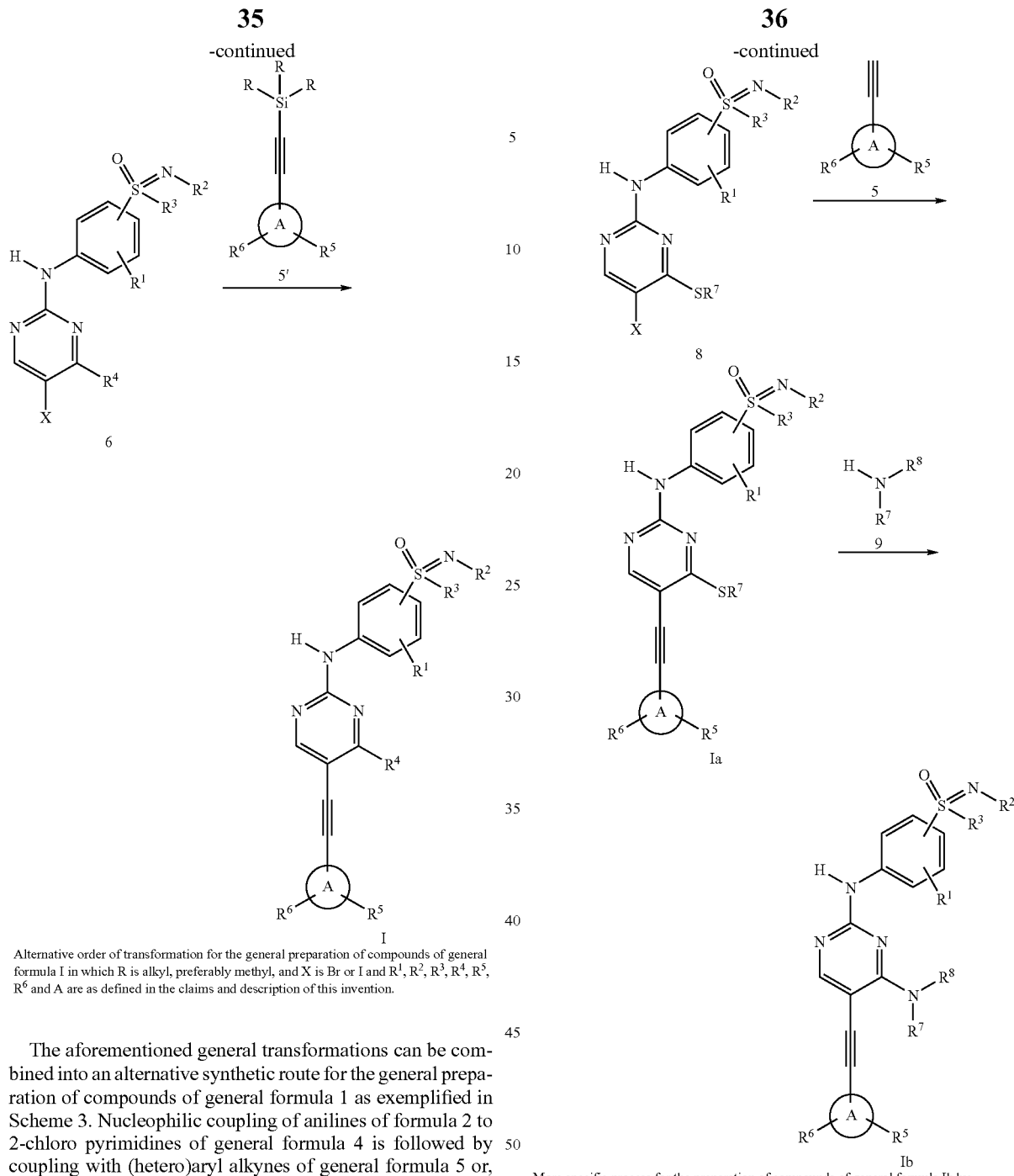

Alternative order of transformation for the general preparation of compounds of general formula I in which R is alkyl, preferably methyl, and X is Br or I and $R^1$, $R^2$, $R^3$, $R^4$, $R^5$, $R^6$ and A are as defined in the claims and description of this invention.

The aforementioned general transformations can be combined into an alternative synthetic route for the general preparation of compounds of general formula 1 as exemplified in Scheme 3. Nucleophilic coupling of anilines of formula 2 to 2-chloro pyrimidines of general formula 4 is followed by coupling with (hetero)aryl alkynes of general formula 5 or, alternatively, with trialkylsilyl-protected derivatives thereof, preferably with trimethylsilyl protected alkynes of general formula 5', employing conditions as described before.

Scheme 4

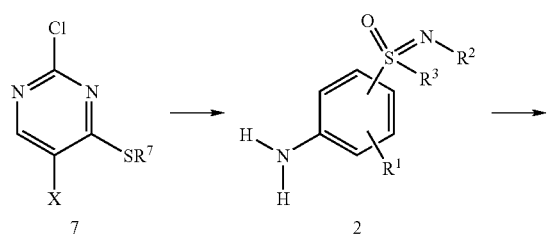

More specific process for the preparation of compounds of general formula Ib by replacement of $SR^7$-substituents by $NR^7R^8$-substituents under oxidative conditions, in which X is Br or I and $R^1$, $R^2$, $R^3$, $R^4$, $R^5$, $R^6$, $R^7$, $R^8$ and A are as defined in the claims and description of this invention.

A more specific process for the preparation of compounds of formula Ib is exemplified in Scheme 4, in which pyrimidines of general formula 7, which carry a $SR^7$-substituent at the C4 position, are coupled with anilines of general formula 2 and subsequently with (hetero)aryl alkynes of general formula 5 to yield compounds of general formula Ia. Replacement of the $SR^7$-substituent at C4 by amine side chains can be accomplished under oxidative conditions, for example by treating with an oxidating agent such as, for example, mCPBA, via intermediate sulfoxide/sulfone formation, in the presence of amines of general formula 9 to yield compounds of general formula Ib.

Scheme 5

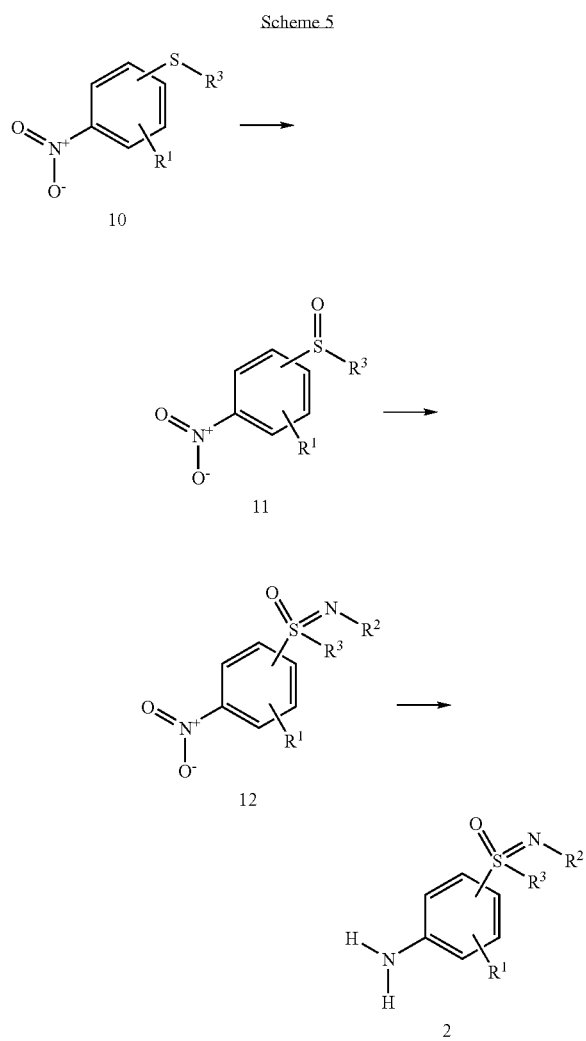

General process for the preparation of compounds of general formula 2 by oxidation of sulfides of general formula 10 to sulfoxides of general formula 11, subsequent transformation into sulfoximines of general formula 12 and nitro reduction to yield anilines of general formula 2, in which $R^1$, $R^2$, and $R^3$ are as defined in the claims and description of this invention.

Anilines of general formula 2 (to be used in the aforementioned general processes for the preparation of the compounds of the present invention) are accessible, for example, from sulfides of general formula 10 by oxidation to sulfoxides of general formula 11, subsequent transformation into sulfoximines of general formula 12 and nitro reduction (see Scheme 5).

For the conversion of a thioether into a sulfoxide, many methods are available (see e.g.: a) M. H. Ali, W. C. Stevens, Synthesis 1997, 764; b) I. Fernandez, N. Khiar, Chem. Rev. 2003, 103, 3651). Particularly suitable for the preparation of compounds of general formula 11 is the use of periodic acid/iron(III) chloride. For the transformation of sulfoxides into sulfoximines (e.g. 11→12) various conditions are known to the person skilled in the art (see above for specific references). These procedures allow for the synthesis of either free ($R^2$=H) or substituted ($R^2$≠H) sulfoximines. In the latter case, the $R^2$ group as introduced in the sulfoximine formation process can subsequently be removed or transformed into a different $R^2$ group. Free sulfoximines ($R^2$=H) can be further functionalized by various general methods, including the following specific transformations:

a) Alkylation (see e.g.: C. R. Johnson, J. Org. Chem. 1993, 58, 1922-1923); [for reductive alkylations, see b) b)].

b) Acylation (see e.g.: a) C. P. R. Hackenberger, G. Raabe, C. Bolm, Chem. Europ. J. 2004, 10, 2942-2952; b) C. Bolm, C. P. R. Hackenberger, O. Simic, M. Verrucci, D. Müller, F. Bienewald, Synthesis 2002, 7, 879-887; c) C. Bolm, G. Moll, J. D. Kahmann, Chem. Europ. J. 2001, 7, 1118-1128).

c) Arylation (see e.g.: a) C. Bolm, J. P. Hildebrand, Tetrahedron Lett. 1998, 39, 5731-5734; b) C. Bolm, J. P. Hildebrand, J. Org. Chem. 2000, 65, 169-175; c) C. Bolm, J. P. Hildebrand, J. Rudolph, Synthesis 2000, 7, 911-913; d) Y. C. Gae, H. Okamura, C. Bolm, J. Org. Chem. 2005, 70, 2346-2349).

d) Reaction with isocyanates/isothiocyanates (see e.g.: a) V. J. Bauer, W. J. Fanshawe, S. R. Safir, J. Org. Chem. 1966, 31, 3440-3441; b) C. R. Johnson, M. Haake, C. W. Schroeck, J. Am. Chem. Soc. 1970, 92, 6594-6598; c) S. Allenmark, L. Nielsen, W. H. Pirkle, Acta Chem. Scand. Ser. B 1983, 325-328)

e) Reaction with sulphonyl chlorides (see e.g.: a) D. J. Cram, J. Day, D. R. Rayner, D. M von Schriltz, D. J. Duchamp, D. C. Garwood. J. Am. Chem. Soc. 1970, 92, 7369-7384), b) C. R. Johnson, H. G. Corkins, J. Org. Chem. 1978, 43, 4136-4140; c) D. Craig, N. J. Geach, C. J. Pearson, A. M. Z. Slawin, A. J. P. White, D. J. Williams, Tetrahedron 1995, 51, 6071-6098).

f) Reaction with chloroformates or anhydrides (see e.g.: a) D. J. Cram, J. Day, D. R. Rayner, D. M von Schriltz, D. J. Duchamp, D. C. Garwood. J. Am. Chem. Soc. 1970, 92, 7369-7384), b) S. G. Pyne, Z. Dong, B. W. Skelton, A. H. Allan, J. Chem. Soc. Chem. Commun. 1994, 6, 751-752; c) C. R. Johnson, H. G. Corkins, J. Org. Chem. 1978, 43, 4136-4140; d) Y. C. Gae, H. Okamura, C. Bolm, J. Org. Chem. 2005, 2346-2349).

g) Silylation: (see e.g.: A. J. Pearson, S. L. Blystone, H. Nar, A. A. Pinkerton, B. A. Roden, J. Yoon, J. Am. Chem. Soc. 1989, 111, 134-144).

For the subsequent reduction of the aromatic nitro group in compounds of general formula 12 to give compounds of general formula 2 a range of reaction conditions is available (see e.g.: R. C. Larock, Comprehensive Organic Transformations, VCH, New York, 1989, 411-415). Particularly suitable is the use of titanium(III) chloride or iron as reducing agent. The preparation of compounds of general formula 2 is also described in U. Lücking, M. Krüger, R. Jautelat, G. Siemeister, WO 2005037800, which is hereby included by reference.

In the context of general and specific processes as described in this invention it can be advantageous to intermittently protect a free sulfoximine [with $R^2$=H] by transformation into a alkoxycarbonyl-protected sulfoximine [with $R^2$=C(O)OR$^c$] and deprotection after appropriate subsequent functionalizations. Deprotection of alkoxycarbonyl-protected sulfoximines can be accomplished, for example, by treatment with a base, such as, for example, sodium ethoxide, in a suitable solvent such as, for example, ethanol, at a suitable reaction temperature. Particularly suitable is the deprotection of ethoxycarbonyl-protected sulfoximines (with $R^2$=C(O)OEt) by treatment with sodium ethoxide in ethanol under microwave irradiation at a temperature of 100 to 120° C.

Scheme 6

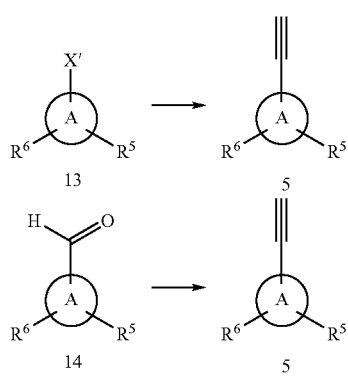

General process for the preparation of compounds of general formula 5 from (hetero)aryl halides of general formula 13 or (hetero)aryl carbaldehydes of general formula 14, in which X' = Cl, Br or I and $R^5$ and $R^6$ are as defined in the claims and description of this invention.

Two general processes for the preparation of alkynes of general formula 5 are exemplified in Scheme 6. (Hetero)aryl halides of general formula 13 can be reacted with appropriately mono-protected acetylenes under Sonogashira-type conditions as described above and subsequently deprotected to yield compounds of general formula 5. Particularly suited mono-protected acetylenes for this process are TMS-protected acetylene and 2-methyl-but-3-yn-2-ol. Cleavage of the respective protecting group can be accomplished, for example, by treatment with TBAF or $K_2CO_3$ in the case of the use of TMS-acetylene, or by treatment with base in the case of the use of 2-methyl-but-3-yn-2-ol. It should be noted that, as described supra, trialkylsilyl-protected alkynes can be used directly in Sonogashira-type couplings by employing, for example, TBAF as base. Alternatively, compounds of general formula 5 are accessible form their respective carbaldehydes of general formula 14 by, for example, (a) Corey-Fuchs homologation (*Tetrahedron Lett.* 1972, 14, 3769), (b) reaction with TMS-diazomethane (*Chem. Comm.* 1973, 151), (c) reaction with the Gilbert-Seyferth reagent (*J. Org. Chem.* 1971, 36, 1379; *J. Org. Chem.* 1996, 61, 2540) or (d) reaction with the Ohira-Bestmann diazophosphono ester (*Synth. Commun.* 1989, 19, 561; *Synlett* 1996, 521).

In the subsequent paragraphs general procedures for the synthesis of the below mentioned intermediates and specific example compounds are summarised.

GENERAL PROCEDURES

General Procedure 1 (GP1)

Preparation of 5-bromo-2,4-dichloro-pyrimidine or 2,4-dichloro-5-iodo-pyrimidine 5-bromo- or 5-iodouracil (1.0 equiv.) is suspended in N,N-dimethylaniline, treated with phosphorus oxychloride (10.0 equiv.) and stirred for 90 minutes at 125° C. After cooling to room temperature, excess phosphorus oxychloride is removed under vacuum. The residue is poured into ice-water. After 2 hours the crystals that have formed are filtered off and washed with water. Next, the crystals are dissolved in ethyl acetate. The organic phase is washed with saturated sodium hydrogen carbonate solution and saturated sodium sulfite solution and dried over sodium sulfate. After removal of the solvent, optionally chromatographic purification is performed.

5-bromo-2,4-dichloro-pyrimidine is commercially available (e.g.: Aldrich, Acros, Frontier). 2,4-dichloro-5-iodo-pyrimidine is likewise commercially available (Apin).

General Procedure 2 (GP2)

Couplings of amines to the 4-position of 2,4-dichloropyrimidines 5-bromo-2,4-dichloro-pyrimidine or 2,4-dichloro-5-iodo-pyrimidine (1.0 equiv.) is dissolved in acetonitrile (62.0 equiv.) and treated with triethylamine (1.2 equiv.) and the amine component (1.1 equiv.). After 24 hours at room temperature, the mixture is diluted with ethyl acetate. The organic phase is washed with saturated sodium chloride solution, 10% aqueous citric acid solution and saturated sodium hydrogen carbonate solution. After drying over sodium sulfate and removal of the solvent, purification is effected in general by chromatography.

The reaction of 5-bromo-2,4-dichloro-pyrimidine or 2,4-dichloro-5-iodo-pyrimidine with amines, alcohols or thiols is also described in: a) U. Lücking, M. Krüger, R. Jautelat, G. Siemeister, WO 2005037800; b) U. Lücking, M. Krueger, R. Jautelat, O. Prien, G. Siemeister, A. Ernst, WO 2003076437; c) T. Brumby, R. Jautelat, O. Prien, M. Schäfer, G. Siemeister, U. Lücking, C. Huwe, WO 2002096888).

General Procedure 3a (GP3a)

Introduction of Alcohols in the 4 Position of the Pyrimidine 5-bromo-2,4-dichloro-pyrimidine or 2,4-dichloro-5-iodo-pyrimidine (1.0 equiv.) is dissolved in dry methanol (85 equiv.) and added dropwise with stirring at −5 to 0° C. to methanolic sodium ethanolate solution (1.05 equiv., 0.3 M). The reaction is warmed to RT and stirred for 18 hrs. The crude product usually precipitates from the solution and can optionally be recrystallized from, for example, methanol.

General Procedure 3b (GP3b)

Introduction of Alcohols in the 4 Position of the Pyrimidine

A stirred solution of 5-bromo-2,4-dichloro-pyrimidine or 2,4-dichloro-5-iodo-pyrimidine (1.0 eq) in dry acetonitrile (0.4 M) is treated at rt with a (preferably freshly prepared) suspension of sodium-alcoholate (1.05 eq) (from the corresponding alcohol (1.05 eq) and 60% w NaH (1.05 eq) in dry diethyl ether (0.11 M)). The reaction mixture is stirred overnight. Then the reaction mixture is poured into water and extracted with ethyl acetate (5 times). The combined extracts are dried over anhydrous sodium sulfate, filtered and concentrated in vacuo. The residue is optionally purified by flash chromatography.

General Procedure 4 (GP4)

Coupling of Anilines to 2-chloropyrimidines

The respective 2-chloropyrimidine (1 eq.) and the respective aniline (1.05 eq.) are dissolved in wet (10%) acetonitrile (~0.3 M), treated with 5N HCl/dioxane solution (~0.2 mL per mmol 2-chloropyrimidine), heated to 50° C. and stirred at this temperature until TLC indicates complete turnover. Then the reaction mixture is poured into aq. NaHCO₃ solution (with 0.5 g Na$_2$SO$_3$ added per 1 L NaHCO$_3$ solution). The mixture is extracted with EtOAc or CHCl$_3$, the combined organic layers are dried and evaporated to dryness. The analytically pure coupling products can be isolated, for example, by crystallization from acetonitrile or preparative HPLC purification.

General Procedure 5 (GP5)

Reduction of Nitroarenes or Nitro-Heteroarenes with Activated Iron

The respective nitro compound (1.0 eq) is added to a stirred mixture of powdered iron (12 eq) in 85% ethanol (5 mL per mmol nitro compound) and concentrated hydrochloric acid (10 μL per mmol nitro compound) at room temperature. Subsequently, the mixture is stirred at 60° C. until all starting material is consumed (typically after about 3 h). After cooling to room temperature, the mixture is filtered, and the filter cake is repeatedly washed with hot ethanol. The filtrate is evaporated and the residue can be further purified by column chromatography to give the desired amine.

General Procedure 6a (GP6a)

Cleavage of Ethoxycarbonyl Group (Method A)

The respective N-ethoxycarbonyl sulfoximine (1 eq.) is dissolved in EtOH (8-16 mL per mmol sulfoximine) and treated with 3-4 eq. of NaOEt solution (20% in EtOH). The resulting mixture is stirred at reflux until TLC indicates complete turnover (usually after 4-6 hours). The reaction mixture is concentrated, the residue dissolved in DCM and quenched with water. The aqueous layer is extracted with DCM, the combined organic layers are washed with brine, dried and concentrated in vacuo. Flash column chromatography optionally followed by trituration or preparative HPLC purification can be used to yield the analytically pure target compound.

General Procedure 6b (GP6b)

Cleavage of Ethoxycarbonyl Group (Method B)

The respective N-ethoxycarbonyl sulfoximine (1 eq.) is dissolved in EtOH (8-16 mL per mmol sulfoximine) and treated with 3-4 eq. of NaOEt solution (20% in EtOH). The resulting mixture is then subjected to focussed microwave irradiation (Biotage Initiator 2.0) to maintain a reaction temperature of 100° C. until the reaction is complete (typically between 15 and 30 minutes). The reaction mixture is concentrated and the residue is triturated with water. The precipitated solid is isolated by filtration and dried in vacuo and can optionally be further purified by flash column chromatography, optionally followed by trituration or preparative HPLC purification, to give the analytically pure target compound.

General Procedure 7 (GP7)

In Situ Sulfide Oxidation—Amine Displacement

To a solution of the respective pyrimidin-4-yl thioether (1 eq.) in N-methylpyrrolidin-2-one (0.1 M) is added meta-chloroperbenzoic acid (1.1-1.5 eq.) and the mixture is stirred for 1-2 h at room temperature. Subsequently, triethylamine (2.5-5.0 eq.) and the respective nucleophile, e.g. an amine is added and the mixture is stirred at 50-90° C. The reaction is monitored by TLC and is typically completed within 3 to 6 hours. After cooling to room temperature, water is added and the mixture is extracted with ethyl acetate. The combined organic layers are washed with brine, dried, and concentrated in vacuo. The crude products are purified by flash column chromatography, optionally followed by recrystallisation from a suitable solvent, for example, from diethyl ether.

General Procedure 8a (GP8a)

Sonogashira Coupling (Conditions A)

One equivalent of the halopyrimidine intermediate, CuI (0.2 eq.) and Pd(PPh$_3$)$_2$Cl$_2$ (0.1 eq.) are weighed into a Schlenk flask, set under an atmosphere of argon and dissolved in dry DMF (1 mL per mmol halide). The respective ethynyl (hetero)aryl compound (1.2 eq.) and triethylamine (5-10 eq.) are added sequentially and the resulting mixture is stirred at rt (unless otherwise noted) until TLC or LCMS analysis show complete consumption of the starting halide compound. The reaction mixture is partitioned between DCM and water, the aqueous layer is extracted with DCM (3×) and the combined organic layers are dried and concentrated in vacuo. The target compound is isolated by crystallization and/or flash column chromatography and/or preparative HPLC purification.

General Procedure 8b (GP8b)

Sonogashira Coupling (Conditions B)

PdCl$_2$(PPh$_3$)$_2$ (5-10 mol %) is added to a mixture of the respective halide (1 eq), copper iodide (10-20 mol %), the respective alkyne (1-1.5 eq) in THF doped with triethylamine (2-10 eq). The mixture is heated to reflux in a capped flask for 18 h. After cooling to room temperature, water and ethyl acetate is added and the organic layer is separated, filtered and concentrated in vacuo and purified by HPLC.

General Procedure 8c (GP8c)

Sonogashira Coupling (Conditions c)

To a mixture of the respective halide in THF (5 mL per mmol halide) are added the alkyne (typically 1.5-2.0 eq), PdCl$_2$(PPh$_3$)$_2$ (5-10 mol-%), copper (I) iodide (20 mol-%), and a 1M solution of tetrabutylammonium fluoride in THF (2.0-3.5 eq.) under inert atmosphere at room temperature. The mixture is then allowed to react for 30 min at 80° C. in a microwave oven. After cooling to room temperature, the mixture is diluted with water, and repeatedly extracted with dichloromethane. The combined organic layers are dried over MgSO$_4$ and evaporated. Column chromatography or preparative HPLC yield the pure target compound.

General Procedure 8d (GP8d)

Sonogashira Coupling (Conditions D)

One equivalent of the respective haloarene, CuI (0.05 eq.) and Pd(PPh$_3$)$_2$Cl$_2$ (0.01 eq.) are weighed into a Schlenk flask, set under an atmosphere of argon and dissolved in dry DMF (between 2 and 5 mL per mmol halide). Trimethylsilylacetylene (1.05 eq. unless stated otherwise) and triethylamine (2 eq.) are added sequentially and the resulting mixture is stirred at rt (unless otherwise noted) until TLC or LCMS analysis show complete consumption of the starting halide compound. The reaction mixture is partitioned between DCM and water, the aqueous layer is extracted with DCM (3×) and the combined organic layers are dried and concentrated in vacuo. The target compound is isolated by crystallization and/or flash column chromatography and/or preparative HPLC purification.

General Procedure 9 (GP9)

Desilylation of (trimethyl)silylalkynes

To a solution of the respective (trimethylsilyl)alkyne in THF (approx. 10 mL per g alkyne) is added a 1M solution of tetrabutylammonium fluoride in THF (1.65 eq.), and the resulting mixture is stirred at room temperature until the reaction is completed (typically after approx. 3 h). The product is isolated by dilution with water, extraction with e.g. dichloromethane, and column chromatography (if required).

Preparation of the Sulfoximino-Anilines

Intermediate 1

Preparation of (RS)—S-(4-aminophenyl)-N-(ethoxycarbonyl)-S-methylsulfoximide

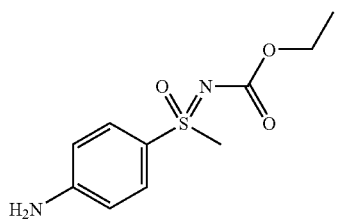 [SMILES: CCOC(=O)N=S(C)(=O)c1ccc(N)cc1]

Step a) Preparation of (RS)-1-(methylsulfinyl)-4-nitrobenzene

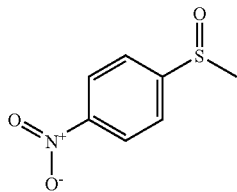

A suspension of 25.0 g (147.8 mmol) 1-methylsulfanyl-4-nitro-benzene and 0.69 g (4.2 mmol) iron(III) chloride (anhydrous) in 120 ml acetonitrile is treated with 36.0 g (158.1 mmol) periodic acid and stirred at room temperature. At the start of heat evolution, the mixture is transiently cooled with an ice-bath, so that the temperature does not rise above 30° C. After the heat evolution has subsided, the mixture is stirred at room temperature for a further 10 mins. The mixture is poured into a solution of 150 g sodium thiosulphate in 1000 ml ice-water and then extracted with DCM. The combined organic phases are washed with saturated NaCl solution, dried (Na$_2$SO$_4$), filtered and concentrated. The remaining residue is recrystallised from toluene. 23.6 g (128.0 mmol, corresponding to 86% of theor.) of the product is obtained.

$^1$H-NMR (DMSO): 8.41 (m, 2H), 7.97 (m, 2H), 2.86 (s, 3H).

ES: 186 (ES).

Step b) Preparation of (RS)—S-(4-nitrophenyl)-S-methylsulfoximide 23.65 g (127.7 mmol) (RS)-1-(methylsulfinyl)-4-nitrobenzene in 130 ml chloroform are treated with 9.32 g (143.4 mmol) sodium azide. The mixture is slowly treated with 32.4 ml of concentrated sulfuric acid at 0° C. and then slowly heated to 45° C. After 16 hrs, the mixture is cooled to room temperature, treated with ice-water and extracted with chloroform. This organic phase is discarded. The aqueous phase is basified with 2N NaOH solution and extracted with DCM. The combined organic phases are washed with saturated NaCl solution, dried (Na$_2$SO$_4$), filtered and concentrated. 17.17 g (88.4 mmol, corresponding to 63% of theor.) of the product is obtained.

$^1$H-NMR (DMSO): 8.43 (m, 2H), 8.17 (m, 2H), 4.62 (s, 1H), 3.18 (s, 3H).

ES: 201 (ES).

Step c) Preparation of (RS)—N-(ethoxycarbonyl)-S-methyl-S-(4-nitrophenyl)-sulfoximide 8.50 g (4.5 mmol) (RS)—S-(4-nitrophenyl)-S-methylsulfoximide in 400 ml pyridine are treated dropwise at room temperature with 18.8 ml (197.2 mmol) ethyl chloroformate. The mixture is stirred at room temperature for 4 hours and then poured into dilute NaCl solution. It is extracted with ethyl acetate. The combined organic phases are dried (Na$_2$SO$_4$), filtered and concentrated. The remaining residue is chromatographically purified (hexane/ethyl acetate 1:1). 8.94 g (32.8 mmol, corresponding to 77% of theor.) of the product is obtained.

$^1$H-NMR (DMSO-D6): 8.49 (m, 2H), 8.22 (m, 2H), 3.90 (m, 2H), 3.56 (s, 3H), 1.10 (tr, 3H).

Step d) Preparation of (RS)—S-(4-aminophenyl)-N-(ethoxycarbonyl)-S-methyl-sulfoximide

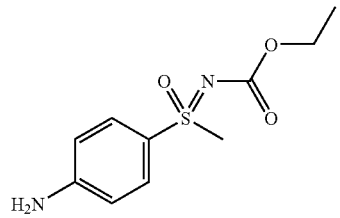 [SMILES: CCOC(=O)N=S(C)(=O)c1ccc(N)cc1]

A solution of 8.70 g (32.0 mmol) (RS)—N-(ethoxycarbonyl)-S-methyl-S-(4-nitro-phenyl)sulfoximide in 650 ml THF is slowly treated at room temperature with 435 ml of a 10% solution of Ti(III)Cl$_3$ in approximately 10% hydrochloric acid (Aldrich). The mixture is stirred at room temperature for 4 hours and then cooled to 0° C. 450 ml of a 32% NaOH solution are added dropwise. During this, the reaction mixture is periodically diluted by the addition of water and ethyl acetate. It is treated with 500 ml ethyl acetate and the organic phase is separated. The mushy aqueous phase is extracted with ethyl acetate. The combined organic phases are washed with dilute NaCl solution, dried (Na$_2$SO$_4$), filtered and concentrated. 8.05 g (ca. 32.0 mmol) of the product is obtained, which is used without further purification.

$^1$H-NMR (DMSO-D6): 7.52 (m, 2H), 6.66 (m, 2H), 6.17 (s, 2H), 3.91 (q, 2H), 3.30 (s, 3H), 1.12 (tr, 3H).

Intermediate 2

Preparation of (RS)—S-(4-aminophenyl)-N-(ethoxycarbonyl)-S-ethylsulfoximide

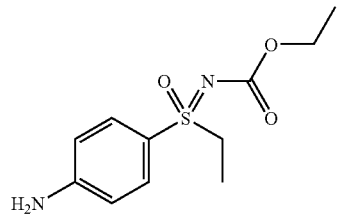 [SMILES: CCOC(=O)N=S(=O)(CC)c1ccc(N)cc1]

Step a) Preparation of (RS)-1-(ethylsulfinyl)-4-nitrobenzene

Preparation analogously to Intermediate 1—step a

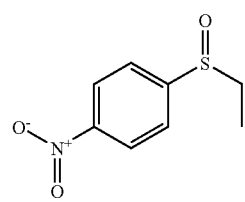

$^1$H-NMR (DMSO): 8.39 (m, 2H), 7.91 (m, 2H), 3.18 (m, 1H), 2.88 (m, 1H), 1.06 (tr, 3H).

Step b) Preparation of (RS)—S-(4-nitrophenyl)-S-ethylsulfoximide

Preparation analogously to Intermediate 1—step b

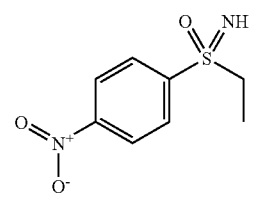

$^1$H-NMR (DMSO-D6): 8.42 (m, 2H), 8.13 (m, 2H), 4.59 (s, 1H), 3.23 (q, 2H), 1.10 (t, 3H).

Step c) Preparation of (RS)—N-(ethoxycarbonyl)-S-ethyl-S-(4-nitrophenyl)-sulfoximide Preparation analogously to Intermediate 1—step c

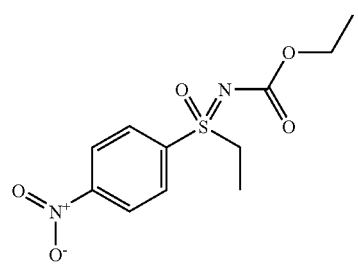 [SMILES: CCOC(=O)N=S(=O)(CC)c1ccc([N+](=O)[O-])cc1]

$^1$H-NMR (DMSO-D6): 8.48 (m, 2H), 8.15 (m, 2H), 3.92 (m, 2H), 3.69 (m, 2H), 1.12 (m, 6H).

Step d) Preparation of (RS)—S-(4-aminophenyl)-N-(ethoxycarbonyl)-S-ethyl-sulfoximide Preparation analogously to Intermediate 1—step d

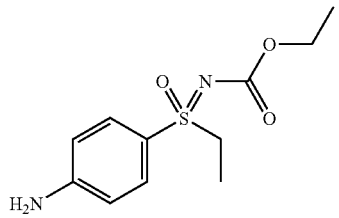 [SMILES: CCOC(=O)N=S(=O)(CC)c1ccc(N)cc1]

$^1$H-NMR (DMSO-D6): 7.47 (m, 2H), 6.67 (m, 2H), 6.20 (s, 2H), 3.90 (m, 2H), 3.42 (q, 2H), 1.10 (m, 6H).

Intermediate 3

Preparation of (RS)—S-(4-aminophenyl)-N-(ethoxycarbonyl)-S-cyclopropyl-sulfoximide

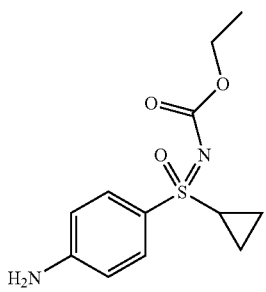 [SMILES: CCOC(=O)N=S(=O)(c1ccc(N)cc1)C1CC1]

Step a) Preparation of (RS)-1-(cyclopropylsulfinyl)-4-nitrobenzene

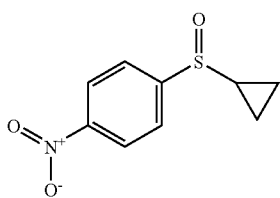 [SMILES: O=[N+]([O-])c1ccc(S(=O)C2CC2)cc1]

This compound was prepared as described in WO 2005/37800 on page 103.

Step b) Preparation of (RS)—S-(4-nitrophenyl)-S-cyclopropylsulfoximide

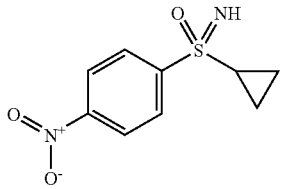 [SMILES: N=S(=O)(c1ccc([N+](=O)[O-])cc1)C1CC1]

6.6 g (31.24 mmol) (RS)-1-(cyclopropylsulfinyl)-4-nitrobenzene, 7.77 g trifluoroacetamide (68.74 mmol), 16.6 g (51.55 mmol) iodobenzene diacetate and 5.54 g (137.5 mmol) magnesium oxide are placed in 350 ml dichloro-methane. The mixture is stirred for 5 minutes, treated with 0.69 g (1.56 mmol) rhodium(II) acetate dimer and stirred at room temperature for 12 hours. The suspension is diluted with 235 ml methanol, treated with 23.75 g potassium carbonate and stirred at room temperature for 4 hours. Next the mixture is treated with 400 ml water, and the organic phase is separated and filtered at the pump through Celite®. The aqueous phase is extracted several times with dichloromethane. The combined organic phases are washed with half-saturated sodium chloride solution and stirred with 100 ml 2N hydrochloric acid for 30 minutes. The aqueous phase is adjusted to pH 9 with concentrated sodium hydroxide solution with ice cooling. The crystallised product is aspirated dry, washed with water and dried. 4.7 g (66.5% of theor.) of the product is obtained.

$^1$H-NMR (DMSO-D6): 8.41 (m, 2H), 8.15 (m, 2H), 4.65 (s, 1H), 2.78 (m, 1H), 1.15 (m, 1H), 0.98 (m, 3H)

Step c) Preparation of (RS)—N-(ethoxycarbonyl)-S-cyclopropyl-S-(4-nitrophenyl)-sulfoximide Preparation analogously to Intermediate 1—step c

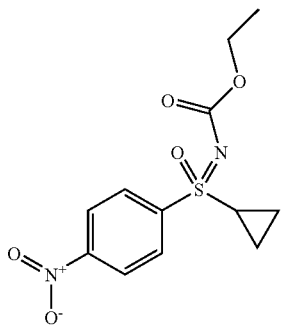 [SMILES: CCOC(=O)N=S(=O)(c1ccc([N+](=O)[O-])cc1)C1CC1]

$^1$H-NMR (DMSO-D6): 8.46 (m, 2H), 8.18 (m, 2H), 3.88 (m, 2H), 3.22 (m, 1H), 1.40 (m, 1H), 1.28 (m, 1H), 1.07 (m, 5H).

Step d) Preparation of (RS)—S-(4-aminophenyl)-N-(ethoxycarbonyl)-S-cyclo-propylsulfoximide Preparation analogously to Intermediate 1—step d

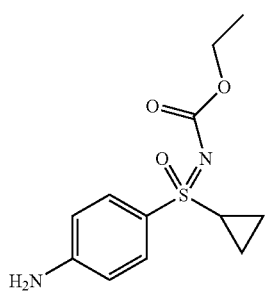 [SMILES: CCOC(=O)N=S(=O)(c1ccc(N)cc1)C1CC1]

$^1$H-NMR (DMSO-D6): 7.45 (m, 2H), 6.66 (m, 2H), 6.16 (s, 2H), 3.87 (m, 2H), 2.86 (m, 1H), 1.19 (m, 1H), 1.11 (m, 1H), 1.08 (t, 3H), 0.93 (m, 2H).

Intermediate 4

Preparation of (R)—S-(4-aminophenyl)-N-(ethoxy-carbonyl)-S-cyclopropyl-sulfoximide

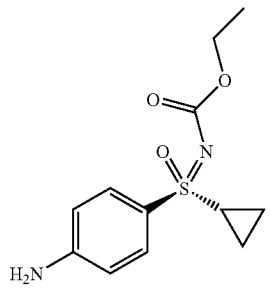 [SMILES: CCOC(=O)N=[S@](=O)(c1ccc(N)cc1)C1CC1]

The enantiomerically pure compounds Intermediate 4 and 5 are obtained by preparative chiral HPLC from the racemic Intermediate 3:

Analytical:
Column: Chiralpak AD-H 5μ 150×4.6 mm
Solvent: hexane/ethanol 80:20
Buffer: —
Gradient: isocratic
Flow: 1.0 mL/min
Solution: 1 mg/mL EtOH
Injection: 20 μl
Detection: PDA 254 nm

| Peak | Retention Time | Area | Comment |
|---|---|---|---|
| 1 | 7.31 | 49.96% | Intermediate 5 |
| 2 | 10.26 | 50.04% | Intermediate 4 |

Preparative:
Column: Chiralpak AD 20μ 250×60 mm
Solvent: hexane/ethanol 80:20
Buffer:
Gradient: isocratic
Flow: 80 mL/min
Solution: 9200 mg/90 ml EtOH
Injection: 15×6000 μl=>1×~610 mg
Reinjection: 30×~200 mg/ml; 16×~200 mg/ml; 8×~200 mg/ml; 4×~200 mg/ml
Detection: UV 254 nm The assignment of the absolute stereochemistry is based on X-ray structural analysis. The second eluting enantiomer possesses the R configuration at the sulphur atom.

$^1$H-NMR (DMSO-D6): identical with Intermediate 3

Intermediate 5

Preparation of (S)—S-(4-aminophenyl)-N-(ethoxy-carbonyl)-S-cyclopropyl-sulfoximide Preparation by Racemate Separation as Described for Intermediate 4

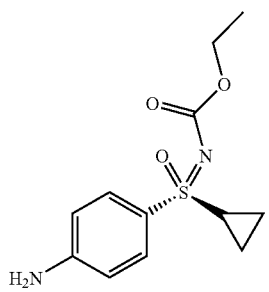 [SMILES: CCOC(=O)N=[S@@](=O)(c1ccc(N)cc1)C1CC1]

$^1$H-NMR (DMSO-D6): identical with Intermediate 3

Intermediate 6

Preparation of (RS)—S-(4-aminophenyl)-N-(ethoxy-carbonyl)-S-phenylsulfoximide

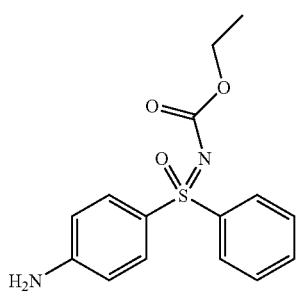 [SMILES: CCOC(=O)N=S(=O)(c1ccccc1)c1ccc(N)cc1]

Step a) Preparation of (RS)-1-(phenylsulphinyl)-4-nitrobenzene

Preparation analogously to Intermediate 1—step a from commercially available (4-nitrophenyl)-phenyl sulphide.

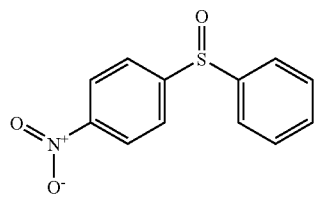 [SMILES: O=[N+]([O-])c1ccc(S(=O)c2ccccc2)cc1]

$^1$H-NMR (DMSO-D6): 8.35 (dm, 2H), 8.01 (dm, 2H), 7.82-7.78 (m, 2H), 7.60-7.52 (m, 3H).

Step b) (RS)—S-(4-nitrophenyl)-S-phenylsulfoximide

Preparation analogously to Intermediate 1 step b

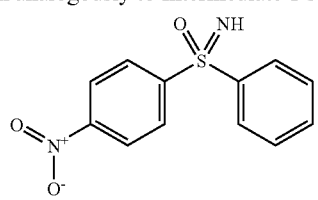

$^1$H-NMR (DMSO-D6): 8.35 (dd, 2H), 8.20 (dd, 2H), 8.01 (dm, 2H), 7.68-7.56 (m, 3H).

Step c) Preparation of (RS)—N-(ethoxycarbonyl)-S-phenyl-S-(4-nitrophenyl) sulfoximide Preparation analogously to Intermediate 1—step c

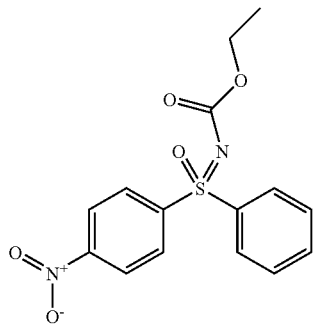 [SMILES: CCOC(=O)N=S(=O)(c1ccccc1)c1ccc([N+](=O)[O-])cc1]

MS (ES+): 335 (M+1, 75%), 289 (100%), 263 (25%)

Step d) Preparation of (RS)—S-(4-aminophenyl)-N-(ethoxycarbonyl)-S-phenyl-sulfoximide Preparation analogously to Intermediate 1 step d

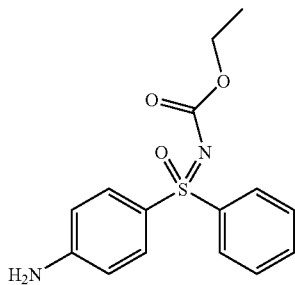

$^1$H-NMR (DMSO-D6): 7.83 (m, 2H), 7.65-7.54 (m, 5H), 6.63 (dm, 2H), 3.91 (qm, 2H), 1.07 (tm, 3H).

Intermediate 7

Preparation of (RS)—S-(4-amino-2-bromophenyl)-N-(ethoxycarbonyl)-S-methyl-sulfoximide

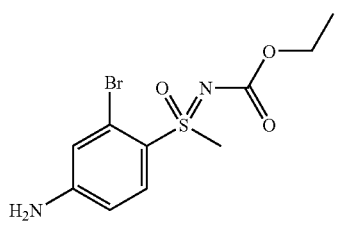 [SMILES: CCOC(=O)N=S(C)(=O)c1ccc(N)cc1Br]

Step a) Preparation of 2-bromo-1-methylsulphanyl-4-nitro-benzene

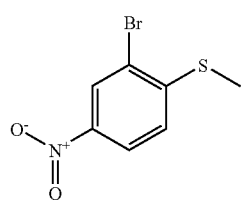

A solution of 25.7 g (120 mmol) 2-bromo-1-fluoro-4-nitrobenzene in 154 ml DMF is treated with 10.6 g (150 mmol) sodium thiomethylate and stirred for 5 hours at 60° C. The mixture is stirred at room temperature for 18 hours, again treated with 1.0 g sodium thiomethylate and stirred for a further 6 hours at 60° C. After cooling, the mixture is poured into ice-water and extracted with ethyl acetate (3×). The combined organic phases are washed with water, dried (Na$_2$SO$_4$), filtered and concentrated. The residue obtained is chromatographically purified (hexane/ethyl acetate 2:1). 20.4 g (82 mmol, corresponding to 70% of theor.) of the product is obtained.

$^1$H-NMR (DMSO-D6): 8.35 (m, 1H), 8.17 (m, 1H), 7.45 (m, 1H), 2.58 (s, 3H).

Step b) Preparation of 2-bromo-1-methanesulfinyl-4-nitro-benzene

Preparation analogously to Intermediate 1—step a

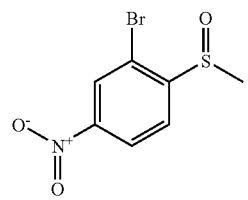

$^1$H-NMR (DMSO-D6): 8.52 (m, 2H), 8.04 (m, 1H), 2.88 (s, 3H).

Step c) Preparation of (RS)—S-(2-bromo-4-nitrophenyl)-S-ethylsulfoximide

Preparation analogously to Intermediate 1—step b

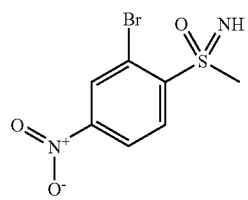

$^1$H-NMR (DMSO-D6): 8.52 (m, 1H), 8.38 (m, 1H), 8.32 (m, 1H), 4.85 (s, 1H), 3.28 (s, 3H).

Step d) Preparation of (RS)—N-(ethoxycarbonyl)-S-ethyl-S-(2-bromo-4-nitrophenyl)-sulfoximide Preparation analogously to Intermediate 1—step c

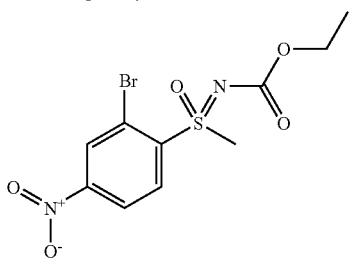

$^1$H-NMR (DMSO-D6): 8.61 (m, 1H), 8.45 (m, 1H), 8.32 (m, 1H), 3.86 (m, 2H), 3.57 (s, 3H), 1.02 (tr, 3H).

Step e) Preparation of (RS)—S-(4-amino-2-bromophenyl)-N-(ethoxycarbonyl)-S-ethylsulfoximide Preparation analogously to Intermediate 1—step d

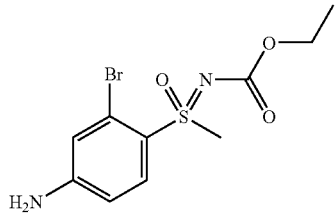 [SMILES: CCOC(=O)N=S(C)(=O)c1ccc(N)cc1Br]

¹H-NMR (DMSO-D6): 7.69 (m, 1H), 6.95 (m, 1H), 6.67 (m, 1H), 6.41 (s, 2H), 3.89 (m, 2H), 3.41 (s, 3H), 1.06 (tr, 3H).

Intermediate 8

Preparation of (RS)—S-(4-aminophenyl)-N,S-dimethylsulfoximide

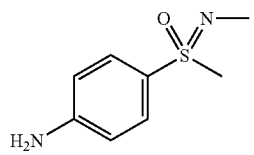

Step a) Preparation of (RS)—N,S-dimethyl-S-(4-nitrophenyl)sulfoximide

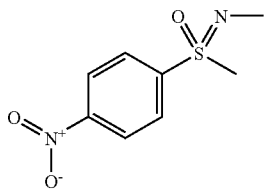

500 mg (2.5 mmol) (RS)—S-(4-nitrophenyl)-S-methylsulfoximide in 4 ml formaldehyde (aqueous, 37%) and 20 ml formic acid (98-100%) are stirred in the open flask at 100° C. After 22 hours, the solvent is evaporated, the mixture is treated again with 4 ml formaldehyde (aqueous, 37%) and 20 ml formic acid (98-100%) and stirred for a further 22 hours at 100° C. Residues of the solvent are removed on the rotary evaporator. The remaining residue is dissolved with 2N HCl and extracted with dichloromethane. The aqueous phase is basified with NaHCO₃ and extracted with dichloromethane. The combined organic phases are dried (Na₂SO₄), filtered and concentrated. 448 mg (2.1 mmol, corresponding to 85% of theor.) of the product is obtained.

¹H-NMR (DMSO-D6): 8.43 (m, 2H), 8.08 (m, 2H), 3.24 (s, 3H), 2.48 (s, 3H).

Step b) Preparation of (RS)—S-(4-aminophenyl)-N,S-dimethylsulfoximide

Preparation analogously to Intermediate 1—step d

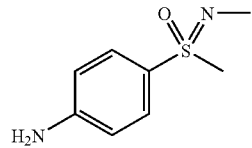

¹H-NMR (DMSO-D6): 7.48 (d, 2H), 6.62 (d, 2H), 5.95 (s, 2H), 2.95 (s, 3H), 2.41 (s, 3H).

Intermediate 9

Preparation of (RS)—S-(4-aminophenyl)-N-propionyl-5-methylsulfoximide

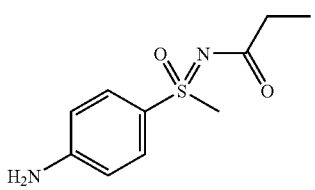

Step a) Preparation of (RS)—S-(4-nitrophenyl)-N-propionyl-5-methylsulfoximide

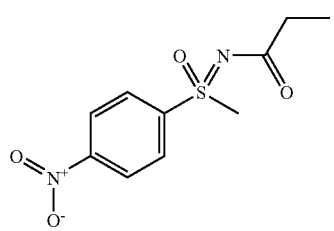

400 mg (2 mmol) (RS)—S-(4-nitrophenyl)-S-methylsulfoximide (Intermediate 1—step b) are dissolved in 15 ml dichloromethane, cooled in the ice-bath and treated with 0.36 ml triethylamine. 185 mg (2 mmol) propionyl chloride are added dropwise with ice cooling. The mixture is stirred for 30 minutes in the ice-bath and for 15 hours at room temperature. After chromatographic purification (silica gel, hexane/ethyl acetate (0-50% ethyl acetate)), 489 mg (96%) of the desired product is obtained.

¹H-NMR (400 MHz, DMSO-D6): 0.95 (t, 3H), 2.28 (q, 2H), 3.51 (s, 3H), 8.20 (d, 2H), 8.46 (d, 2H).

Step b) Preparation of (RS)—S-(4-aminophenyl)-N-propionyl-5-methylsulfoximide

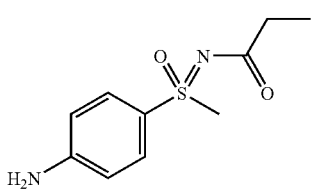

106 mg (0.41 mmol) (RS)—S-(4-nitrophenyl)-N-propionyl-5-methylsulfoximide is dissolved in 10 ml ethanol and treated with 20 mg palladium on activated charcoal (10% Pd). The mixture is stirred under hydrogen at normal pressure for 45 minutes at 23° C. The catalyst is filtered off and the solution concentrated. After chromatographic purification (silica gel, hexane/ethyl acetate (0-50% ethyl acetate)), 72 mg (77%) of the desired product is obtained.

¹H-NMR (400 MHz, DMSO-D6): 0.99 (t, 3H), 2.25 (q, 2H), 3.35 (s, 3H), 6.17 (s, 2H), 6.69 (d, 2H), 7.55 (d, 2H).

Intermediate 10

Preparation of (RS)—S-(4-aminophenyl)-N-propyl-5-methylsulfoximide

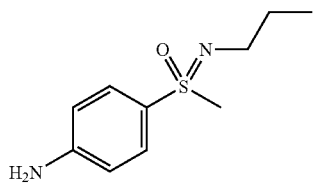

Step a) Preparation of (RS)—S-(4-nitrophenyl)-N-propyl-5-methylsulfoximide

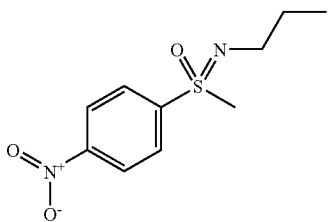 [SMILES: CCCN=S(C)(=O)c1ccc([N+](=O)[O-])cc1]

351 mg (1.37 mmol) (RS)—S-(4-nitrophenyl)-N-propionyl-5-methylsulfoximide (Intermediate 9—step a) are dissolved in 15 ml dichloromethane and treated dropwise with borane-tetrahydrofuran complex (1.0 M solution in tetrahydrofuran, Aldrich) with ice-cooling. The mixture is stirred for 3 hours at 0 C. Next it is cautiously treated with ca.10 ml water/methanol (1:1), stirred for 30 minutes and extracted with dichloromethane. The organic phase is dried over sodium sulfate and concentrated. After chromatographic purification (silica gel, hexane/ethyl acetate (0-50% ethyl acetate)), 146 mg (44%) of the desired product is obtained.

¹H-NMR (400 MHz, DMSO-D6): δ 0.82 (t, 3H), 1.41 (m, 2H), 2.65 (m, 2H), 2.94 (s, 3H), 5.94 (m, 2H), 6.64 (d, 2H), 7.43 (d, 2H)

Step b) Preparation of (RS)—S-(4-aminophenyl)-N-propyl-5-methylsulfoximide

Preparation analogously to Intermediate 1—step d

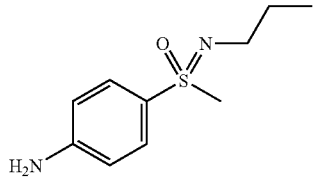

¹H-NMR (400 MHz, DMSO-D6): 0.82 (t, 3H), 1.41 (m, 2H), 2.65 (m, 2H), 2.94 (s, 3H), 5.94 (m, 2H), 6.64 (d, 2H), 7.43 (d, 2H).

Intermediate 11

Preparation of (RS)—S-(3-aminophenyl)-N-(ethoxycarbonyl)-S-methylsulfoximide

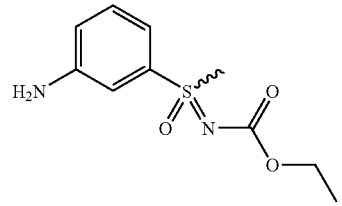 [SMILES: CCOC(=O)N=S(C)(=O)c1cccc(N)c1]

Step a) Preparation of 1-methanesulfinyl-3-nitro-benzene

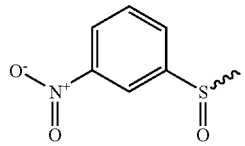

A solution of 3-nitro thioanisol (96 g, 568 mmol) in DCM (100 mL) was added dropwise to a cooled solution of sulfuryl chloride (96 g, 711 mmol) in DCM (600 mL) at −60° C. The mixture was stirred for 4 h at −20° C., then cooled to −60° C., and 350 mL of EtOH were carefully added. The reaction was then allowed to warm up to rt, subsequently, most of the solvent was evaporated, the residue was poured in sat. aq. NaHCO₃, and the solid product was filtered off and carefully washed with hexane on the filter, then air-dried to give the desired sulfoxide (95 g, 90% yield).

¹H-NMR (300 MHz, CDCl₃): 8.51 (s, 1 H); 8.38 (d, 1 H); 8.03 (d, 1 H); 7.78 (t, 1 H); 2.62 (s, 3 H).

Step b) Preparation of (RS)—N-(ethoxycarbonyl)-S-methyl-S-(3-nitrophenyl)-sulfoximide

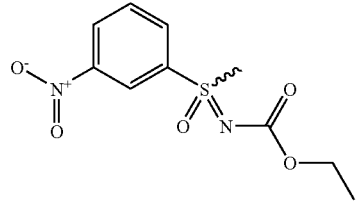 [SMILES: CCOC(=O)N=S(C)(=O)c1cccc([N+](=O)[O-])c1]

In a 1000-mL three-necked flask equipped with reflux condenser, dropping funnel and mechanical stirrer, a mixture of 1-methanesulphinyl-3-nitro-benzene (95 g, 513 mmol), sodium azide (36 g, 553 mmol) and DCM (600 mL) was cooled to 0° C. Subsequently, conc. H₂SO₄ (130 mL) was slowly added. The mixture was then carefully warmed to 45° C. and stirred at this temperature for 24 h. After cooling to room temperature, the mixture was poured on ice and then basified to pH 11 by NaOH. The DCM layer was separated, and the aqueous solution was extracted three more times with DCM. The organic layers are combined, dried over sodium sulfate and evaporated. TLC indicate ~30% unreacted sulfoxide, LCMS analysis showed ~50% conversion to the target product. The crude product mixture (crude weight ~90 g) was dissolved in 300 mL of dry pyridine and treated with ethyl choroformiate (25 mL, 261 mmol) at room temperature. After 10 min, TLC indicated completion of the reaction. The mixture was poured into 1000 mL of water, acidified with aqueous hydrogen chloride to pH 3, extracted with ethyl acetate, dried over sodium sulfate and evaporated. The crude product was purified by column chromatography, followed by crystallisation from ethyl acetate and washing with hexane to give the desired product (72 g, 52% overall yield) and unreacted sulfoxide (23 g).

¹H-NMR (300 MHz, CDCl₃): 8.84 (s, 1 H); 8.56 (d, 1 H); 8.34 (d, 1 H); 7.85 (t, 1 H); 4.02-4.18 (m, 2 H); 3.36 (s, 3 H); 1.24 (t, 3 H).

Step c) Preparation of (RS)—S-(3-aminophenyl)-N-(ethoxycarbonyl)-S-methyl-sulfoximide

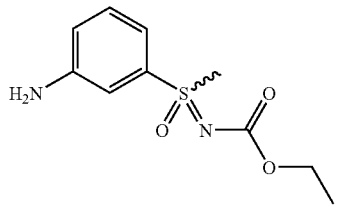 [SMILES: CCOC(=O)N=S(C)(=O)c1cccc(N)c1]

(RS)—S-(3-aminophenyl)-N-(ethoxycarbonyl)-S-methylsulfoximide was prepared from (RS)—N-(ethoxycarbonyl)-S-methyl-S-(3-nitrophenyl)-sulfoximide (4.8 g, 17.6 mmol, 1.0 equiv.) to give 4.2 g of the desired amine (98% yield) according to the following procedure: The respective nitro compound (1.0 eq) is added to a stirred mixture of powdered iron (12 eq) in 85% ethanol (5 mL per mmol nitro compound) and concentrated hydrochloric acid (10 µL per mmol nitro compound) at room temperature. Subsequently, the mixture was stirred at 60° C. until all starting material was consumed (typically after about 3 h). After cooling to room temperature, the mixture was filtered, and the filter cake was repeatedly washed with hot ethanol. The filtrate is evaporated and purified by column chromatography to give the desired amine.

¹H-NMR (300 MHz, CDCl₃): 7.24 (t, 1 H); 7.03-7.08 (m, 1 H); 6.95 (d, 1 H); 6.81 (dd, 1 H); 5.60-5.80 (m, 2 H); 3.80-3.96 (m, 2 H); 3.31 (s, 3 H); 1.06 (t, 3 H).

Intermediate 12

Preparation of (RS)—S-(4-aminophenyl)-N-(ethyl)-S-methylsulfoximide

Preparation analogously to Intermediate 10

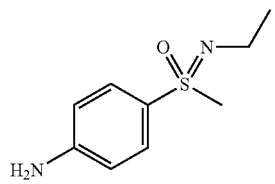

¹H-NMR (400 MHz, DMSO-D6): 1.02 (t, 3H), 2.70 (q, 1H), 2.78 (q, 1H), 2.95 (s, 3H), 5.94 (m, 2H), 6.64 (d, 2H), 7.43 (d, 2H).

Intermediate 13

Preparation of (RS)—S-(4-aminophenyl)-N-(n-propyl)-S-cyclopropylsulfoximide

Preparation analogously to Intermediate 10

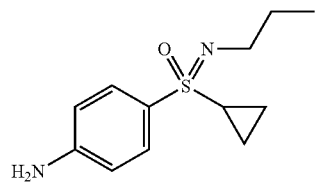 [SMILES: CCCN=S(=O)(c1ccc(N)cc1)C1CC1]

¹H-NMR (400 MHz, DMSO-D6): 0.75 (m, 2H), 0.83 (t, 3H), 0.94 (m, 1H), 1.06 (m, 1H), 1.41 (m, 2H), 2.50 (m, 1H), 2.68 (m, 1H), 2.76 (m, 1H), 5.93 (s, 2H), 6.63 (d, 2H), 7.38 (d, 2H).

Intermediate 14

Preparation of (RS)—S-(4-aminophenyl)-N-(propyl)-S-phenylsulfoximide

Preparation analogously to Intermediate 10

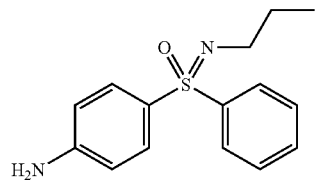 [SMILES: CCCN=S(=O)(c1ccccc1)c1ccc(N)cc1]

¹H-NMR (400 MHz, DMSO-D6): δ 0.89 (t, 3H), 1.51 (m, 2H), 2.81 (m, 2H), 5.99 (s, 2H), 6.59 (d, 2H), 7.52 (m, 5H), 7.80 (m, 2H).

Intermediate 15

Preparation of (RS)—S-(4-aminophenyl)-N-(cyclopropylmethyl)-S-methyl-sulfoximide Preparation analogously to Intermediate 10

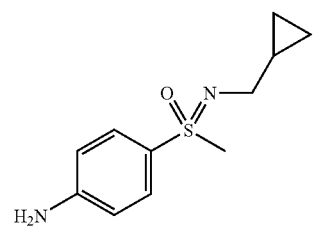

¹H-NMR (400 MHz, DMSO-D6): 0.04 (m, 2H), 0.32 (m, 2H), 0.85 (m, 1H), 2.53-2.68 (m, 2H), 2.95 (s, 3H), 5.94 (s, 2H), 6.63 (d, 2H), 7.42 (d, 2H).

Intermediate 16

Preparation of (RS)—S-(4-aminophenyl)-N-(cyclopropylmethyl)-S-cyclopropyl-sulfoximide Preparation analogously to Intermediate 10

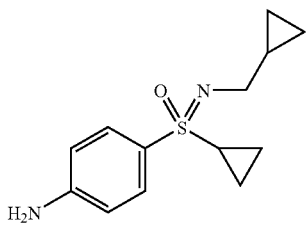 [SMILES: Nc1ccc(S(=O)(=NCC2CC2)C2CC2)cc1]

Intermediate 17

Preparation of (RS)—S-(4-aminophenyl)-N-(cyclopropylmethyl)-S-phenyl-sulfoximide Preparation analogously to Intermediate 10

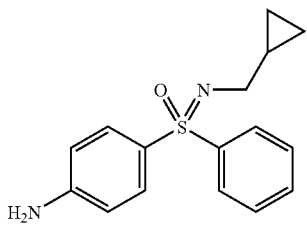 [SMILES: Nc1ccc(S(=O)(=NCC2CC2)c2ccccc2)cc1]

Intermediate 18

Preparation of (RS)—S-(4-aminophenyl)-N-(phenyl)-S-methylsulfoximide

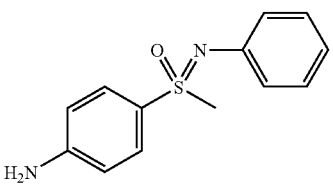 [SMILES: CS(=O)(=Nc1ccccc1)c1ccc(N)cc1]

Step a) Preparation of (RS)—S-(4-nitrophenyl)-N-(phenyl)-S-methylsulfoximide

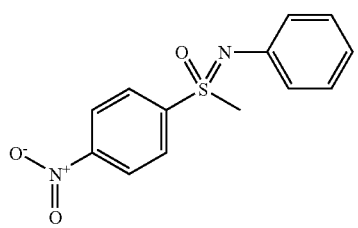 [SMILES: CS(=O)(=Nc1ccccc1)c1ccc([N+](=O)[O-])cc1]

37 mg rac-BINAP and 23 mg bis-(dibenzylidenacetone)-palladium(0) are placed in an argon-flushed two-necked flask with septum. 10 ml toluene, 0.1 ml bromo-benzene, 200 mg (RS)—S-(4-nitrophenyl)-S-methylsulfoximide and 365 mg caesium carbonate are added. The mixture is heated under reflux for 15 hours. The dark brown reaction solution is filtered at the pump over Celite, washed with methyl-tert.-butyl ether and the filtrate concentrated to dryness. After chromatographic purification (silica gel, hexane/ethyl acetate (0-50% ethyl acetate)), 230 mg (83%) of the desired product is obtained.

$^1$H-NMR (400 MHz, DMSO-D6): 3.50 (s, 3H), 6.84 (m, 3H), 7.09 (t, 2H), 8.19 (d, 2H), 8.41 (d, 2H).

Step b) Preparation of (RS)—S-(4-aminophenyl)-N-(phenyl)-S-methylsulfoximide

Preparation analogously to Intermediate 1—step d

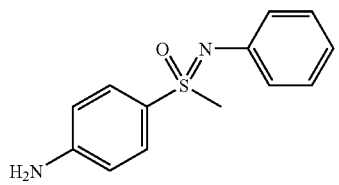

$^1$H-NMR (400 MHz, DMSO-D6): 3.20 (s, 3H), 6.04 (s, 2H), 6.60 (d, 2H), 6.75 (t, 1H), 6.82 (d, 2H), 7.05 (t, 2H), 7.50 (d, 2H).

Intermediate 19

Preparation of (RS)—S-(4-aminophenyl)-N-(methylcarbamoyl)-S-methyl-sulfoximide

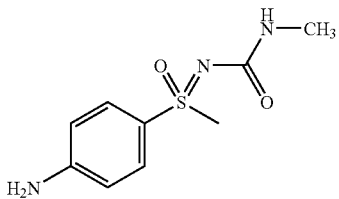

Step a) Preparation of (RS)—S-(4-nitrophenyl)-N-(methylcarbamoyl)-S-methyl-sulfoximide

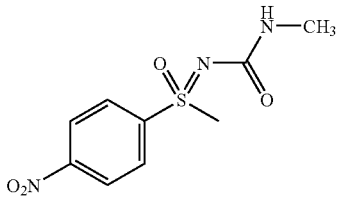

300 mg (1.5 mmol) (RS)—S-(4-nitrophenyl)-S-methylsulfoximide in 8 ml toluene and 4 ml petroleum ether 60/80 are treated with 0.097 ml (1.65 mmol) methyl isocyanate. The mixture is stirred in a pressure tube at 104° C. for 5 hours and at room temperature for 14 hours. The suspension is filtrated to give 302 mg (corresponding to 78% of theor.) of the product.

¹H-NMR (300 MHz, DMSO-D6): 2.46 (d, 3H), 3.43 (s, 3H), 6.97 (q, 1H), 8.17 (d, 2H), 8.45 (d, 2H).

Step b) Preparation of (RS)—S-(4-aminophenyl)-N-(methylcarbamoyl)-S-methylsulfoximide

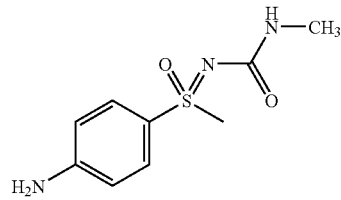 [SMILES: CNC(=O)N=S(C)(=O)c1ccc([N+](=O)[O-])cc1]

302 mg (1.17 mmol) (RS)—S-(4-nitrophenyl)-N-(methylcarbamoyl)-S-methylsulfoximide in 20 ml methanol is hydrogenated over 60 mg palladium (10% on carbon, 50% water wet) for 4 hours at 26° C. and 30 bar. The catalyst is filtered and the solvent evaporated to give 271 mg (corresponding to 100% of theor.) of the product.

¹H-NMR (300 MHz, DMSO-D6): 2.50 (3H), 3.26 (s, 3H), 6.08 (s br, 2H), 6.65 (d, 2H), 6.70 (m, 1H), 7.52 (d, 2H).

Intermediate 20

Preparation of (RS)—S-(4-aminophenyl)-N-(ethylcarbamoyl)-S-methylsulfoximide

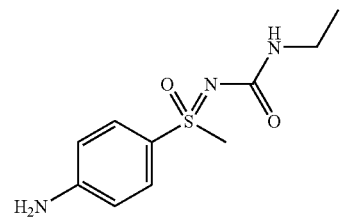

Step a) Preparation of (RS)—S-(4-nitrophenyl)-N-(ethylcarbamoyl)-S-methyl-sulfoximide Preparation analogously to Intermediate 19—step a

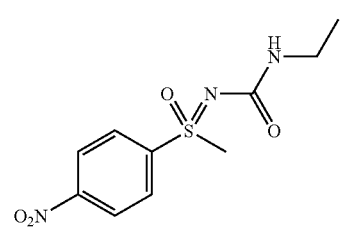

¹H-NMR (300 MHz, DMSO-D6): 0.94 (t, 3H), 2.91 (q, 2H), 3.43 (s, 3H), 7.08 (m, 1H), 8.16 (d, 2H), 8.45 (d, 2H).

Step b) Preparation of (RS)—S-(4-aminophenyl)-N-(ethylcarbamoyl)-S-methyl-sulfoximide Preparation analogously to intermediate 19—step b

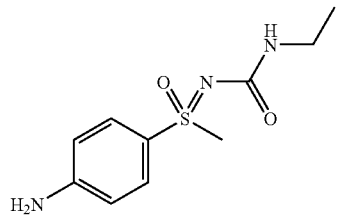 [SMILES: CCNC(=O)N=S(C)(=O)c1ccc([N+](=O)[O-])cc1]

¹H-NMR (300 MHz, DMSO-D6): 0:97 (t, 3H), 2.95 (q, 2H), 3.26 (s, 3H), 6.08 (s br, 2H), 6.64 (d, 2H), 6.78 (m, 1H), 7.52 (d, 2H).

Intermediate 21

Preparation of (RS)—S-(4-aminophenyl)-N-(isopropylcarbamoyl)-S-methyl-sulfoximide

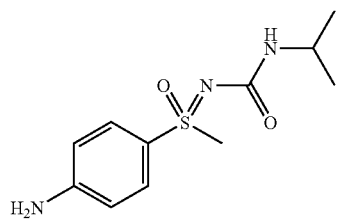 [SMILES: CC(C)NC(=O)N=S(C)(=O)c1ccc(N)cc1]

Step a) Preparation of (RS)—S-(4-nitrophenyl)-N-(isopropylcarbamoyl)-S-methyl-sulfoximide Preparation analogously to intermediate 19—step a

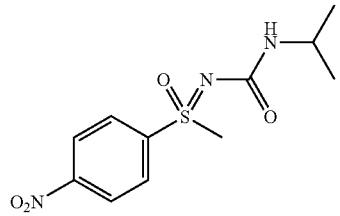 [SMILES: CC(C)NC(=O)N=S(C)(=O)c1ccc(N)cc1]

¹H-NMR (300 MHz, DMSO-D6): 0.99 (m, 6H), 3.43 (s, 3H), 3.55 (m, 1H), 6.98 (m, 1H), 8.17 (d, 2H), 8.46 (d, 2H).

Step b) Preparation of (RS)—S-(4-aminophenyl)-N-(isopropylcarbamoyl)-S-methylsulfoximide Preparation analogously to intermediate 19—step b

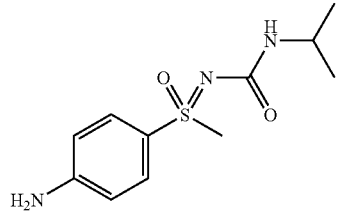

¹H-NMR (300 MHz, DMSO-D6): 1.01 (m, 6H), 3.26 (s, 3H), 3.62 (m, 1H), 6.07 (s br, 2H), 6.65 (d, 2H), 6.66 (d, 1H), 7.53 (d, 2H).

Intermediate 21.1

Preparation of (RS)—S-(3-aminophenyl)-N-(isopropylcarbamoyl)-S-methyl-sulfoximide

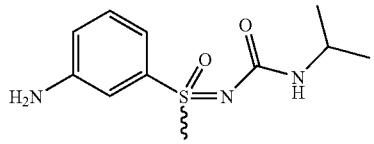

Step a) Preparation of (RS)—S-(3-nitrophenyl)-N-(isopropylcarbamoyl)-S-methyl-sulfoximide Preparation analogously to intermediate 19—step a

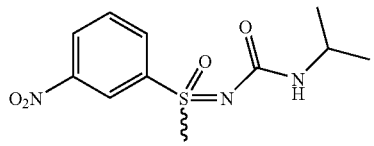

8.24 g (41.2 mmol) (RS)—S-(3-nitrophenyl)-S-methylsulfoximide in 370 ml toluene were treated with 13.6 ml (138.3 mmol) isopropyl isocyanate. The mixture was stirred under argon at 104° C. for 5 hours and at room temperature for 60 hours. 4.5 ml (46 mmol) isopropyl isocyanate were added and the mixture was stirred under argon at 104° C. for 6 hours and at room temperature for 16 hours. 4.5 ml (46 mmol) isopropyl isocyanate were added and the mixture was stirred under argon at 104° C. for 7 hours and at room temperature for 17 hours. The mixture was cooled with ice for 40 minutes. The suspension was filtrated to give 9.2 g (78% yield) of the product.

$^1$H-NMR (300 MHz, DMSO-D6): 8.63 (s, 1 H), 8.54 (d, 1 H), 8.35 (d, 1 H), 7.96 (t, 1 H), 7.01 (d, 1 H), 3.57 (m, 1 H), 3.46 (s, 3 H), 1.00 (m, 6 H).

Step b) Preparation of (RS)—S-(3-aminophenyl)-N-(isopropylcarbamoyl)-S-methylsulfoximide

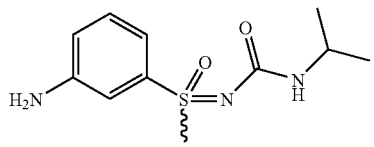

18.61 g iron powder in 198 ml ethanol and 1.93 ml conc. hydrochloric acid were stirred for 30 minutes at room temperature. 7.8 g (27.34 mmol) (RS)—S-(3-nitrophenyl)-N-(isopropylcarbamoyl)-S-methylsulfoximide in 20 ml methanol were added. The mixture was stirred at 60° C. for 2 hours and filtered over a bed of silica gel. The residue was washed with hot ethanol. The combined filtrates were evaporated. The crude residue was purified by column chromatography (silica gel, dichloromethane:dichloromethane/ethanol 1:1) to give 4.53 g (65% yield) of the title compound.

1H-NMR (300 MHz, DMSO-D6): 7.23 (t, 1 H), 7.07 (s, 1 H), 6.97 (d, 1 H), 6.80 (d, 1 H), 6.75 (d, 1 H), 5.65 (s br, 2 H), 3.60 (m, 1 H), 3.27 (s, 3 H), 1.00 (m, 6 H).

Intermediate 22

Preparation of (RS)—S-(4-aminophenyl)-N-(cyclopentylcarbamoyl)-S-methyl-sulfoximide

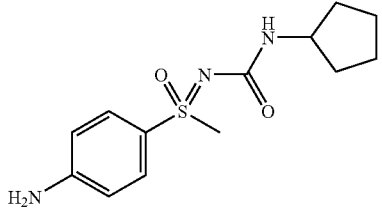

Step a) Preparation of (RS)—S-(4-nitrophenyl)-N-(cyclopentylcarbamoyl)-S-methylsulfoximide Preparation analogously to intermediate 19—step a

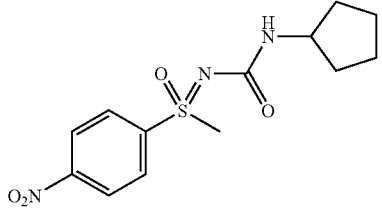 [SMILES: CS(=O)(=NC(=O)NC1CCCC1)c1ccc([N+](=O)[O-])cc1]

$^1$H-NMR (300 MHz, DMSO-D6): δ 1.38 (m, 4H), 1.64 (m, 4H), 3.43 (s, 3H), 3.73 (m, 1H), 7.11 (m, 1H), 8.17 (d, 2H), 8.45 (d, 2H).

Step b) Preparation of (RS)—S-(4-aminophenyl)-N-(cyclopentylcarbamoyl)-S-methylsulfoximide Preparation analogously to intermediate 19—step b

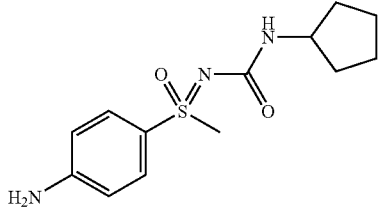

$^1$H-NMR (300 MHz, DMSO-D6): 1.34 (m, 2H), 1.43 (m, 2H), 1.59 (m, 2H), 1.71 (m, 2H), 3.26 (s, 3H), 3.79 (q, 1H), 6.07 (s br, 2H), 6.64 (d, 2H), 6.79 (d, 1H), 7.52 (d, 2H).

Intermediate 23

Preparation of (RS)—S-(4-aminophenyl)-N-(benzyl-carbamoyl)-S-methyl-sulfoximide

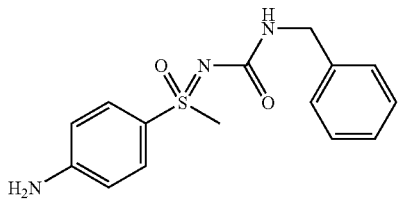

Step a) Preparation of (RS)—S-(4-nitrophenyl)-N-(benzylcarbamoyl)-S-methylsulfoximide Preparation analogously to intermediate 19—step a

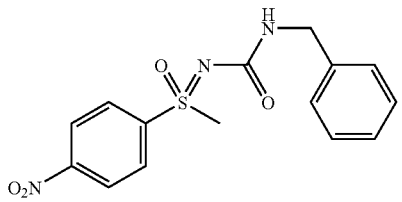 [SMILES: CS(=O)(=NC(=O)NCc1ccccc1)c1ccc([N+](=O)[O-])cc1]

$^1$H-NMR (300 MHz, DMSO-D6): 3.46 (s, 3H), 4.10 (d, 2H), 7.20 (m, 3H), 7.28 (m, 2H), 7.66 (t, 1H), 8.19 (d, 2H), 8.46 (d, 2H).

Step b) Preparation of (RS)—S-(4-aminophenyl)-N-(benzylcarbamoyl)-S-methylsulfoximide Preparation analogously to intermediate 19—step b

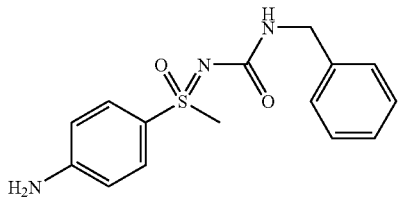

$^1$H-NMR (300 MHz, DMSO-D6): 3.28 (s, 3H), 4.14 (d, 2H), 6.09 (s br, 2H), 6.65 (d, 2H), 7.20 (t, 1H), 7.23 (d, 2H), 7.29 (t, 2H), 7.37 (t, 1H), 7.54 (d, 2H).

Intermediate 24

Preparation of (RS)—S-(4-aminophenyl)-N-(p-tolyl-carbamoyl)-S-methylsulfoximide

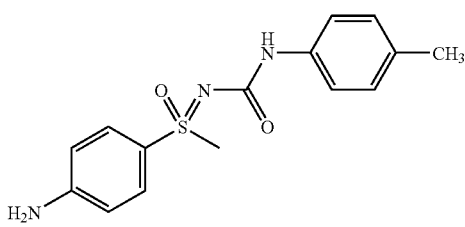 [SMILES: Cc1ccc(NC(=O)N=S(C)(=O)c2ccc([N+](=O)[O-])cc2)cc1]

Step a) Preparation of (RS)—S-(4-nitrophenyl)-N-(p-tolylcarbamoyl)-S-methylsulfoximide Preparation analogously to intermediate 19—step a

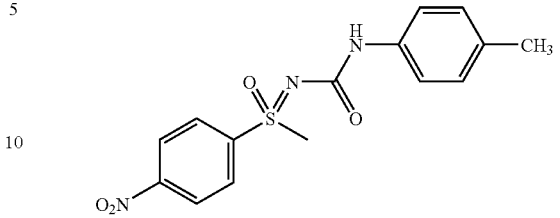

$^1$H-NMR (300 MHz, DMSO-D6): 2.19 (s, 3H), 3.55 (s, 3H), 6.99 (d, 2H), 7.34 (d, 2H), 8.25 (d, 2H), 8.48 (d, 2H), 9.42 (s br, 1H).

Step b) Preparation of (RS)—S-(4-aminophenyl)-N-(p-tolylcarbamoyl)-S-methylsulfoximide Preparation analogously to intermediate 19—step b

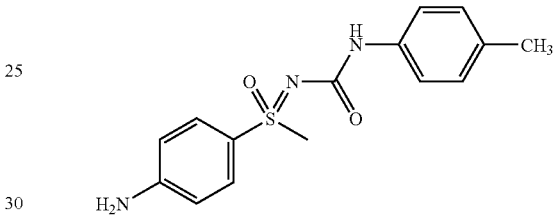

$^1$H-NMR (300 MHz, DMSO-D6): 2.20 (s, 3H), 3.36 (s, 3H), 6.14 (s br, 2H), 6.67 (d, 2H), 7.00 (d, 2H), 7.39 (d, 2H), 7.59 (d, 2H), 9.14 (s br, 1H).

Intermediate 25

Preparation of (RS)—S-(4-aminophenyl)-N-(4-chloro-phenylcarbamoyl)-S-methyl-sulfoximide

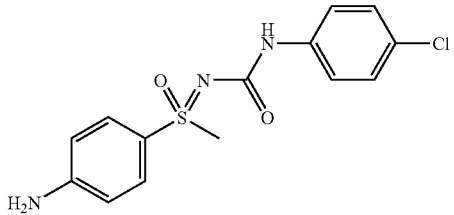 [SMILES: CS(=O)(=NC(=O)Nc1ccc(Cl)cc1)c1ccc([N+](=O)[O-])cc1]

Step a) Preparation of (RS)—S-(4-nitrophenyl)-N-(4-chloro-phenylcarbamoyl)-S-methylsulfoximide Preparation analogously to intermediate 19—step a

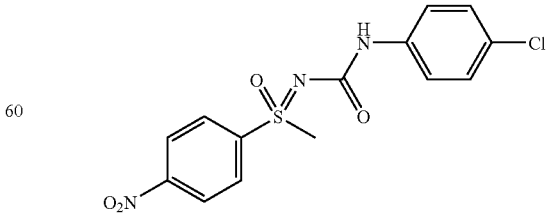

$^1$H-NMR (300 MHz, DMSO-D6): 3.57 (s, 3H), 7.24 (d, 2H), 7.49 (d, 2H), 8.25 (d, 2H), 8.48 (d, 2H), 9.68 (s br, 1H).

Step b) Preparation of (RS)—S-(4-aminophenyl)-N-(4-chloro-phenylcarbamoyl)-S-methylsulfoximide Preparation analogously to intermediate 19—step b

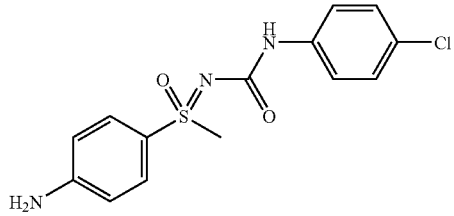 [SMILES: CS(=O)(=NC(=O)Nc1ccc(Cl)cc1)c1ccc(N)cc1]

¹H-NMR (300 MHz, DMSO-D6): 3.37 (s, 3H), 6.14 (s br, 2H), 6.67 (d, 2H), 7.25 (d, 2H), 7.54 (d, 2H), 7.59 (d, 2H), 9.40 (s br, 1H).

Intermediate 26

Preparation of (RS)—S-(4-aminophenyl)-N-(3-chloro-phenylcarbamoyl)-S-methyl-sulfoximide

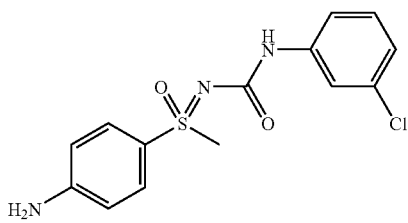 [SMILES: CS(=O)(=NC(=O)Nc1cccc(Cl)c1)c1ccc([N+](=O)[O-])cc1]

Step a) Preparation of (RS)—S-(4-nitrophenyl)-N-(3-chloro-phenylcarbamoyl)-S-methylsulfoximide Preparation analogously to intermediate 19—step a

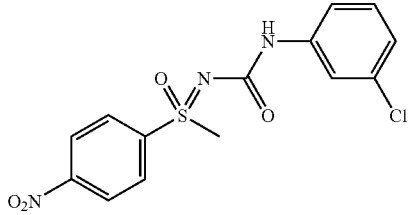

¹H-NMR (300 MHz, DMSO-D6): 3.58 (s, 3H), 6.95 (d, 1H), 7.21 (t, 1H), 7.35 (d, 1H), 7.64 (s, 1H), 8.25 (d, 2H), 8.49 (d, 2H), 9.75 (s br, 1H).

Step b) Preparation of (RS)—S-(4-aminophenyl)-N-(3-chloro-phenylcarbamoyl)-S-methylsulfoximide Preparation analogously to intermediate 19—step b

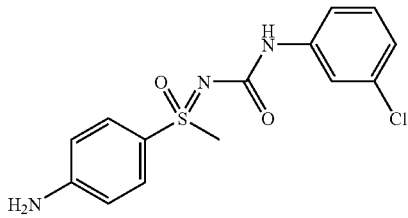

¹H-NMR (300 MHz, DMSO-D6): δ 3.38 (s, 3H), 6.15 (s br, 2H), 6.69 (d, 2H), 6.93 (d, 1H), 7.21 (t, 1H), 7.38 (d, 1H), 7.59 (d, 2H), 7.71 (s, 1H), 9.47 (s br, 1H).

Intermediate 27

Preparation of (RS)—S-(4-aminophenyl)-N-(4-methoxy-phenylcarbamoyl)-S-methylsulfoximide

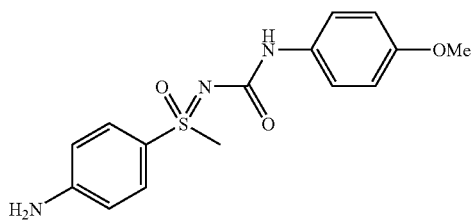

Step a) Preparation of (RS)—S-(4-nitrophenyl)-N-(4-methoxy-phenylcarbamoyl)-S-methylsulfoximide Preparation analogously to intermediate 19—step a

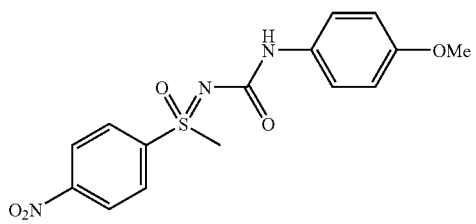

¹H-NMR (300 MHz, DMSO-D6): 3.54 (s, 3H), 3.67 (s, 3H), 6.77 (d, 2H), 7.36 (d, 2H), 8.24 (d, 2H), 8.48 (d, 2H), 9.36 (s br, 1H).

Step b) Preparation of (RS)—S-(4-aminophenyl)-N-(4-methoxy-phenylcarbamoyl)-S-methylsulfoximide Preparation analogously to intermediate 19—step b

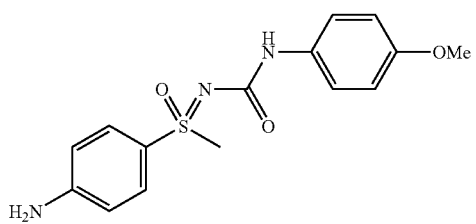 [SMILES: COc1ccc(NC(=O)N=S(C)(=O)c2ccc([N+](=O)[O-])cc2)cc1]

¹H-NMR (300 MHz, DMSO-D6): δ 3.35 (s, 3H), 3.67 (s, 3H), 6.13 (s br, 2H), 6.67 (d, 2H), 6.78 (d, 2H), 7.41 (d, 2H), 7.58 (d, 2H), 9.08 (s br, 1H).

Intermediate 28

Preparation (RS)—S-(4-aminophenyl)-N-(4-dimethylamino-phenylcarbamoyl)-S-methylsulfoximide

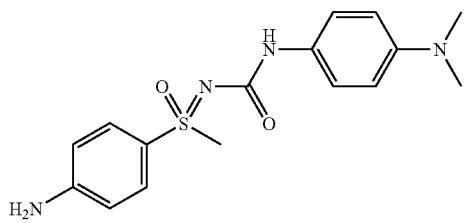

Step a) Preparation of (RS)—S-(4-nitrophenyl)-N-(4-dimethylamino-phenylcarbamoyl)-S-methylsulfoximide Preparation analogously to intermediate 19—step a

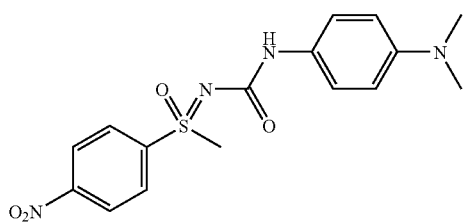

$^1$H-NMR (300 MHz, DMSO-D6): 2.79 (s, 6H), 3.52 (s, 3H), 6.61 (d, 2H), 7.27 (d, 2H), 8.24 (d, 2H), 8.48 (d, 2H), 9.19 (s br, 1H).

Step b) Preparation of (RS)—S-(4-aminophenyl)-N-(4-dimethylamino-phenyl-carbamoyl)-S-methylsulfoximide Preparation analogously to intermediate 19—step b

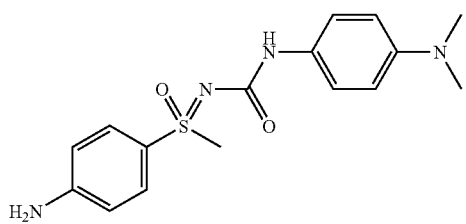 [SMILES: CN(C)c1ccc(NC(=O)N=S(C)(=O)c2ccc([N+](=O)[O-])cc2)cc1]

$^1$H-NMR (300 MHz, DMSO-D6): 2.79 (s, 6H), 3.34 (s, 3H), 6.13 (s br, 2H), 6.63 (d, 2H), 6.67 (d, 2H), 7.32 (d, 2H), 7.58 (d, 2H), 8.92 (s br, 1H).

Intermediate 29

Preparation of (RS)—S-(4-aminophenyl)-N-(pyridin-3-ylcarbamoyl)-S-methyl-sulfoximide

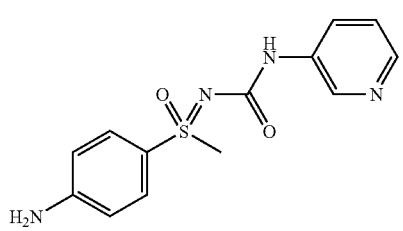

Step a) Preparation of (RS)—S-(4-nitrophenyl)-N-(pyridin-3-ylcarbamoyl)-S-methylsulfoximide Preparation analogously to intermediate 19—step a

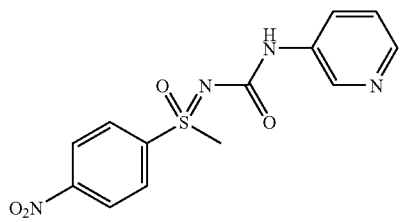

$^1$H-NMR (300 MHz, DMSO-D6): 3.59 (s, 3H), 7.22 (dd, 1H), 7.88 (dm, 1H), 8.12 (dd, 1H), 8.27 (d, 2H), 8.49 (d, 2H), 8.61 (d, 1H), 9.73 (s br, 1H).

Step b) Preparation of (RS)—S-(4-aminophenyl)-N-(pyridin-3-ylcarbamoyl)-S-methylsulfoximide Preparation analogously to intermediate 19—step b

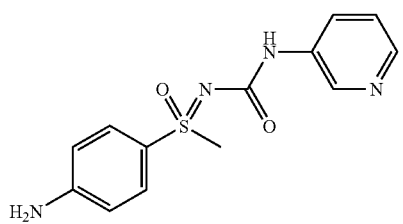 [SMILES: CS(=O)(=NC(=O)Nc1cccnc1)c1ccc([N+](=O)[O-])cc1]

$^1$H-NMR (300 MHz, DMSO-D6): 3.39 (s, 3H), 6.17 (s br, 2H), 6.68 (d, 2H), 7.23 (dd, 1H), 7.60 (d, 2H), 7.94 (dm, 1H), 8.10 (dd, 1H), 8.65 (d, 1H), 9.47 (s br, 1H).

Intermediate 30

Preparation of (RS)—S-(4-aminophenyl)-N-(2-methoxy-ethyl)-S-methyl-sulfoximide

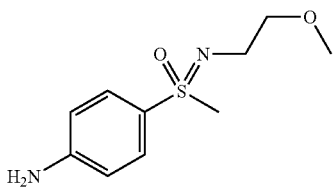

Step a) Preparation of (RS)—S-(4-nitrophenyl)-N-(2-methoxy-acetyl)-S-methylsulfoximide

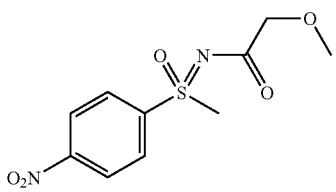

100 mg (0.5 mmol) (RS)—S-(4-nitrophenyl)-S-methylsulfoximide (Example 1b) are dissolved in 3.33 ml dichloromethane, cooled in the ice-bath and treated with 0.1 ml (0.75 mmol) triethylamine. 0.068 ml (0.75 mmol) 2-methoxy-acetyl chloride are added dropwise with ice cooling. The mixture is stirred for 30 minutes in the ice-bath and for 15 hours at room temperature. After chromatographic purification (silica gel, hexane/ethyl acetate (0-50% ethyl acetate)), 107 mg (79%) of the desired product is obtained.

¹H-NMR (400 MHz, DMSO-D6): 3.26 (s, 3H), 3.58 (s, 3H), 3.95 (m, 2H), 8.23 (d, 2H), 8.48 (d, 2H).

Step b) Preparation of (RS)—S-(4-aminophenyl)-N-(2-methoxy-acetyl)-S-methyl-sulfoximide

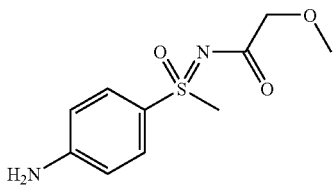 [SMILES: COCC(=O)N=S(C)(=O)c1ccc([N+](=O)[O-])cc1]

107 mg (0.39 mmol) (RS)—S-(4-nitrophenyl)-N-(2-methoxy-acetyl)-S-methylsulfoximide is dissolved in 13.6 ml ethanol and treated with 40 mg palladium on activated charcoal (10% Pd). The mixture is stirred under hydrogen at normal pressure for 60 minutes at 24 C. The catalyst is filtered off and the solution concentrated. After chromatographic purification (silica gel, hexane/ethyl acetate (0-50% ethyl acetate)), 50 mg (53%) of the desired product is obtained.

¹H-NMR (400 MHz, DMSO-D6): 3.27 (s, 3H), 3.35 (s, 3H), 3.89 (s, 2H), 6.19 (m, 2H), 6.67 (d, 2H), 7.54 (d, 2H).

Step c) Preparation of (RS)—S-(4-aminophenyl)-N-(2-methoxy-ethyl)-S-methylsulfoximide

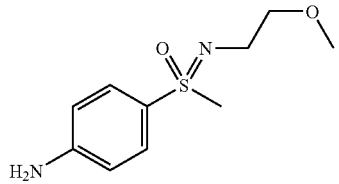

493 mg (2.03 mmol) (RS)—S-(4-aminophenyl)-N-(2-methoxy-acetyl)-S-methylsulphoximide is dissolved in 67.8 ml tetrahydrofuran, cooled in the ice-bath and treated dropwise with 6.13 ml (6.13 mmol) borane tetrahydrofuran complex. The mixture is stirred for 90 minutes and quenched with one drop of methanol and one drop of water. After chromatographic purification (silica gel, hexane/ethyl acetate (0-50% ethyl acetate)), 383 mg (82%) of the desired product is obtained.

¹H-NMR (400 MHz, DMSO-D6): 2.80 (q, 1H), 2.87 (q, 1H), 2.96 (s, 3H), 3.19 (s, 3H), 3.32 (t, 2H), 5.96 (s br, 2H), 6.65 (d, 2H), 7.44 (d, 2H).

Intermediate 31

Preparation of (RS)—S-(4-aminophenyl)-N-(morpholine-4-carbonyl)-S-methyl-sulfoximide

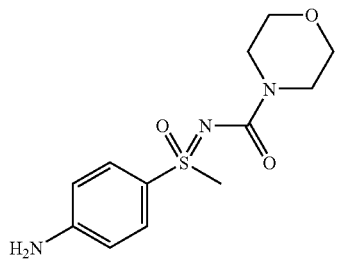

Step a) Preparation of (RS)—S-(4-nitrophenyl)-N-(morpholine-4-carbonyl)-S-methylsulfoximide

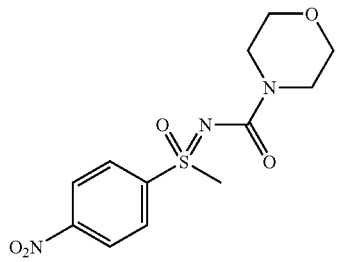

100 mg (0.5 mmol) (RS)—S-(4-nitrophenyl)-S-methylsulphoximide in 4 ml dimethylformamide are treated at room temperature with 23.97 mg sodium hydride (55%, 0.55 mmol). The mixture is stirred for 30 minutes at room temperature and for 30 minutes at 50 C. After cooling to room temperature 0.063 ml (0.55 mmol) 4-morpholinocarbonyl chloride are added. The mixture is stirred for 30 minutes at room temperature and for 2 hours at 50 C and finally quenched with methanol. After chromatographic purification (silica gel, hexane/ethyl acetate (0-50% ethyl acetate)), 87 mg (0.28 mmol, corresponding to 56% of theor.) of the desired product is obtained.

$^1$H-NMR (300 MHz, DMSO-D6): 3.13 (t, 4H), 3.50 (s, 3H), 3.55 (t, 4H), 8.19 (d, 2H), 8.46 (d, 2H).

Step b) Preparation of (RS)—S-(4-aminophenyl)-N-(morpholine-4-carbonyl)-S-methylsulfoximide Preparation analogously to intermediate 1—step d

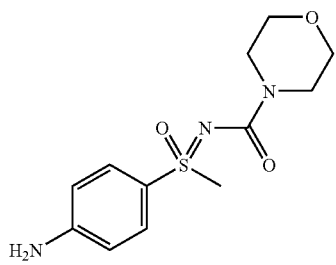 [SMILES: CS(=O)(=NC(=O)N1CCOCC1)c1ccc([N+](=O)[O-])cc1]

$^1$H-NMR (300 MHz, DMSO-D6): 3.13 (t, 4H), 3.32 (s, 3H), 3.55 (t, 4H), 6.12 (s br, 2H), 6.66 (d, 2H), 7.54 (d, 2H).

Preparation of the Diaminopyrimidines Intermediates

Intermediate 32

Preparation of 2,4-dichloro-5-iodopyrimdine

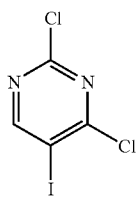

To a suspension of 5-iodouracil (10.0 g; 42 mmol) in N,N-dimethylaniline (11.0 mL) was added POCl$_3$ (64.4 g, 39.2 mL, 420 mmol). The resulting mixture was heated to 90° C. and was stirred at this temperature for 90 min. After cooling to room temperature, excess POCl$_3$ was evaporated and the residue was poured into a mixture of water and ice. After 2 h, the crystalline precipitate was isolated by filtration and washed with water. The crude product was then dissolved in ethyl acetate and the resulting solution was extracted with aqueous sodium bicarbonate and aqueous sodium sulfite. After drying over sodium sulfate, the solvent was evaporated and the residue was purified by column chromatography to give the title compound (10.6 g, 92% yield).

$^1$H-NMR (400 MHz, CDCl$_3$): 8.90 (s, 1 H).

Intermediate 33

Preparation of (R)-2-(2-chloro-5-iodopyrimdin-4-ylamino)propan-1-ol

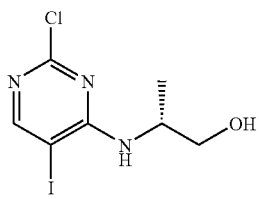

To a solution of 2,4-dichloro-5-iodopyrimidine (3.0 g; 10.9 mol) in acetonitrile (35 mL) was added triethylamine (1.32 g, 1.82 mL, 13.1 mmol), followed by (R)-2-aminopropanol (0.88 g, 11.8 mmol). The mixture was stirred at room temperature for 24 h and was then diluted with ethyl acetate, followed by extraction with brine, 10% aqueous citric acid, and aqueous sodium bicarbonate. After drying over sodium sulfate, the solvent was evaporated and the residue was purified by column chromatography to give the title compound (3.0 g, 88% yield).

$^1$H-NMR (300 MHz, DMSO): 8.30 (s, 1 H); 6.56 (d, 1 H); 4.86 (t, 1 H); 4.50-4.15 (m, 1 H); ); 3.35-3.45 (m, 2 H); 1.10 (d, 3 H).

Intermediate 34

Preparation of (RS)—N-(Ethoxycarbonyl)-S-(3-{[4-{[(R)-2-(hydroxy-1-methylethyl]amino}-5-iodopyrimidin-2-yl]amino}phenyl)-S-methyl-sulfoximide

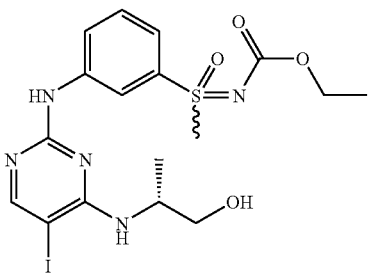 [SMILES: CCOC(=O)N=S(C)(=O)c1cccc(Nc2ncc(I)c(N[C@H](C)CO)n2)c1]

Intermediate 34 was prepared in analogy to GP 4 by reaction of 25 g of Intermediate 33 and 20 g of Intermediate 11 to yield (after preprarative HPLC purification) 12 g of Intermediate 34 (29% yield).

$^1$H-NMR (300 MHz, DMSO): 9.75 (s, 1 H); 8.62 (s, 1 H); 8.20 (s, 1 H); 7.87 (d, 1 H); 7.54 (t, 1 H); 7.43 (d, 1 H); 6.03

(d, 1 H); 4.90-4.95 (m, 1 H); 4.25-4.35 (m, 1 H); 3.85-3.95 (m, 2 H); 3.45-3.55 (m, 2 H); 3.30 (s, 3 H); 1.15 (d, 3 H); 1.08 (t, 3 H).

Intermediate 35

Preparation of (RS)—N-(Ethoxycarbonyl)-S-(4-{[4-{[(R)-2-(hydroxy-1-methylethyl]amino}-5-iodopyrimidin-2-yl]amino}phenyl)-S-methylsulfoximide

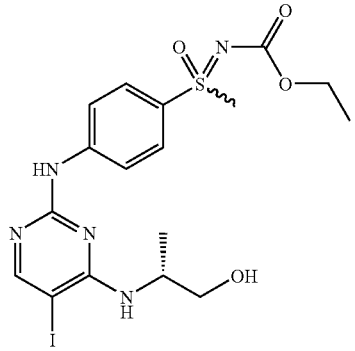 [SMILES: CCOC(=O)N=S(C)(=O)c1ccc(Nc2ncc(I)c(N[C@H](C)CO)n2)cc1]

Intermediate 35 was prepared in analogy to GP 4 by reaction of 25 g of Intermediate 33 and 20 g of Intermediate 1 to yield (after preprarative HPLC purification) 15 g of Intermediate 35 (45% yield).

$^1$H-NMR (300 MHz, DMSO): 9.84 (s, 1 H); 8.31 (s, 1 H); 8.22 (s, 1 H); 7.98 (d, 2H); 7.80 (d, 2 H); 6.05 (d, 1 H); 4.95 (s br, 1 H); 4.20-4.25 (m, 1 H); 3.90 (q, 2 H); 3.50-3.55 (m, 2 H); 3.40 (s, 3 H); 1.20 (d, 3 H); 1.10 (t, 3 H).

Intermediate 35.1

Preparation of (RS)—S-(3-[4-((R)-2-Hydroxy-1-methyl-ethylamino)-5-iodo-pyrimidin-2-ylaminophenyl])-N-(isopropylcarbamoyl)-S-methylsulfoximide

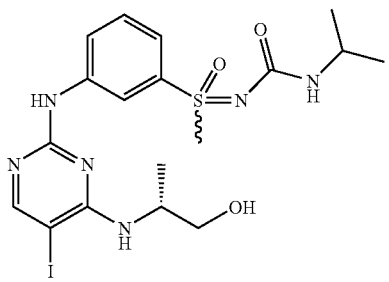 [SMILES: CC(C)NC(=O)N=S(C)(=O)c1cccc(Nc2ncc(I)c(N[C@H](C)CO)n2)c1]

Intermediate 35.1 was prepared in analogy to GP 4 by reacting 1.62 g (5.17 mmol) (R)-2-(2-Chloro-5-iodo-pyrimidin-4-ylamino)-propan-1-ol and 1.2 g (4.7 mmol) (RS)—S-(3-aminophenyl)-N-(isopropylcarbamoyl)-S-methylsulfoximide in 14.8 ml acetonitrile in the presence of 1.17 ml 4 N hydrochloric acid (4.7 mmol) at 52° C. for 20 hours. 10 ml 2 N ammonia in methanol were added and the mixture was stirred for 20 minutes. The mixture is concentrated and purified by column chromatography to give 2.11 g (84% yield) of the title compound.

$^1$H-NMR (300 MHz, DMSO-D6): 9.66 (s, 1 H), 8.57 (s, 1 H), 8.19 (s, 1 H), 7.81 (d, 1 H), 7.49 (t, 1 H), 7.41 (d, 1 H), 6.79 (m, 1 H), 5.99 (m, 1 H), 4.93 (m, 1 H), 4.28 (m, 1 H), 3.59 (m, 1 H), 3.52 (m, 2 H), 3.32 (d, 3 H), 1.19 (d, 3 H), 1.00 (m, 6 H).

Intermediate 36

Preparation of (RS)—S-(3-{[4-{[(R)-2-(hydroxy-1-methylethyl]amino}-5-iodopyrimidin-2-yl]amino}phenyl)-S-methylsulfoximide

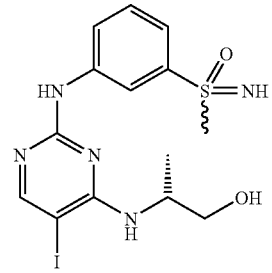

Intermediate 36 was prepared in analogy to GP 6b from intermediate 34 (1.0 eq.) and sodium ethoxide (3.0 eq.) in 62% yield.

$^1$H-NMR (300 MHz, DMSO): 9.56 (s br, 1 H); 8.59 (d, 1 H); 8.14 (s, 1 H); 7.66-7.74 (m, 1 H); 7.37-7.44 (m, 2 H); 5.93 (mc, 1 H); 4.90-4.98 (m, 1 H); 4.29 (mc, 1 H); 4.07-4.14 (m, 1 H); 3.39-3.54 (m, 2 H); 2.99 (s, 3 H); 1.16 (d br, 3 H).

MS (ESI): [M+H]$^+$=448.

Intermediate 37

Preparation of (RS)—S-(4-{[4-{[(R)-2-(hydroxy-1-methylethyl]amino}-5-iodopyrimidin-2-yl]amino}phenyl)-S-methylsulfoximide

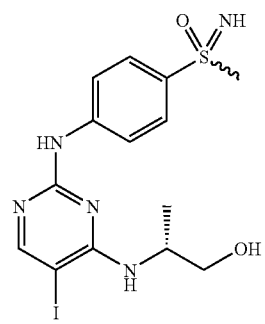 [SMILES: C[C@H](CO)Nc1nc(Nc2ccc(S(C)(=N)=O)cc2)ncc1I]

Intermediate 37 was prepared in analogy to GP 6b by treating 3000 mg (5.78 mmol) of Intermediate 35 with 6.4 mL NaOEt solution (21%; 17.4 mmol, 3 eq.) in 96 mL EtOH and heating to 100° C. for 15 min under microwave irradiation yielding 2.73 g of the desired product (quantitative yield).

$^1$H-NMR (300 MHz, DMSO): 9.66 (s, 1 H); 8.17 (s, 1 H); 7.88 (d, 2 H); 7.74 (d, 2H); 5.99 (d, 1 H); 4.93 (br. s, 1 H); 4.18 (mc, 1 H); 3.94 (s, 1 H); 3.46-3.52 (m, 2 H); 2.97 (s, 3 H); 1.17 (d, 3 H)

MS (ESI): [M+H]$^+$=448. .

Intermediate 38.1

Preparation of
(2-Chloro-5-iodo-pyrimidin-4-yl)-methyl-amine

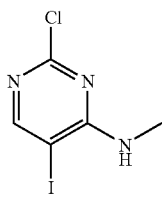

In analogy to GP 2, reaction of 2,4-dichloro-5-iodopyrimidine (12.4 g; 45 mmol) in acetonitrile (250 mL) with methylamine (23.6 mL of a 2 M solution in THF, 45.7 mmol) in the presence of triethylamine (6.86 mL, 49.5 mmol) provided 5.33 g of Intermediate 38.1 (44% yield).

$^1$H-NMR (400 MHz, DMSO): 8.27 (s, 1 H); 7.34 (s br, 1 H); 2.79 (d, 3 H).

MS (ESI): [M+H]$^+$=270 ($^{35}$Cl).

Intermediate 38.2

Preparation of (RS)—N-(Ethoxycarbonyl)-S-(4-{5-iodo-4-methylamino-pyrimidin-2-yl]amino}phenyl)-S-methylsulfoximide

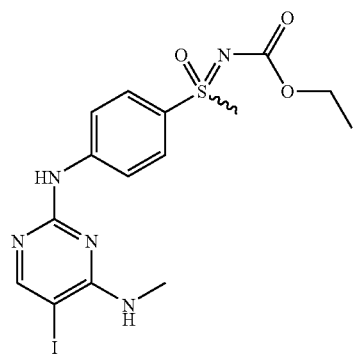 [SMILES: CCOC(=O)N=S(C)(=O)c1ccc(Nc2ncc(I)c(NC)n2)cc1]

Intermediate 38.2 was prepared in analogy to GP 4 by reaction of 1.39 g of Intermediate 38.1 (5.16 mmol) and 1.00 g of Intermediate 1 (4.13 mmol) to yield 1.25 g of Intermediate 38.2 (64% yield).

$^1$H-NMR (300 MHz, DMSO): 9.77 (s, 1 H); 8.15 (s, 1 H); 7.98 (d, 2 H); 7.75 (d, 2 H); 6.81 (q br, 1 H); 3.88 (mc, 2 H); 3.37 (s, 3 H); 2.89 (d, 3 H); 1.07 (t, 3 H).

MS (ESI): [M+H]$^+$=476.

Intermediate 38.3

Preparation (RS)—S-(4-{5-iodo-4-methylamino-pyrimidin-2-yl]amino}phenyl)-S-methylsulfoximide

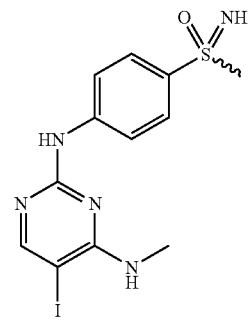 [SMILES: CNc1nc(Nc2ccc(S(C)(=N)=O)cc2)ncc1I]

Intermediate 38.3 was prepared in analogy to GP 6b from intermediate 38.2 (1.0 eq.) and sodium ethoxide (3.0 eq.) in 92% yield.

$^1$H-NMR (300 MHz, DMSO): 9.62 (s, 1 H); 8.13 (s, 1 H); 7.91 (d, 2 H); 7.73 (d, 2 H); 6.76 (mc, 1 H); 3.91 (s, 1 H); 2.98 (s, 3 H); 2.90 (d, 3 H).

MS (ESI): [M+H]$^+$=404.

Intermediate 39.1

Preparation of
(2-Chloro-5-iodo-pyrimidin-4-yl)-ethyl-amine

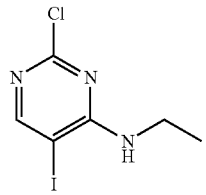

In analogy to GP 2, reaction of 2,4-dichloro-5-iodopyrimidine (12.4 g; 45 mmol) in acetonitrile (350 mL) with ethylamine (23.6 mL of a 2 M solution in THF, 47.3 mmol) in the presence of triethylamine (6.86 mL, 49.5 mmol) provided 6.30 g of Intermediate 38.1 in (49% yield).

$^1$H-NMR (600 MHz, DMSO): 8.30 (s, 1 H); 7.36 (t br, 1 H); 3.38 (mc, 2 H); 1.12 (t, 3 H).

MS (ESI): [M+H]$^+$=284 ($^{35}$Cl).

Intermediate 39.2

Preparation of (RS)—N-(Ethoxycarbonyl)-S-(4-{4-ethylamino-5-iodo-pyrimidin-2-yl]amino}phenyl)-S-methylsulfoximide

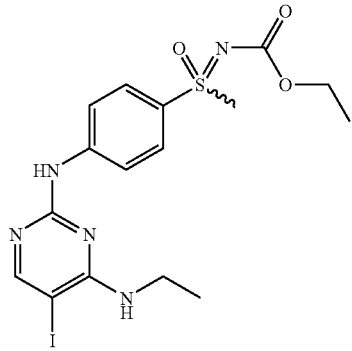 [SMILES: CCNc1nc(Nc2ccc(S(C)(=O)=NC(=O)OCC)cc2)ncc1I]

Intermediate 39.2 was prepared in analogy to GP 4 by reaction of 1.46 g of Intermediate 39.1 (5.16 mmol) and 1.00 g of Intermediate 1 (4.13 mmol) to yield 1.30 g of Intermediate 39.2 (64% yield).

$^1$H-NMR (300 MHz, DMSO): 9.74 (s, 1 H); 8.16 (s, 1 H); 7.97 (d, 2 H); 7.74 (d, 2 H); 6.78 (t br, 1 H); 3.88 (mc, 2 H); 3.42 (mc, 2 H); 3.38 (s, 3 H); 1.14 (t, 3 H); 1.07 (t, 3 H).

MS (ESI): [M+H]$^+$=490.

Intermediate 39.3

Preparation (RS)—S-(4-{4-ethylamino-5-iodo-pyrimidin-2-yl]amino}phenyl)-S-methylsulfoximide

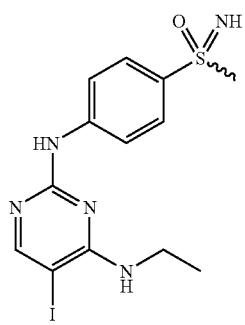 [SMILES: CCNc1nc(Nc2ccc(S(C)(=N)=O)cc2)ncc1I]

Intermediate 39.3 was prepared in analogy to GP 6b from intermediate 39.2 (1.0 eq.) and sodium ethoxide (3.0 eq.) in 83% yield.

$^1$H-NMR (300 MHz, DMSO): 9.61 (s, 1 H); 8.13 (s, 1 H); 7.90 (d, 2 H); 7.72 (d, 2 H); 6.73 (t br, 1 H); 3.92 (s, 1 H); 3.43 (mc, 2 H); 2.98 (s, 3 H); 1.16 (t, 3 H).

MS (ESI): [M+H]$^+$=418.

Intermediate 40.1

Preparation of 2-(2-chloro-5-iodopyrimidine-4-ylamino)ethanol

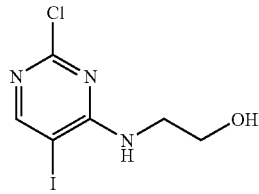

In analogy to GP 2, reaction of 2,4-dichloro-5-iodopyrimidine (2.0 g, 7.3 mmol) with 2-amino-ethanol (480 mg, 7.9 mmol) provided the desired product in 83% yield (1.8 g) after chromatographic purification (silica gel, dichloromethane/methanol (0% to 20% methanol)).

$^1$H-NMR (400 MHz, DMSO-D6):3.35-3.40 (m, 2H), 3.45-3.54 (m, 2H), 4.80 (t, 1H), 7.12 (t, 1H), 8.33 (s, 1H).

Intermediate 41.1

Preparation of N-[2-(2-chloro-5-iodopyrimidine-4-ylamino)ethyl]acetamide

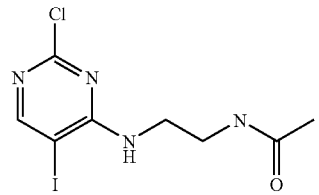

In analogy to GP 2 reaction of 2,4-dichloro-5-iodopyrimidine (1.0 g, 3.6 mmol) with N-(2-aminoethyl)acetamide (e.g. ABCR, Aldrich) (0.42 mL, 3.9 mmol) provided the desired product in 71% yield (878 mg) after trituration of the crystals obtained with diethyl ether.

$^1$H-NMR (300 MHz, DMSO-D6): 1.75 (s, 3H), 3.10-3.25 (m, 2H), 3.30-3.40 (m, 2H), 7.35 (t, 1H), 7.95 (t, 1H), 8.75 (s, 1H).

Intermediate 42.1

Preparation of 3-(2-chloro-5-iodopyrimidine-4-ylamino)propan-1-ol

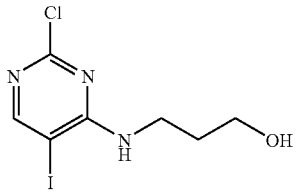 [SMILES: OCCCNc1nc(Cl)ncc1I]

In analogy to GP 2 reaction of 3-amino-1-propanol (0.38 ml, 5 mmol) in the presence of N-ethyldiisopropylamine (1.74 ml, 10 mmol) in 150 ml acetonitrile with 2,4-dichloro-5-iodo-pyrimidine (1.51, 5.5 mmol) provided the target compound after column chromatography in 95% yield.

$^1$H-NMR (400 MHz, DMSO-D6): 1.66 (m, 2H), 3.37 (q, 2H), 3.44 (q, 2H), 4.60 (t, 1H), 7.33 (t, 1H), 8.27 (s, 1H).

MS: 314 (MH+).

Intermediate 43.1

Preparation of (2-chloro-5-iodopyrimidine-4-yl)-(3-morpholin-4-yl-propyl)-amine

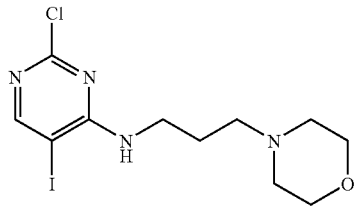 [SMILES: Clc1ncc(I)c(NCCCN2CCOCC2)n1]

In accordance with GP 2,3-morpholin-4-yl-propylamine (0.73 ml, 5 mmol) and N-ethyldiisopropylamine (1.71 ml, 10 mmol) were dissolved in 100 ml acetonitrile under argon and cooled to −35° C. The solution of 2,4-dichloro-5-iodo-pyrimidine (1.37, 5.0 mmol) in 50 ml acetonitrile was then added dropwise at −35° C. internal temperature. Stirred 1 hr further at −30 to −20° C., then slowly warmed up to RT and stirred for 3 days at rt. The reaction mixture was concentrated on the rotary evaporator. The residue was treated with 200 ml ethyl acetate and 75 ml sat. NaHCO$_3$ soln., well shaken and the aqueous phase further extracted 2× with 75 ml portions of ethyl acetate. The ethyl acetate phase was dried over Na$_2$SO$_4$ dried, filtered, concentrated and the residue dried at the oil pump: 1.92 g colourless and crystalline crude product. The crude product was purified by column chromatography (50 g column, mobile phase: gradient hexane:ethyl acetate 80% to 100% ethyl acetate): 1.66 g (97%).

$^1$H-NMR (400 MHz, DMSO-D6): 1.66 (m, 2H), 2.30 (m, 6H), 3.37 (m, 2H), 3.57 (m, 4H), 7.42 (t, 1H), 8.27 (s, 1H).

MS: 383 (MH+).

Intermediate 44.1

Preparation of (5-bromo-2-chloro-pyrimidine-4-yl)-(tetrahydro-pyran-4-yl)-amine

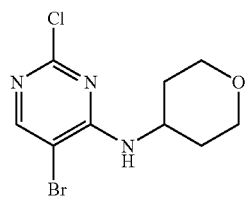

In the reaction of 5-bromo-2,4-dichloropyrimidine (300 mg, 1.32 mmol) with tetrahydropyran-4-ylamine (144 mg, 1.42 mmol) according to GP 2, the desired product is obtained in 83% yield (320 mg) after chromatographic purification (silica gel, ethyl acetate/hexane with ethyl acetate: 0-100%).

$^1$HNMR (300 MHz, DMSO): 1.64-1.72 (m, 4H), 3.33-3.80 (m, 2H), 3.82-3.86 (m, 2H), 4.06-4.14 (m, 1H), 7.38 (d, 1H), 8.22 (s, 1H).

Intermediate 44.2

Preparation of (RS)—N-(ethoxycarbonyl)-S-(4-{[4-{[tetrahydro-pyran-4-yl]amino}-5-bromopyrimindin-2-yl]amino}phenyl)-S-methylsulfoximide

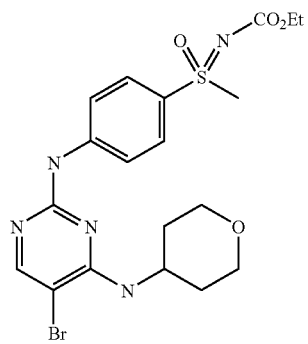 [SMILES: CCOC(=O)N=S(C)(=O)c1ccc(Nc2ncc(Br)c(NC3CCOCC3)n2)cc1]

In the reaction of (5-bromo-2-chloro-pyrimidine-4-yl)-(tetrahydro-pyran-4-yl)-amine (160 mg, 0.55 mmol) and (RS)—S-(4-aminophenyl)-N-(ethoxycarbonyl)-S-methyl-sulfoximide (110 mg, 0.46 mmol) according to GP 4, the desired product is obtained in 26% yield (70 mg) after chromatographic purification (silica gel, ethyl acetate/hexane with ethyl acetate: 0-100%, then methylene chloride).

$^1$HNMR (400 MHz, DMSO-D6): 1.06 (t, 3H), 1.60-1.80 (m, 4H), 3.38-3.45 (m, 5H), 3.85-3.91 (m, 4H), 4.10-4.20 (m, 1H), 6.81 (d, 1H), 7.77 (d, 2H), 7.94 (d, 2H), 8.09 (s, 1H), 9.83 (s, 1H).

Intermediate 45.1

Preparation of 2-chloro-5-iodo-4-methoxy-pyrimidine

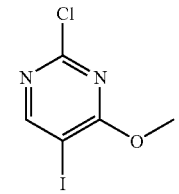

Methanolic sodium ethanolate solution (88.00 mL, 15.31 mmol—from 0.7 g sodium and 100 ml dry methanol) is added dropwise with stirring at −5 to 0° C. to a solution of 5-iodo-2,4-dichloropyrimidine (4.00 g, 14.55 mmol) in dry methanol (50 mL). The reaction solution is warmed to RT overnight, during which the crude product precipitates. The product is isolated by filtration and then stirred thoroughly with water (ca 50 mL) for 30 mins, recrystallised from methanol and dried over phosphorus pentoxide in the desiccator under vacuum: 2.18 g (8.06 mmol, 55.39%) of a white product.

$^1$H-NMR (300 MHz, CDCl$_3$): 4.08 (s, 3H), 8.60 (s, 1H).

Intermediate 45.2

Preparation of (RS)—N-(Ethoxycarbonyl)-S-(3-{[5-bromo-4-(methoxy)pyrimindin-2-yl]amino}phenyl)-S-methylsulfoximide

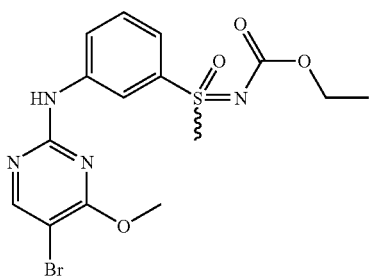 [SMILES: CCOC(=O)N=S(C)(=O)c1cccc(Nc2ncc(Br)c(OC)n2)c1]

Intermediate 45.2 was prepared in analogy to GP 4 by reaction of Intermediate 11 (1.73 g, 7.16 mmol) with commercial 5-bromo-2-chloro-4-methoxypyrimidine (2.00 g, 8.95 mmol, 1.25 eq) to give 1.33 g (43% yield) of Intermediate 45.2 (after crystallization from acetonitrile and column chromatography of the mother liquor residue).

$^1$H-NMR (DMSO, 300 MHz): 10.21 (s, 1 H); 8.67 (s br, 1 H); 8.42 (s, 1 H); 7.82 (d, 1 H); 7.56 (t, 1 H); 7.48 (d, 1 H); 4.02 (s, 3 H); 3.88 (mc, 2 H); 3.38 (s, 3 H); 1.04 (t, 3 H).

MS (ESI): [M+H]$^+$=429 ($^{79}$Br).

Intermediate 46.1

Preparation of 3-(5-Bromo-2-chloro-pyrimidin-4-yloxy)-propionic acid tert-butyl ester

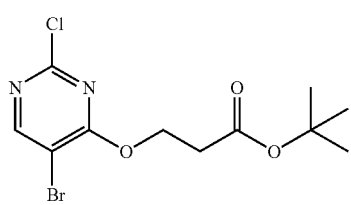 [SMILES: CC(C)(C)OC(=O)CCOc1nc(Cl)ncc1Br]

2,4-Dichloror-5-bromopyrimidine (7.98 g, 35 mmol) is dissolved in DMF (35 ml) and Cs$_2$CO$_3$ (11.4 g, 35 mmol) and 3-hydroxy-propionic acid tert-butyl-ester (5.12 g, 35 mmol) are added. The reaction mixture is stirred for 5 h at rt. The reaction mixture is diluted with brine and the extracted with ethyl acetate (3×). The organic layers are washed with brine, dried over sodium sulfate and evaporated to dryness. The crude product is used for the following reaction without any further purification.

$^1$H-NMR (300 MHz, DMSO-D$_6$): 1.35 (s, 9 H), 2.71 (t, 2H), 4.56 (t, 2H), 8.70 (s, 1H).

MS: 339 (MH+).

Intermediate 47.1

Preparation of 5-Bromo-2-chloro-4-methylsulfanyl-pyrimidine

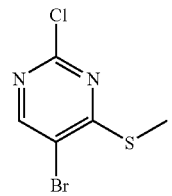

MeSNa (2 g, 28.5 mmol; 1 eq.) and 5-bromo-2,4-dichloropyrimidine (6.5 g, 28.5 mmol, 1 eq.) are stirred in dry acetonitrile (50 mL) at rt for 24 h. Then the mixture is poured into water, extracted with DCM, dried (Na$_2$SO$_4$) and evaporated to dryness. The product crystallised from hexane to yield 4.0 g of Intermediate 10 (70% yield).

$^1$H-NMR (400 MHz, CDCl$_3$): 8.31 (s, 1 H); 2.59 (s, 3 H).

Intermediate 47.2

Preparation of (RS)—N-(Ethoxycarbonyl)-S-(3-{[5-bromo-4-(methylsulfanyl)pyrimindin-2-yl]amino}phenyl)-S-methylsulfoximide

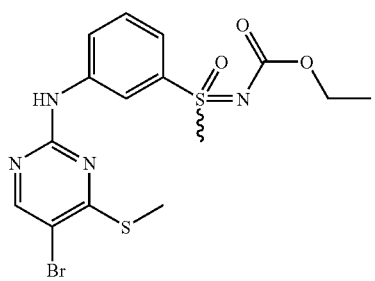 [SMILES: CCOC(=O)N=S(C)(=O)c1cccc(Nc2ncc(Br)c(SC)n2)c1]

Intermediate 47.2 was prepared in analogy to GP 4 by reaction of 2.15 g of Intermediate 11 (4.5 mmol, 1 eq.) and 1.09 g of Intermediate 47.1 (4.5 mmol, 1 eq.) to yield (after crystallization from acetonitrile) 1.2 g of Intermediate 47.2 (60% yield).

$^1$H-NMR (300 MHz, DMSO): 10.25 (s, 1 H); 8.60 (s, 1 H); 8.40 (s, 1 H); 7.90 (d, 1 H); 7.58 (t, 1 H); 7.50 (d, 1 H); 3.84-3.96 (m, 2 H); 3.40 (s, 3 H); 2.55 (s, 3 H); 1.10 (t, 3 H).

Intermediate 48.1

Preparation of (RS)—N-(ethoxycarbonyl)-(4-{[4-{methylsulfanyl}-5-bromo-pyrimidin-2-yl]amino}phenyl)-S-methylsulfoximide

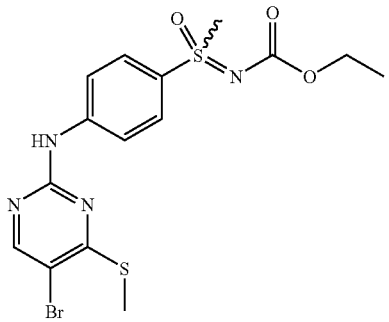 [SMILES: CCOC(=O)N=S(C)(=O)c1ccc(Nc2ncc(Br)c(SC)n2)cc1]

(RS)—S-(4-aminophenyl)-N-(ethoxycarbonyl)-S-methylsulfoximide (10 g, 42 mmol), 5-bromo-2-chloro-4-methylsulfanyl-pyrimidine (10 g, 42 mmol) and 5M HCl (8 mL) in dioxane is stirred at 60° C. in 90% acetonitrile-water (250 mL) for 36 h. TLC indicates almost complete consumption of starting sulfoximine. The reaction mixture is poured into 800 mL of aq. NaHCO$_3$, the pasty precipitate filtered, washed with 70 mL of EtOAc, then crude material (7.5 g) is recrystallized from boiling EtOH (200 mL) to yield 6 g (35%).

$^1$H-NMR (300 MHz, DMSO-D$_6$): 1.10 (t, 3H), 2.60 (s, 3H), 3.42 (s, 3H), 3.90 (m, 2H), 7.95 (d, 2H), 7.85 (d, 2H), 8.40 (s, 1H), 10.35 (s, 1H).

Intermediate 49.0

Preparation of 5-bromo-2-methylsulfonylpyrimidine

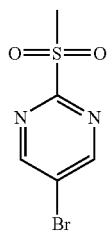

To a solution of 5-bromo-2-methylsulfanylpyrimidine (10.0 g, 48.8 mmol) in methanol (195 mL) were added a solution of Oxone® (94.6 g, 154 mmol, 3.16 eq) in water (500 mL and aq. 4 N sodium hydroxide (40 mL, 160 mmol, 3.28 eq.) portionwise and in an alternating addition mode to maintain pH between 2 and 3 at a temperature of 0° C. After complete addition, the mixture was allowed to stir for 2 h at room temperature. Water (500 mL) was added, and the mixture was extracted with ethyl acetate (2×500 mL). The aqueous layer was adjusted to pH 7 by addition of aq. sodium hydroxide, and was again extracted with ethyl acetate. The combined organic layers were dried over MgSO$_4$ and evaporated to give 9.23 g (80% yield) of the desired sulfone which was used without further purification.

$^1$H-NMR (300 MHz, DMSO): 9.28 (s, 2 H); 3.37 (s, 3 H).

MS (ESI): [M+H]$^+$=237 ($^{79}$Br).

Intermediate 49.1

Preparation of (RS)—N-(ethoxycarbonyl)-S-(3-{[5-bromo-pyrimindin-2-yl]amino}phenyl)-S-methylsulfoximide

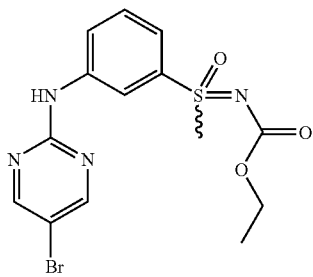 [SMILES: CCOC(=O)N=S(C)(=O)c1cccc(Nc2ncc(Br)cn2)c1]

To a solution of Intermediate 11 (2.42 g, 10.0 mmol) in DMF (100 mL) was added sodium hydride (479 mg of a 60% suspension in mineral oil, 12.0 mmol) at a temperature of −20° C. under an atmosphere of nitrogen. The resulting mixture was stirred at −20° C. for 15 minutes, after which Intermediate 49.0 (2.96 g, 12.5 mmol) was added. The mixture was stirred for 4 h at said temperature and then evaporated. The residue was partitioned between water (100 mL) and ethyl acetate (25 mL). The organic layer was again washed with water (25 mL), dried over MgSO$_4$, and evaporated. Column chromatography of the residue yielded 730 mg (18% yield) of the title compound.

$^1$H-NMR (400 MHz, DMSO): 10.27 (s, 1 H); 8.63 (s, 2 H); 8.31 (mc, 1 H); 8.03 (d br, 1 H); 7.57 (t, 1 H); 7.48 (d br, 1 H); 3.88 (mc, 2 H); 3.39 (s, 3 H); 1.05 (t, 3 H).

MS (ESI): [M+H]$^+$=399 ($^{79}$Br).

Intermediate 49.2

Preparation of (RS)—S-(3-{[5-bromo-pyrimindin-2-yl]amino}phenyl)-S-methylsulfoximide

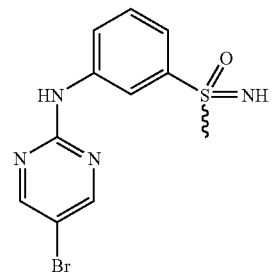 [SMILES: CS(=N)(=O)c1cccc(Nc2ncc(Br)cn2)c1]

Intermediate 49.2 was prepared in analogy to GP 6 from Intermediate 49.1 in 89% yield.

$^1$H-NMR (400 MHz, DMSO): 10.17 (s, 1 H); 8.62 (s, 2 H); 8.28 (s, 1 H); 7.89-7.98 (m, 1 H); 7.44-7.52 (m, 2 H); 4.11 (s, 1 H); 3.00 (s, 3 H).

MS (ESI): [M+H]$^+$=327 ($^{79}$Br).

Preparation of the (Hetero)Aryl Alkyne Intermediates

Intermediate 50

Preparation of 6-ethynyl-1H-indazole

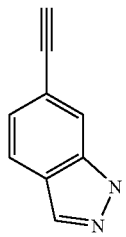

Step 1:

6-Iodo-1H-indazole (1.00 g, 4.10 mmol) was reacted with trimethylsilyl acetylene (0.61 mL, 4.30 mmol) in analogy to GP8a to give 675 mg (77%) of pure 6-(trimethylsilyl)ethynyl-1H-indazole.

$^1$H-NMR (300 MHz, DMSO): 13.17 (s br, 1 H); 8.07 (s, 1 H); 7.71 (d, 1 H); 7.59 (s, 1 H); 7.08 (d, 1 H); 0.21 (s, 9 H).

Step 2:

Intermediate 50 was prepared in analogy to GP9 from the product obtained in step 1 in quantitative yield.

$^1$H-NMR (300 MHz, DMSO): 13.22 (s br, 1 H); 8.12 (s, 1 H); 7.79 (d, 1 H); 7.68 (s, 1 H); 7.17 (d, 1 H); 4.21 (s, 1 H).

MS (ESI): [M+H]$^+$=143.

Intermediate 51

Preparation of 5-ethynyl-1H-indazole

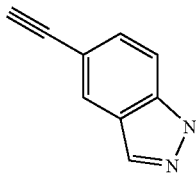

Step 1:

In an adaption of GP 8a, 5-Iodo-1H-indazole (0.98 g, 4.02 mmol) was reacted with trimethylsilyl acetylene (0.60 mL, 4.22 mmol) at 90° C. for 5 h to give 395 mg (46%) of pure 5-(trimethylsilyl)ethynyl-1H-indazole.

$^1$H-NMR (300 MHz, DMSO): 13.23 (s br, 1 H); 8.04 (s, 1 H); 7.89 (s, 1 H); 7.49 (d, 1 H); 7.32 (d, 1 H); 0.20 (s, 9 H).

Step 2:

Intermediate 51 was prepared in analogy to GP9 from the product obtained in step 1 in quantitative yield.

$^1$H-NMR (300 MHz, DMSO): 13.22 (s br, 1 H); 8.07 (s, 1 H); 7.91 (s, 1 H); 7.51 (d, 1 H); 7.37 (d, 1 H); 4.00 (s, 1 H).

MS (ESI): [M+H]$^+$=143.

Intermediate 52

Preparation of 4-ethynyl-1H-indazole

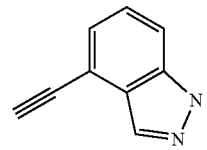

Step 1:

In an adaption of GP 8a, 4-Iodo-1H-indazole (1.00 g, 4.10 mmol) was reacted with trimethylsilyl acetylene (0.61 mL, 4.30 mmol) at 90° C. for 5 h to give 498 mg (57%) of pure 4-(trimethylsilyl)ethynyl-1H-indazole.

$^1$H-NMR (300 MHz, DMSO): 13.29 (s br, 1 H); 8.01 (s, 1 H); 7.55 (d, 1 H); 7.31 (t, 1 H); 7.21 (d, 1 H); 0.25 (s, 9 H).

Step 2:

Intermediate 52 was prepared in analogy to GP9 from the product obtained in step 1 in quantitative yield.

$^1$H-NMR (300 MHz, DMSO): 13.30 (s br, 1 H); 8.06 (s, 1 H); 7.59 (d, 1 H); 7.18-7.38 (m, 2 H); 4.44 (s, 1 H).

MS (ESI): [M+H]$^+$=143.

Intermediate 53

Preparation of N-methyl-3-[(trimethylsilyl)ethynyl]benzamide

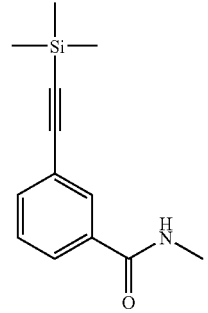

Step 1:

To a cooled (0° C.) solution of 3-iodobenzoyl chloride (2.66 g; 10.0 mmol) in DCM (10 mL) was slowly added a 2 M solution of methylamine in THF (10 mL, 2.0 eq.). Upon completion of the addition, the ice bath was removed and the mixture was stirred overnight. All volatiles were removed in vacuo and the residue was treated with aq. NaHCO$_3$ (25 mL) and subsequently extracted with ethyl acetate (3×15 mL). The combined organic layers were dried over MgSO$_4$ and evaporated. The crude product was purified by column chromatography on silica gel to give the desired 3-iodo-N-methylbenzamide (0.67 g, 26% yield).

$^1$H-NMR (400 MHz, DMSO): 8.42-8.56 (m, 1 H); 8.13 (s, 1 H); 7.77-7.89 (m, 2 H); 7.24 (t, 1 H); 2.73 (d, 3 H).

MS (ESI): [M+H]$^+$=262.

Step 2:

Intermediate 53 was prepared in analogy to GP8d in 95% yield from 3-iodo-N-methylbenzamide obtained in step 1.

$^1$H-NMR (400 MHz, DMSO): 8.52 (q br, 1 H); 7.88 (s br, 1 H); 7.82 (d br, 1 H); 7.56 (d br, 1 H); 7.42 (t, 1 H); 2.74 (d, 3 H); 0.21 (s, 9 H)

MS (ESI): [M+H]$^+$=232.

Intermediate 54

Preparation of N-{4-methyl-3-[(trimethylsilyl)ethynyl]phenyl}methanesulfonamide

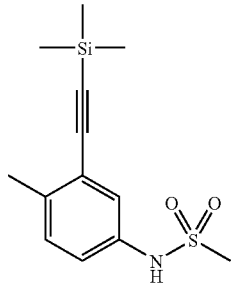

Step 1:
To a solution of 3-iodo-4-methyl aniline (1.17 g, 5.00 mmol) in pyridine (2.5 mL) was added methanesulfonyl chloride (429 µL, 1.10 eq.) at a temperature of 0° C. The mixture was stirred overnight at room temperature and was then evaporated. The residue was treated with 2 N aq. HCl (25 mL) and subsequently extracted with ethyl acetate (2×30 mL). The combined organic layers were dried over MgSO$_4$ and evaporated to give the desired methanesulfonamide in quantitative yield. It was used in step 2 without further purification.

$^1$H-NMR (300 MHz, DMSO): 9.74 (s br, 1 H); 7.67 (d, 1 H); 7.30 (d, 1 H); 7.18 (dd, 1 H); 2.97 (s, 3 H); 2.32 (s, 3 H).

Step 2:
Intermediate 54 was prepared in analogy to GP8d in 61% yield from N-(3-iodo-4-methylphenyl)methanesulfonamide obtained in step 1.

$^1$H-NMR (300 MHz, DMSO): 9.64 (s, 1 H); 7.16-7.25 (m, 2 H); 7.10 (dd, 1 H); 2.91 (s, 3 H); 2.28 (s, 3 H); 0.21 (s, 9 H).
MS (ESI): [M+H]$^+$=282.

Intermediate 55

Preparation of N-(3-ethynylphenyl)methanesulfonamide

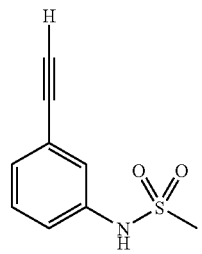

To a solution of 3-ethynyl aniline (1.05 mL, 10.0 mmol) in pyridine (5 mL) was added methanesulfonyl chloride (857 µL, 1.10 eq.) at a temperature of 0° C. The resulting mixture was stirred overnight at room temperature and was then evaporated. The residue was treated with 2 N aq. HCl (25 mL) and subsequently extracted with ethyl acetate (2×30 mL). The combined organic layers were dried over MgSO$_4$ and evaporated to give the desired methanesulfonamide in quantitative yield. It was used without further purification.

$^1$H-NMR (300 MHz, DMSO): 9.87 (s, 1 H); 7.29-7.37 (m, 1 H); 7.11-7.28 (m, 3 H); 4.18 (s, 1 H); 2.98 (s, 3 H).
MS (ESI): [M−H]$^−$=194.

Intermediate 56

Preparation of N,4-dimethyl-3-[(trimethylsilyl)ethynyl]benzamide

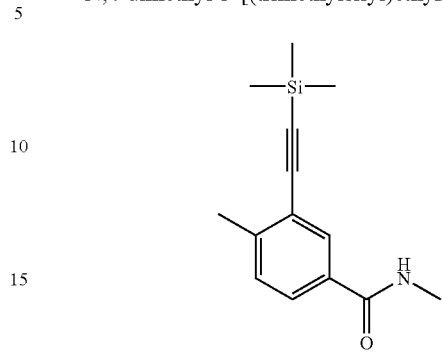

Step 1:
To a cooled (0° C.) solution of 3-iodo-4-methylbenzoyl chloride (2.80 g; 10.0 mmol) in DCM (10 mL) was slowly added a 2 M solution of methylamine in THF (11 mL, 2.2 eq.). Upon completion of the addition, the ice bath was removed and the mixture was stirred overnight. All volatiles were removed in vacuo and the residue was treated with aq. NaHCO$_3$ (25 mL) and subsequently extracted with ethyl acetate (3×15 mL). The combined organic layers were dried over MgSO$_4$ and evaporated. The target compound 3-iodo-N,4-dimethylbenzamide (2.62 g, 95% yield) was used without further purification.

$^1$H-NMR (300 MHz, DMSO): 8.39-8.53 (m, 1 H); 8.22 (d, 1 H); 7.73 (dd, 1 H); 7.38 (d, 1 H); 2.72 (d, 3 H); 2.36 (s, 3 H).
MS (ESI): [M+H]$^+$=276.

Step 2:
Intermediate 56 was obtained according to GP8d in 87% yield from 3-iodo-N,4-dimethylbenzamide prepared in step 1.

$^1$H-NMR (300 MHz, DMSO): 8.42 (q br, 1 H); 7.85 (d, 1 H); 7.72 (dd, 1 H); 7.34 (d, 1 H); 2.74 (d, 3 H); 2.38 (s, 3 H); 0.21 (s, 9 H).
MS (ESI): [M+H]$^+$=246.

Intermediate 57

Preparation of 4-[(trimethylsilyl)ethynyl]pyridin-2-ol

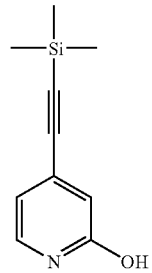

In an adaption of GP 8d, 4-bromopyridin-2-ol was reacted with trimethylsilyl acetylene (1.5. eq) for 2 h at 90° C. to give Intermediate 57 in 49% yield.

$^1$H-NMR (300 MHz, DMSO): 11.66 (s br, 1 H); 7.32 (d, 1 H); 6.34 (d, 1 H); 6.08 (dd, 1 H); 0.18 (s, 9 H).
MS (ESI): [M+H]$^+$=192.

Synthesis of Example Compounds

Example Compound 1.1

Preparation of (RS)—S-(4-[4-((R)-2-Hydroxy-1-methyl-ethylamino)-5-(4-methoxy-phenylethynyl)-pyrimidin-2-ylamino]-phenyl)-S-methylsulfoximide

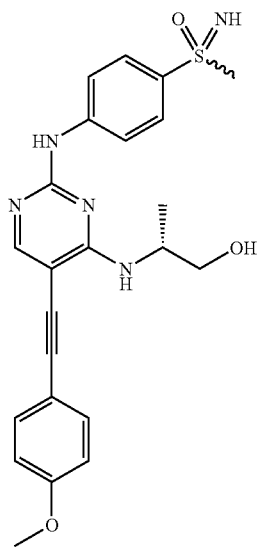

In analogy to GP 8a, 89.5 mg of Intermediate 37 (0.2 mmol, 1 eq.), 7.6 mg CuI (0.04 mmol, 0.2 eq.) and 14.4 mg Pd(PPh$_3$)$_2$ Cl$_2$ (0.02 mmol, 0.1 eq.) were weighed into a Schlenk flask, set under an atmosphere of argon and dissolved in 2 mL dry DMF. 31 µL 1-Ethynyl-4-methoxy-benzene (0.24 mmol, 1.2 eq.) and 280 µL triethylamine (2 mmol, 10 eq.) were added sequentially and the resulting mixture was stirred at rt for 4 h. The reaction mixture was partitioned between DCM and water, the aqueous layer was extracted with DCM (3×) and the combined organic layers were dried and concentrated in vacuo. The target compound was isolated by preparative HPLC purification using the following conditions:

Column: XBridge C18 5µ 150×19 mm
Solvent: A:H2O B:Acetonitril
Buffer: A/0.2% NH3
Gradient: 80% A+20% B(2')_20->50% B(10')_50->99% B(0.5')
Flow: 20.0 mL/min
Solution: 102 mg/4 mL DMSO
Injection Volume: 1×2.0 mL
Detection: DAD (210-500 nm) TAC; MS-ESI+ (125-800 m/z) TIC
Temperature: Rt $^1$H-NMR (DMSO, 300 MHz): 9.85 (s, 1 H); 8.17 (s, 1 H); 7.99 (d, 2 H); 7.82 (d, 2 H); 7.52 (d, 2 H); 7.00 (d, 2 H); 6.48 (d, 1 H); 4.96 (br. s, 1 H); 4.30 (mc, 1 H); 3.81 (s, 3 H); 3.52-3.62 (m, 2 H); 3.08 (s, 3 H); 1.26 (d, 3 H).

MS (ESI): [M+H]$^+$=452.

The following example compounds 1.2 to 1.33 were prepared in analogy to Example compound 1 and GP 8a by Sonogashira coupling of the respective halo pyrimidine intermediates 35.1, 36, 37, 38.3, and 39.3 with the respective alkynes. The respective alkynes were either commercially available or were prepared from, for example, (hetero)aryl halides as described above or by standard transformations as known to the person skilled in the art (see e.g. Intermediates 50 to 57).

| Example | Structure | Name | Analytical data |
|---|---|---|---|
| 1.2 | 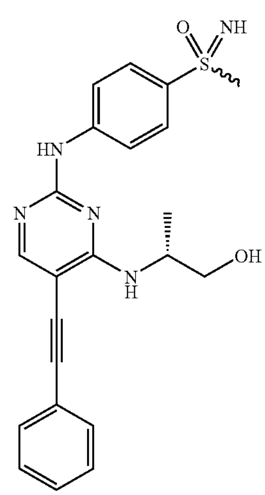 [SMILES: C[C@H](CO)Nc1nc(Nc2ccc(S(C)(=N)=O)cc2)ncc1C#Cc1ccccc1] | (RS)-S-(4-[4-((R)-2-Hydroxy-1-methyl-ethylamino)-5-(phenylethynyl)-pyrimidin-2-ylamino]-phenyl)-S-methylsulfoximide | $^1$H-NMR: (d6-DMSO, 300 MHz) 9.88 (s, 1H); 8.20 (s, 1H); 7.98 (d, 2H); 7.81 (d, 2H); 7.55-7.62 (m, 2H); 7.39-7.49 (m, 3H); 6.54 (d, 1H); 4.98 (t, 1H); 4.31 (mc, 1H); 4.01 (s, 1H); 3.58 (mc, 2H); 3.03 (s, 3H); 1.26 (d, 3H). MS (ESI): [M + H]$^+$ = 422. |

| Example | Structure | Name | Analytical data |
|---------|-----------|------|-----------------|
| 1.3 | 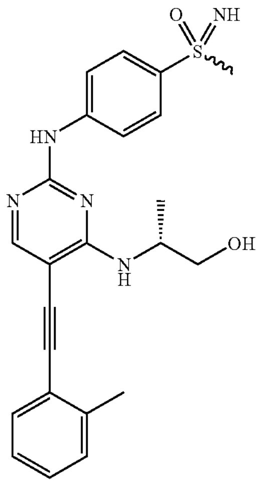 [SMILES: Cc1ccccc1C#Cc1cnc(Nc2ccc(S(C)(=N)=O)cc2)nc1N[C@H](C)CO] | (RS)-S-(4-[4-((R)-2-Hydroxy-1-methyl-ethylamino)-5-(2-methyl-(phenylethynyl)-pyrimidin-2-ylamino]-phenyl)-S-methylsulfoximide | $^1$H-NMR: (d6-DMSO, 300 MHz) 9.90 (s, 1H); 8.22 (s, 1H); 7.99 (d, 2H); 7.82 (d, 2H); 7.54 (d, 1H); 7.22-7.36 (m, 3H); 6.40 (d, 1H); 4.98 (t, 1H); 4.30 (mc, 1H); 4.00 (s, 1H); 3.57 (t, 2H); 3.04 (s, 3H); 2.47 (s, 3H); 1.26 (d, 3H). MS (ESI): $[M + H]^+ = 436$. |
| 1.4 | 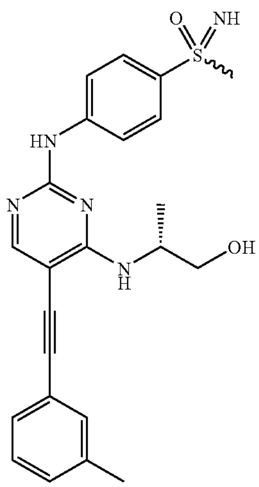 [SMILES: Cc1cccc(C#Cc2cnc(Nc3ccc(S(C)(=N)=O)cc3)nc2N[C@H](C)CO)c1] | (RS)-S-(4-[4-((R)-2-Hydroxy-1-methyl-ethylamino)-5-(3-methyl-(phenylethynyl)-pyrimidin-2-ylamino]-phenyl)-S-methylsulfoximide | $^1$H-NMR: (d6-DMSO, 300 MHz) 9.87 (s, 1H); 8.19 (s, 1H); 7.98 (d, 2H); 7.81 (d, 2H); 7.36-7.41 (m, 2H); 7.32 (t, 1H); 7.22 (d, 1H); 6.51 (d, 1H); 4.98 (t, 1H); 4.31 (mc, 1H); 4.01 (s, 1H); 3.58 (mc, 2H); 3.03 (s, 3H); 2.34 (s, 3H); 1.26 (d, 3H). MS (ESI): $[M + H]^+ = 436$. |
| 1.5 | 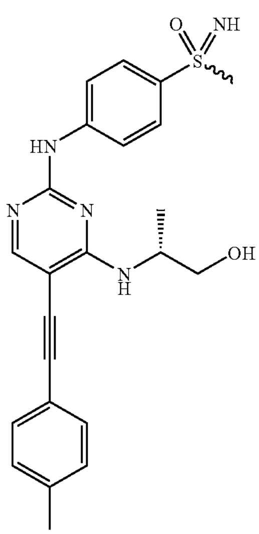 [SMILES: Cc1ccc(C#Cc2cnc(Nc3ccc(S(C)(=N)=O)cc3)nc2N[C@H](C)CO)cc1] | (RS)-S-(4-[4-((R)-2-Hydroxy-1-methyl-ethylamino)-5-(4-methyl-(phenylethynyl)-pyrimidin-2-ylamino]-phenyl)-S-methylsulfoximide | $^1$H-NMR: (d6-DMSO, 300 MHz) 9.85 (s, 1H); 8.18 (s, 1H); 7.98 (d, 2H); 7.81 (d, 2H); 7.47 (d, 2H); 7.25 (d, 2H); 6.50 (d, 1H); 4.97 (t, 1H); 4.30 (mc, 1H); 4.00 (s, 1H); 3.58 (t, 2H); 3.04 (s, 3H); 2.35 (s, 3H); 1.26 (d, 3H). MS (ESI): $[M + H]^+ = 436$. |

| Example | Structure | Name | Analytical data |
|---|---|---|---|
| 1.6 | 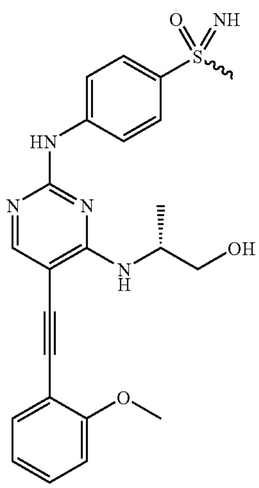 [SMILES: COc1ccccc1C#Cc1cnc(Nc2ccc(S(C)(=N)=O)cc2)nc1N[C@H](C)CO] | (RS)-S-(4-[4-((R)-2-Hydroxy-1-methyl-ethylamino)-5-(2-methoxy-(phenylethynyl)-pyrimidin-2-ylamino]-phenyl)-S-methylsulfoximide | $^1$H-NMR: (d6-DMSO, 300 MHz) 9.88 (s, 1H); 8.18 (s, 1H); 7.98 (d, 2H); 7.82 (d, 2H); 7.47 (dd, 1H); 7.39 (t, 1H); 7.12 (d, 1H); 7.00 (t, 1H); 6.31 (d, 1H); 5.01 (t, 1H); 4.32 (mc, 1H); 4.00 (s, 1H); 3.91 (s, 3H); 3.58 (t, 2H); 3.03 (s, 3H); 1.29 (d, 3H). MS (ESI): [M + H]$^+$ = 452. |
| 1.7 | 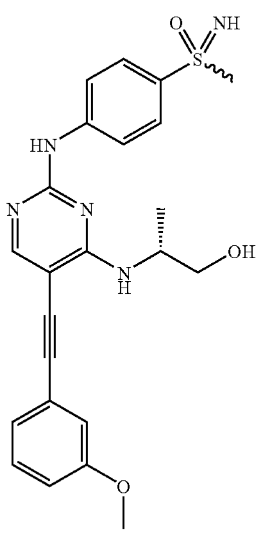 [SMILES: COc1cccc(C#Cc2cnc(Nc3ccc(S(C)(=N)=O)cc3)nc2N[C@H](C)CO)c1] | (RS)-S-(4-[4-((R)-2-Hydroxy-1-methyl-ethylamino)-5-(3-methoxy-(phenylethynyl)-pyrimidin-2-ylamino]-phenyl)-S-methylsulfoximide | $^1$H-NMR: (d6-DMSO, 300 MHz) 9.87 (s, 1H); 8.20 (s, 1H); 7.99 (d, 2H); 7.82 (d, 2H); 7.35 (t, 1H); 7.13-7.17 (m, 2H); 6.99 (dd, 1H); 6.53 (d, 1H); 4.98 (t, 1H); 4.30 (mc, 1H); 4.00 (s, 1H); 3.80 (s, 3H); 3.58 (mc, 2H); 3.03 (s, 3H); 1.26 (d, 3H). MS (ESI): [M + H]$^+$ = 452. |
| 1.8 | 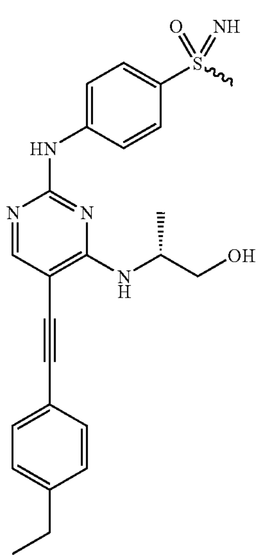 [SMILES: CCc1ccc(C#Cc2cnc(Nc3ccc(S(C)(=N)=O)cc3)nc2N[C@H](C)CO)cc1] | (RS)-S-(4-[5-(4-Ethyl-phenylethynyl)-4-((R)-2-hydroxy-1-methyl-ethylamino)-pyrimidin-2-ylamino]-phenyl)-S-methylsulfoximide | $^1$H-NMR: (d6-DMSO, 300 MHz) 9.86 (s, 1H); 8.18 (s, 1H); 7.99 (d, 2H); 7.81 (d, 2H); 7.49 (d, 2H); 7.28 (d, 2H); 6.49 (d, 1H); 4.97 (t, 1H); 4.31 (mc, 1H); 4.00 (s, 1H); 3.57 (mc, 2H); 3.03 (s, 3H); 2.65 (q, 2H); 1.26 (d, 3H); 1.20 (t, 3H). MS (ESI): [M + H]$^+$ = 450. |

| Example | Structure | Name | Analytical data |
|---|---|---|---|
| 1.9 | 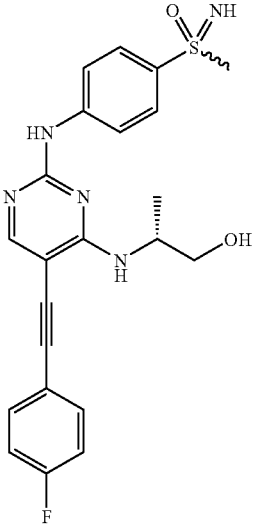 [SMILES: C[C@H](CO)Nc1nc(Nc2ccc(S(C)(=N)=O)cc2)ncc1C#Cc1ccc(F)cc1] | (RS)-S-(4-[5-(4-Fluoro-phenyl-ethynyl)-4-((R)-2-hydroxy-1-methyl-ethylamino)-pyrimidin-2-ylamino]-phenyl)-S-methylsulfoximide | $^1$H-NMR: (d6-DMSO, 300 MHz) 9.82 (s, 1H); 8.15 (s, 1H); 7.93 (d, 2H); 7.77 (d, 2H); 7.60 (dd, 2H); 7.24 (7, 2H); 6.51 (d, 1H); 4.91 (t, 1H); 4.26 (mc, 1H); 3.96 (s, 1H); 3.52 (mc, 2H); 2.98 (s, 3H); 1.21 (d, 3H). MS (ESI): $[M + H]^+ = 440$. |
| 1.10 | 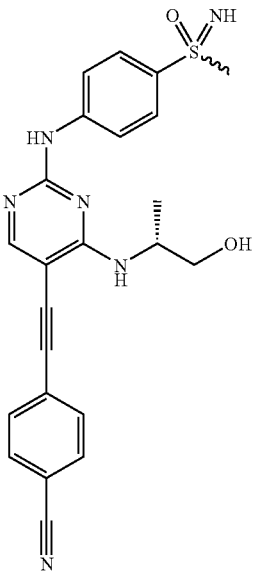 [SMILES: C[C@H](CO)Nc1nc(Nc2ccc(S(C)(=N)=O)cc2)ncc1C#Cc1ccc(C#N)cc1] | (RS)-S-(4-[5-(4-Cyano-phenyl-ethynyl)-4-((R)-2-hydroxy-1-methyl-ethylamino)-pyrimidin-2-ylamino]-phenyl)-S-methylsulfoximide | $^1$H-NMR: (d6-DMSO, 400 MHz) 9.92 (s, 1H); 8.20 (s, 1H); 7.93 (d, 2H); 7.86 (d, 2H); 7.78 (d, 2H); 7.71 (d, 2H); 6.65 (d, 1H); 4.92 (t, 1H); 4.28 (mc, 1H); 3.98 (s, 1H); 3.37-3.59 (m, 2H); 2.98 (s, 3H); 1.22 (d, 3H). MS (ESI): $[M + H]^+ = 447$. |

| Example | Structure | Name | Analytical data |
|---|---|---|---|
| 1.11 | 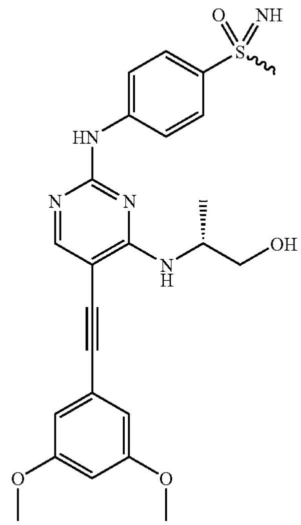 [SMILES: COc1cc(C#Cc2cnc(Nc3ccc(S(C)(=N)=O)cc3)nc2N[C@H](C)CO)cc(OC)c1] | (RS)-S-(4-[5-(3,5-Dimethoxy-phenylethynyl)-4-((R)-2-hydroxy-1-methyl-ethylamino)-pyrimidin-2-ylamino]-phenyl)-S-methylsulfoximide | $^1$H-NMR: (d6-DMSO, 300 MHz) 9.88 (s, 1H); 8.20 (s, 1H); 7.98 (d, 2H); 7.82 (d, 2H); 6.75 (d, 2H); 6.56 (t, 1H); 6.54 (d, 1H); 4.99 (t, 1H); 4.30 (mc, 1H); 4.00 (s, 1H); 3.58 (mc, 2H); 3.03 (s, 3H); 1.27 (d, 3H). MS (ESI): [M + H]$^+$ = 482. |
| 1.12 | 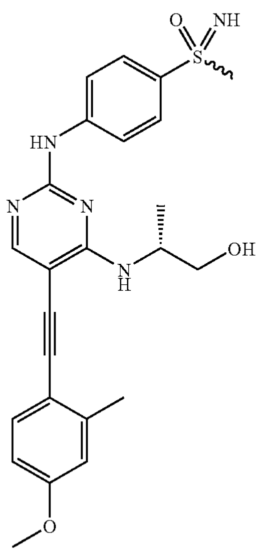 [SMILES: COc1ccc(C#Cc2cnc(Nc3ccc(S(C)(=N)=O)cc3)nc2N[C@H](C)CO)c(C)c1] | (RS)-S-(4-[4-((R)-2-Hydroxy-1-methyl-ethylamino)-5-(4-methoxy-2-methyl-phenylethynyl)-pyrimidin-2-ylamino]-phenyl)-S-methylsulfoximide | $^1$H-NMR: (d6-DMSO, 300 MHz) 9.81 (s, 1H); 8.13 (s, 1H); 7.94 (d, 2H); 7.76 (d, 2H); 7.42 (d, 1H); 6.88 (d, 2H); 6.78 (dd, 1H); 6.31 (d, 1H); 4.93 (t, 1H); 4.24 (mc, 1H); 3.95 (s, 1H); 3.74 (s, 3H); 3.52 (t, 2H); 2.98 (s, 3H); 2.40 (s, 3H); 1.21 (d, 3H). MS (ESI): [M + H]$^+$ = 466. |
| 1.13 | 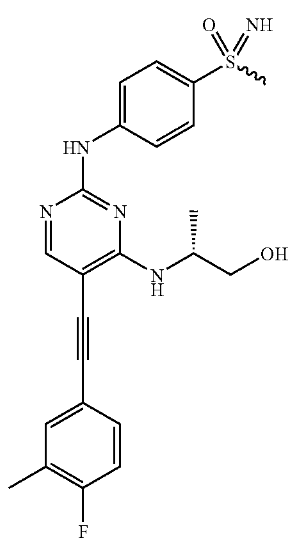 [SMILES: Cc1cc(C#Cc2cnc(Nc3ccc(S(C)(=N)=O)cc3)nc2N[C@H](C)CO)ccc1F] | (RS)-S-(4-[5-(4-Fluoro-3-methyl-phenyl-ethynyl)-4-((R)-2-hydroxy-1-methyl-ethylamino)-pyrimidin-2-ylamino]-phenyl)-S-methylsulfoximide | $^1$H-NMR: (d6-DMSO, 300 MHz) 9.86 (s, 1H); 8.18 (s, 1H); 7.98 (d, 2H); 7.81 (d, 2H); 7.53 (dd, 1H); 7.41-7.48 (m, 1H); 7.22 (dd, 1H); 6.53 (d, 1H); 4.97 (t, 1H); 4.30 (mc, 1H); 4.00 (s, 1H); 3.57 (mc, 2H); 3.03 (s, 3H); 2.27 (s, 3H); 1.27 (d, 3H). MS (ESI): [M + H]$^+$ = 454. |

| Example | Name | Analytical data |
|---|---|---|
| 1.14 | (RS)-S-(4-[4-((R)-2-Hydroxy-1-methyl-ethylamino)-5-(3-hydroxy-phenylethynyl)-pyrimidin-2-ylamino]-phenyl)-S-methylsulfoximide | $^1$H-NMR: (d6-DMSO, 400 MHz) 9.83 (s, 1H); 9.67 (br. s, 1H); 8.14 (s, 1H); 7.93 (d, 2H); 7.77 (d, 2H); 7.17 (t, 1H); 6.95 (d, 1H); 6.91 (d, 1H); 6.76 (dd, 1H); 6.46 (d, 1H); 4.94 (t, 1H); 4.25 (mc, 1H); 3.96 (s, 1H); 3.52 (mc, 2H); 2.98 (s, 3H); 1.21 (d, 3H). MS (ESI): [M + H]$^+$ = 438. |
| 1.15 | (RS)-S-(3-[4-((R)-2-Hydroxy-1-methyl-ethylamino)-5-(3-hydroxy-phenylethynyl)-pyrimidin-2-ylamino]-phenyl)-N-(isopropylcarbamoyl)-S-methylsulfoximide | $^1$H-NMR: (d6-DMSO, 400 MHz) 9.85 (s, 1H); 9.68 (s, 1H); 8.65 (s, 1H); 8.16 (s, 1H); 7.86 (d, 1H); 7.52 (t, 1H); 7.45 (d, 1H); 7.21 (t, 1H); 6.98 (d, 1H); 6.94 (s, 1H); 6.81 (m, 2H); 6.46 (m, 1H); 4.94 (m, 1H); 4.35 (m, 1H); 3.55 (m, 2H); 3.44 (m, 1H); 3.34 (d, 3H); 1.23 (d, 3H); 1.00 (m, 6H) MS (ESI): [M + H]$^+$ = 523. |
| 1.16 | (RS)-S-(3-[4-((R)-2-Hydroxy-1-methyl-ethylamino)-5-(phenylethynyl)-pyrimidin-2-ylamino]-phenyl)-S-methylsulfoximide | $^1$H-NMR: (d6-DMSO, 400 MHz) 9.91 (s, 1H); 8.73 (s br, 1H); 8.16 (s, 1H); 7.79-7.88 (m, 1H); 7.48-7.58 (m, 4H); 7.33-7.44 (m, 3H); 6.57 (d br, 1H); 4.34 (mc, 1H); 3.45-3.58 (m, 2H), 3.30-3.32 (2s, 3H); 1.18 (d, 3H). MS (ESI): [M − H]$^-$ = 420. |

-continued

| Example | Structure | Name | Analytical data |
|---|---|---|---|
| 1.17 | 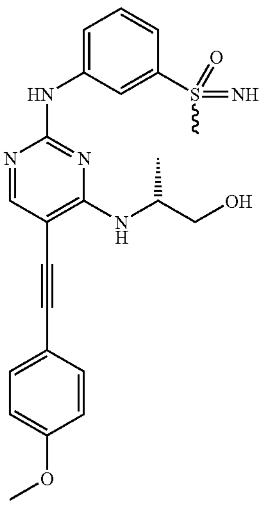 | (RS)-S-(3-[4-((R)-2-Hydroxy-1-methyl-ethylamino)-5-(4-methoxy-phenylethynyl)-pyrimidin-2-ylamino]-phenyl)-S-methylsulfoximide | $^1$H-NMR: (d6-DMSO, 300 MHz) 9.79 (s, 1H); 8.72 (d br, 1H); 8.15 (s, 1H); 7.73-7.84 (m, 1H); 7.42-7.56 (m, 4H); 7.01 (d, 2H); 6.43 (t, 1H); 4.94-5.08 (m, 1H); 4.40 (mc, 1H); 4.21 (s br, 1H); 3.81 (s, 3H); 3.45 (mc, 2H); 3.03 (s, 3H); 1.14 (d, 3H). MS (ESI): [M − H]$^−$ = 450. |
| 1.18 | 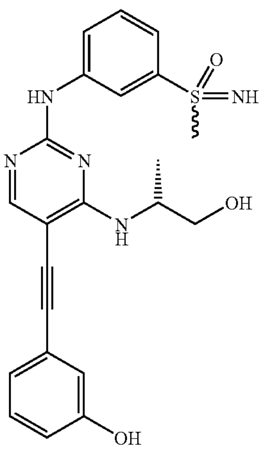 | (RS)-S-(3-[4-((R)-2-Hydroxy-1-methyl-ethylamino)-5-(3-hydroxy-phenylethynyl)-pyrimidin-2-ylamino]-phenyl)-S-methylsulfoximide | $^1$H-NMR: (d6-DMSO, 400 MHz) 9.76 (s, 1H); 9.63 (s, 1H); 8.68 (d br, 1H); 8.12 (s, 1H); 7.68-7.80 (m, 1H); 7.39-7.52 (m, 2H); 7.18 (t, 1H); 6.95 (d, 1H); 6.89-6.92 (m, 1H); 6.74 (mc, 1H); 6.41 (t, 1H); 4.92-5.03 (m, 1H); 4.37 (mc, 1H); 4.15 (mc, 1H); 3.40-3.59 (m, 2H); 3.00 (s, 3H); 1.20 (d, 3H). MS (ESI): [M − H]$^−$ = 436. |
| 1.19 | 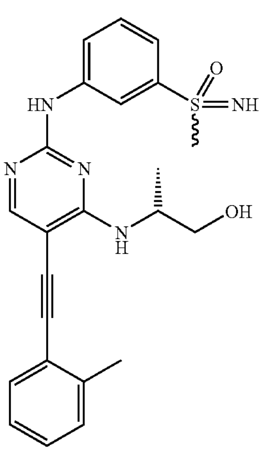 | (RS)-S-(3-[4-((R)-2-Hydroxy-1-methyl-ethylamino)-5-(2-methyl-phenylethynyl)-pyrimidin-2-ylamino]-phenyl)-S-methylsulfoximide | $^1$H-NMR: (d6-DMSO, 400 MHz) 9.82 (s, 1H); 8.71 (s br, 1H) 8.17 (s, 1H); 7.71-7.82 (m, 1H); 7.42-7.52 (m, 3H); 7.17-7.33 (m, 3H); 6.34 (t, 1H); 4.97 (s br, 1H); 4.37 (mc, 1H); 3.43-3.58 (m, 2H); 3.05 (s, 3H); 2.42 (s, 3H); 1.20 (d, 3H). MS (ESI): [M − H]$^−$ = 434. |

-continued

| Example | Structure | Name | Analytical data |
|---|---|---|---|
| 1.20 | 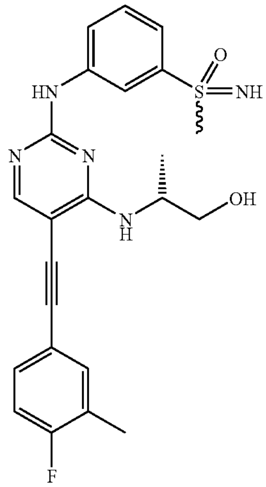 | (RS)-S-(3-[5-(4-Fluoro-3-methyl-phenyl-ethynyl)-4-((R)-2-hydroxy-1-methyl-ethylamino)-pyrimidin-2-ylamino]-phenyl)-S-methylsulfoximide | $^1$H-NMR: (d6-DMSO, 400 MHz) 9.78 (s, 1H); 8.68 (d br, 1H); 8.12 (s, 1H); 7.69-7.82 (m, 1H); 7.36-7.52 (m, 4H); 7.17 (t, 1H); 6.44 (t, 1H); 4.95 (s br, 1H); 4.36 (mc, 1H); 3.42-3.60 (m, 2H); 3.07 (s, 3H); 2.22 (s, 3H); 1.19 (d, 3H). MS (ESI): $[M - H]^- = 452$. |
| 1.21 | 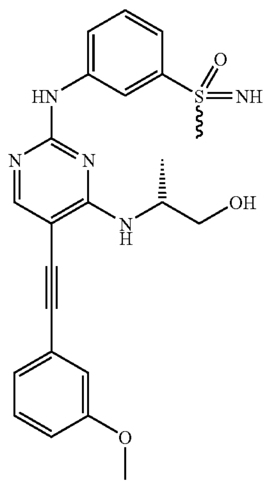 | (RS)-S-(3-[4-((R)-2-Hydroxy-1-methyl-ethylamino)-5-(3-methoxy-phenylethynyl)-pyrimidin-2-ylamino]-phenyl)-S-methylsulfoximide | $^1$H-NMR: (d6-DMSO, 400 MHz) 9.83 (s, 1H); 8.70 (s br, 1H); 8.14 (s, 1H); 7.72-7.84 (m, 1H); 7.44-7.55 (m, 2H); 7.29 (t, 1H); 7.05-7.13 (m, 2H); 6.94 (dd, 1H); 6.50 (t br, 1H); 5.00 (s br, 1H); 4.35 (mc, 1H); 3.76 (s, 3H); 3.42-3.59 (m, 2H), 3.12 (s, 3H); 1.20 (d, 3H). MS (ESI): $[M - H]^- = 450$. |
| 1.22 | 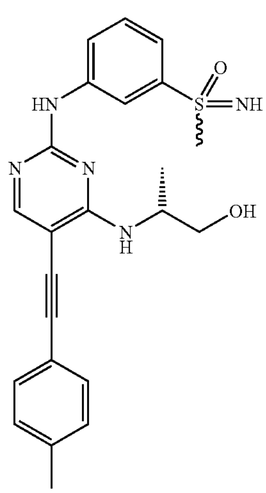 | (RS)-S-(3-[4-((R)-2-Hydroxy-1-methyl-ethylamino)-5-(4-methyl-phenylethynyl)-pyrimidin-2-ylamino]-phenyl)-S-methylsulfoximide | $^1$H-NMR: (d6-DMSO, 400 MHz) 9.74 (s, 1H); 8.68 (d br, 1H); 8.12 (s, 1H); 7.70-7.81 (m, 1H); 7.39-7.51 (m, 4H); 7.21 (d, 2H); 6.41 (t, 1H); 4.98 (s br, 1H); 4.33 (mc, 1H); 3.42-3.58 (m, 2H); 3.02 (s, 3H); 2.30 (s, 3H); 1.21 (d, 3H). MS (ESI): $[M + H]^+ = 436$. |

-continued

| Example | Structure | Name | Analytical data |
|---|---|---|---|
| 1.23 | 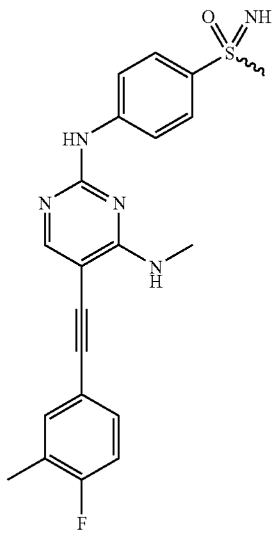 | (RS)-S-(4-[5-(4-Fluoro-3-methyl-phenyl-ethynyl)-4-methylamino-pyrimidin-2-ylamino]-phenyl)-S-methylsulfoximide | $^1$H-NMR: (d6-DMSO, 300 MHz) 9.85 (s, 1H); 8.15 (s, 1H); 8.02 (d, 2H); 7.82 (d, 2H); 7.57 (d br, 1H); 7.43-7.51 (m, 1H); 7.14-7.26 (m, 2H); 3.99 (s br, 1H); 3.02 (s, 3H); 2.99 (d, 3H); 2.26 (d, 1H). MS (ESI): [M + H]$^+$= 410. |
| 1.24 | 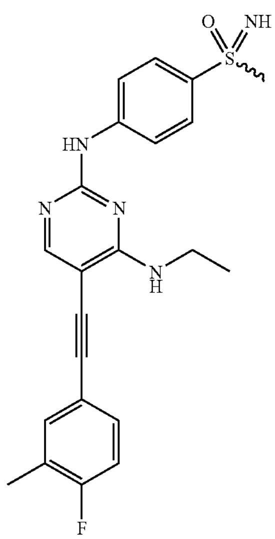 | (RS)-S-(4-[4-ethylamino-5-(4-fluoro-3-methyl-phenyl-ethynyl)-pyrimidin-2-ylamino]-phenyl)-S-methylsulfoximide | $^1$H-NMR: (d6-DMSO, 300 MHz) 9.84 (s, 1H); 8.15 (s, 1H); 8.00 (d, 2H) 7.81 (d, 2H); 7.57 (d br, 1H); 7.43-7.51 (m, 1H); 7.16-7.28 (m, 2H); 4.01 (s, 1H); 3.53 (quint, 2H); 3.02 (s, 3H); 2.26 (d, 3H); 1.24 (t, 3H). MS (ESI): [M + H]$^+$= 424. |
| 1.25 | 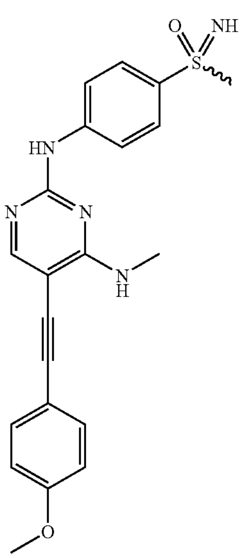 [SMILES: CNc1nc(Nc2ccc(S(C)(=N)=O)cc2)ncc1C#Cc1ccc(OC)cc1] | (RS)-S-(4-[5-(4-methoxy-phenyl-ethynyl)-4-methylamino-pyrimidin-2-ylamino]-phenyl)-S-methylsulfoximide | $^1$H-NMR: (d6-DMSO, 300 MHz) 9.82 (s, 1H); 8.13 (s br, 1H); 8.02 (d, 2H); 7.81 (d, 2H); 7.56 (d, 2H); 7.17 (q, 1H); 7.00 (d, 2H); 3.97 (s br, 1H); 3.81 (s, 3H); 3.02 (s, 3H); 2.99 (d, 3H). MS (ESI): [M + H]$^+$= 408. |

-continued

| Example | Structure | Name | Analytical data |
|---|---|---|---|
| 1.26 | 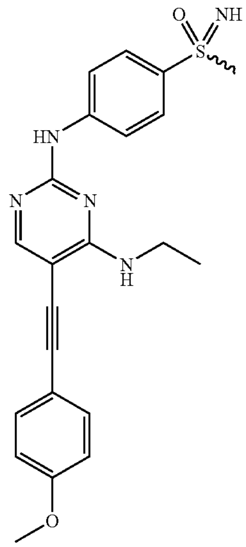 [SMILES: CCNc1nc(Nc2ccc(S(C)(=N)=O)cc2)ncc1C#Cc1ccc(OC)cc1] | (RS)-S-(4-[4-ethylamino-5-(4-methoxy-phenyl-ethynyl)-pyrimidin-2-ylamino]-phenyl)-S-methylsulfoximide | ¹H-NMR: (d6-DMSO, 300 MHz) 9.81 (s, 1H); 8.13 (s, 1H); 8.01 (d, 2H); 7.81 (d, 2H); 7.57 (d, 2H); 7.19 (t, 1H) 7.00 (d, 2H); 4.01 (s br, 1H); 3.81 (s, 3H); 3.53 (quint, 2H); 3.03 (s, 3H); 1.23 (t, 3H). MS (ESI): [M + H]⁺ = 422. |
| 1.27 | 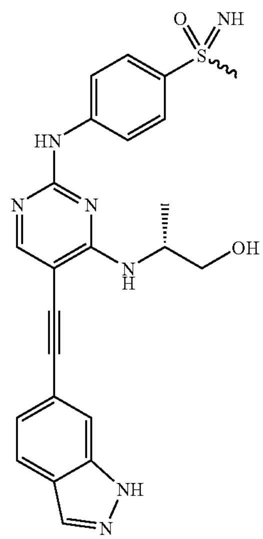 [SMILES: C[C@H](CO)Nc1nc(Nc2ccc(S(C)(=N)=O)cc2)ncc1C#Cc1ccc2cn[nH]c2c1] | (RS)-S-4-[4-((R)-2-Hydroxy-1-methyl-ethylamino)-5-(1H-indazol-6-ylethynyl)-pyrimidin-2-ylamino]-phenyl)-S-methylsulfoximide | ¹H-NMR: (d6-DMSO, 400 MHz) 13.20 (s br, 1H); 9.83 (s, 1H); 8.20 (s, 1H); 8.08 (s, 1H); 7.95 (d, 2H); 7.69-7.83 (m, 4H); 7.24 (d, 1H); 6.59 (d, 1H); 4.93 (s br, 1H); 4.38 (mc, 1H); 3.96 (s, 1H); 3.48-3.62 (m, 2H); 3.00 (s, 3H); 1.23 (d, 3H). MS (ESI): [M + H]⁺ = 462. |
| 1.28 | 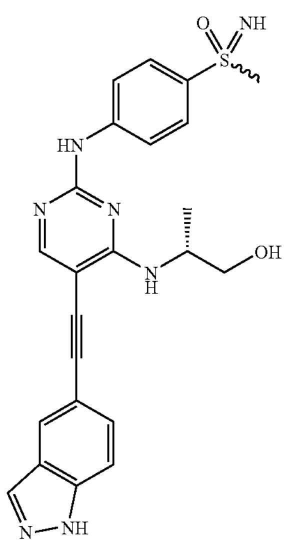 [SMILES: C[C@H](CO)Nc1nc(Nc2ccc(S(C)(=N)=O)cc2)ncc1C#Cc1ccc2[nH]ncc2c1] | (RS)-S-4-[4-((R)-2-Hydroxy-1-methyl-ethylamino)-5-(1H-indazol-5-ylethynyl)-pyrimidin-2-ylamino]-phenyl)-S-methylsulfoximide | ¹H-NMR: (d6-DMSO, 400 MHz) 13.23 (s br, 1H); 9.81 (s, 1H); 8.18 (s, 1H); 8.10 (s, 1H); 8.01 (s, 1H); 7.95 (d, 2H); 7.78 (d, 2H); 7.45 (d, 1H); 7.39 (d, 1H); 6.49 (d, 1H); 4.93 (t, 1H); 4.27 (mc, 1H); 3.96 (s, 1H); 3.47-3.61 (m, 2H); 2.99 (s, 3H); 1.23 (d, 3H). MS (LC-MS-ESI): [M + H]⁺ = 462. |

-continued

| Example | Structure | Name | Analytical data |
|---|---|---|---|
| 1.29 | 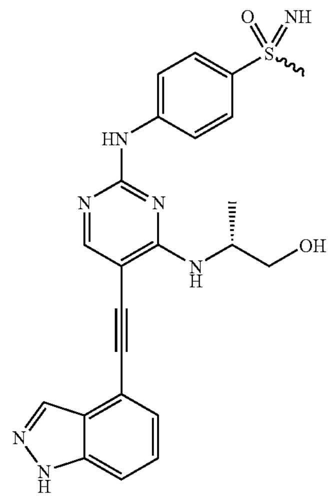 [SMILES: C[C@H](CO)Nc1nc(Nc2ccc(S(C)(=N)=O)cc2)ncc1C#Cc1cccc2[nH]ncc12] | (RS)-S-4-[4-((R)-2-Hydroxy-1-methyl-ethylamino)-5-(1H-indazol-4-ylethynyl)-pyrimidin-2-ylamino]-phenyl)-S-methylsulfoximide | $^1$H-NMR: (d6-DMSO, 300 MHz) 13.32 (s br, 1H); 9.94 (s, 1H); 8.35 (s, 1H); 8.27 (s, 1H); 8.00 (d, 2H); 7.82 (d, 2H); 7.60 (d, 1H); 7.32-7.46 (m, 2H); 5.08 (t, 1H); 4.34 (mc, 1H); 4.01 (s, 1H); 3.62 (mc, 2H); 3.04 (s, 3H); 1.28 (d, 3H). MS (LC-MS-ESI): [M + H]$^+$ = 462. |
| 1.30 | 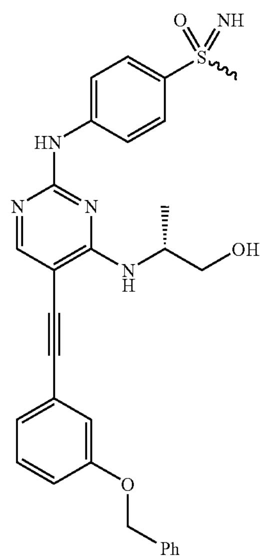 [SMILES: C[C@H](CO)Nc1nc(Nc2ccc(S(C)(=N)=O)cc2)ncc1C#Cc1cccc(OCc2ccccc2)c1] | (RS)-S-4-[5-(3-Benzyloxy-phenylethynyl)-4-((R)-2-hydroxy-1-methyl-ethylamino)-pyrimidin-2-ylamino]-S-methylsulfoximide | $^1$H-NMR: (d6-DMSO, 400 MHz) 9.83 (s br, 1H); 8.15 (s, 1H); 7.93 (d, 2H); 7.77 (d, 2H); 7.27-7.46 (m, 6H); 7.20 (d, 1H); 7.13 (d, 1H); 7.03 (dd, 1H); 6.48 (d, 1H); 5.12 (s, 2H); 4.93 (t, 1H); 4.27 (mc, 1H); 3.95 (s, 1H); 3.53 (mc, 2H); 2.98 (s, 3H); 1.22 (d, 3H). MS (LC-MS-ESI): [M + H]$^+$ = 529. |
| 1.31 | 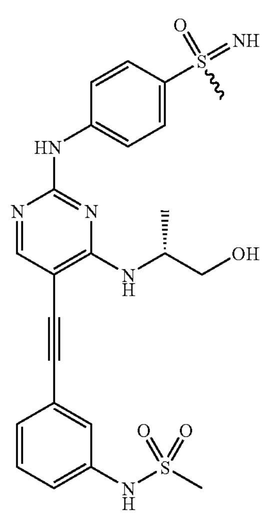 [SMILES: C[C@H](CO)Nc1nc(Nc2ccc(S(C)(=N)=O)cc2)ncc1C#Cc1cccc(NS(C)(=O)=O)c1] | (RS)-N-{3-[(4-{[(R)-2-hydroxy-1-methyl-ethylamino}-2-{[4-(S-methylsulfonimidoyl)phenyl]amino}pyrimidin-5-yl)ethynyl]phenyl}methanesulfonamide | $^1$H-NMR: (d6-DMSO, 400 MHz) 9.88 (s br, 1H); 9.84 (s, 1H); 8.18 (s, 1H); 7.94 (d, 2H); 7.78 (d, 2H); 7.27-7.40 (m, 3H); 7.19 (dd, 1H); 6.52 (d, 1H); 4.91 (t, 1H); 4.28 (mc, 1H); 3.97 (s, 1H); 3.45-3.60 (m, 2H); 2.97-3.03 (m, 6H); 1.22 (d, 3H). MS (ESI): [M + H]$^+$ = 515. |

| Example | Name | Analytical data |
|---|---|---|
| 1.32 | (RS)-S-4-[4-ethylamino-5-(1H-indazol-4-ylethynyl)-pyrimidin-2-ylamino]-phenyl)-S-methylsulfoximide | $^1$H-NMR: (d6-DMSO, 300 MHz) 13.23 (s br, 1H); 9.88 (s, 1H); 8.28 (s, 1H); 8.25 (s, 1H); 7.99 (d, 2H); 7.78 (d, 2H); 7.51-7.57 (m, 1H); 7.30-7.42 (m, 2H); 7.23 (t, 1H); 3.98 (s, 1H); 3.53 (quint, 2H); 3.00 (s, 3H); 1.24 (t, 3H). MS (ESI): [M + H]$^+$ = 432. |
| 1.33 | (RS)-S-4-[5-(1H-indazol-4-ylethynyl)-4-methylamino-pyrimidin-2-ylamino]-phenyl)-S-methylsulfoximide | $^1$H-NMR: (d6-DMSO, 400 MHz) 13.25 (s br, 1H); 9.90 (s, 1H); 8.25-8.33 (m, 2H); 8.00 (d, 2H); 7.78 (d, 2H); 7.52 (d, 1H); 7.31-7.43 (m, 2H); 7.22 (q br, 1H); 3.90 (s br, 1H); 2.95-3.07 (m, 6H). MS (ESI): [M − H]$^-$ = 416. |

Example Compound 2.1

Preparation of (RS)—N-(Ethoxycarbonyl)-S-4-[4-((R)-2-Hydroxy-1-methyl-ethylamino)-5-(pyridin-3-ylethynyl)-pyrimidin-2-ylamino]-phenyl)-S-methyl-sulfoximide

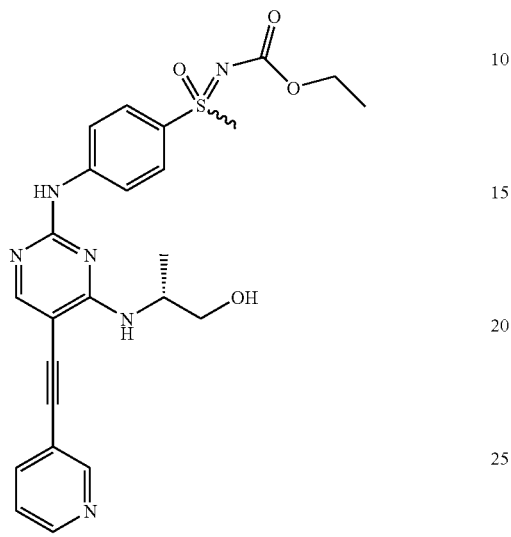

In analogy to GP 8b, PdCl$_2$(PPh$_3$)$_2$ (5 mg) was added to a mixture of intermediate 35 (88 mg), copper iodide (10 mg), 3-ethynylpyridine (30 mg) in THF (750 µl) and triethylamine (250 µl). The mixture was heated to reflux in a capped flask for 18 h. After cooling to room temperature, water and ethyl acetate was added and the organic layer was separated, filtered and concentrated in vacuo and purified by HPLC.

t$_R$ (HPLC method A): 5.86 min.
MS (ESI): [M+H]$^+$=495.

The synthesis of example compounds 2.2-2.9 was accomplished in an analogous manner by applying GP 8b to intermediate 35 and the respective alkynes.

| Example | Structure | Name | Analytical data |
|---|---|---|---|
| 2.2 | 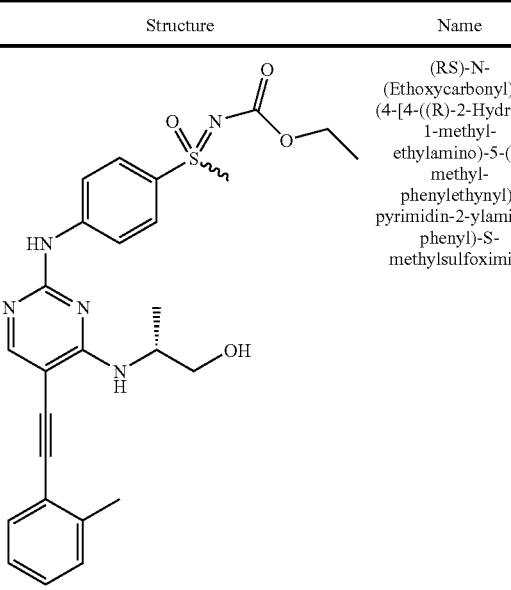 | (RS)-N-(Ethoxycarbonyl)-S-(4-[4-((R)-2-Hydroxy-1-methyl-ethylamino)-5-(2-methyl-phenylethynyl)-pyrimidin-2-ylamino]-phenyl)-S-methylsulfoximide | t$_R$ (HPLC method A): 7.32 min. MS (ESI): [M + H]$^+$ = 508. |

-continued

| Example | Structure | Name | Analytical data |
|---|---|---|---|
| 2.3 | 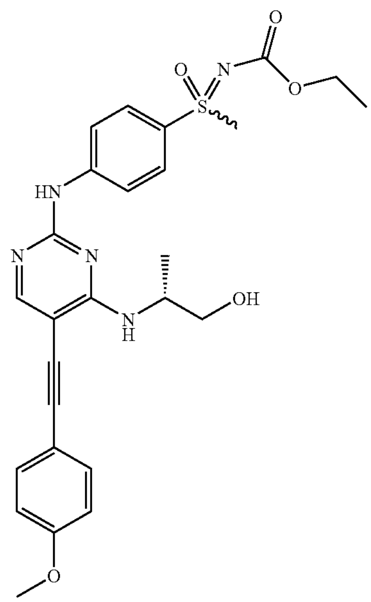 [SMILES: CCOC(=O)N=S(C)(=O)c1ccc(Nc2ncc(C#Cc3ccc(OC)cc3)c(N[C@H](C)CO)n2)cc1] | (RS)-N-(Ethoxycarbonyl)-S-(4-[4-((R)-2-Hydroxy-1-methyl-ethylamino)-5-(4-methoxy-phenylethynyl)-pyrimidin-2-ylamino]-phenyl)-S-methylsulfoximide | $t_R$ (HPLC method A): 6.90 min. MS (ESI): $[M + H]^+ = 524$. |
| 2.4 | 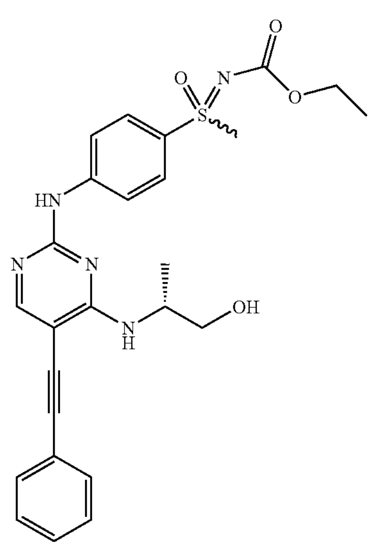 | (RS)-N-(Ethoxycarbonyl)-S-(4-[4-((R)-2-Hydroxy-1-methyl-ethylamino)-5-(phenylethynyl)-pyrimidin-2-ylamino]-phenyl)-S-methylsulfoximide | $t_R$ (HPLC method A): 6.91 min. MS (ESI): $[M + H]^+ = 494$. |

| Example | Structure | Name | Analytical data |
|---|---|---|---|
| 2.5 | 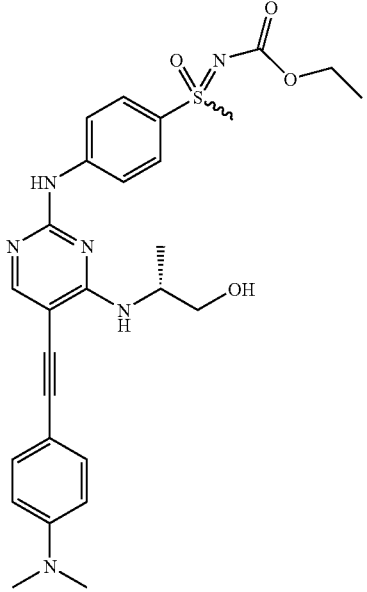 [SMILES: CCOC(=O)N=S(C)(=O)c1ccc(Nc2ncc(C#Cc3ccc(N(C)C)cc3)c(N[C@H](C)CO)n2)cc1] | (RS)-N-(Ethoxycarbonyl)-S-(4-[5-(4-dimethyl-aminophenyl-ethynyl)-4-((R)-2-hydroxy-1-methyl-ethylamino)-pyrimidin-2-ylamino]-phenyl)-S-methylsulfoximide | $t_R$ (HPLC method A): 6.64 min. MS (ESI): $[M + H]^+ = 537$. |
| 2.6 | 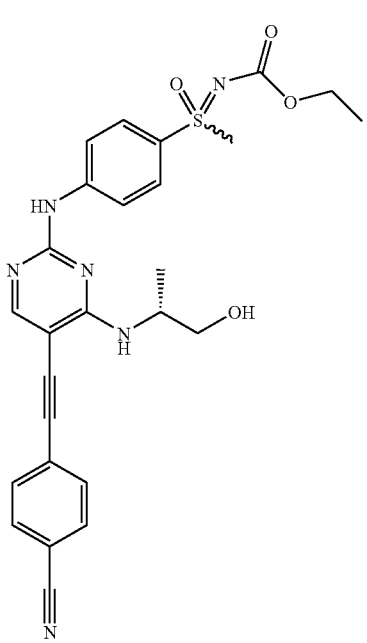 [SMILES: CCOC(=O)N=S(C)(=O)c1ccc(Nc2ncc(C#Cc3ccc(C#N)cc3)c(N[C@H](C)CO)n2)cc1] | (RS)-N-(Ethoxycarbonyl)-S-(4-[5-(4-cyanophenyl-ethynyl)-4-((R)-2-hydroxy-1-methyl-ethylamino)-pyrimidin-2-ylamino]-phenyl)-S-methylsulfoximide | $t_R$ (HPLC method A): 6.92 min. MS (ESI): $[M + H]^+ = 519$. |

-continued

| Example | Structure | Name | Analytical data |
|---|---|---|---|
| 2.7 | 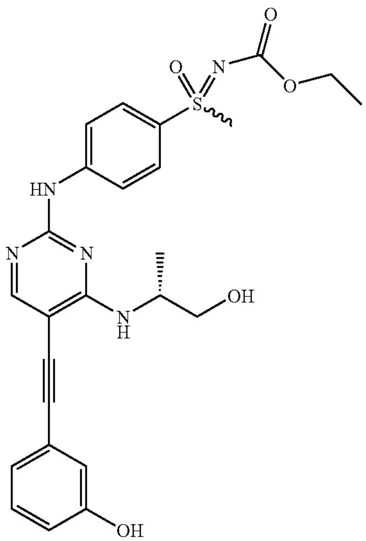 [SMILES: CCOC(=O)N=S(C)(=O)c1ccc(Nc2ncc(C#Cc3cccc(O)c3)c(N[C@H](C)CO)n2)cc1] | (RS)-N-(Ethoxycarbonyl)-S-4-[4-((R)-2-Hydroxy-1-methyl-ethylamino)-5-(3-hydroxyphenyl-ethynyl)-pyrimidin-2-ylamino]-phenyl)-S-methyl-sulfoximide | $t_R$ (HPLC method B): 2.84 min. MS (ESI): $[M + H]^+$ = 510. |
| 2.8 | 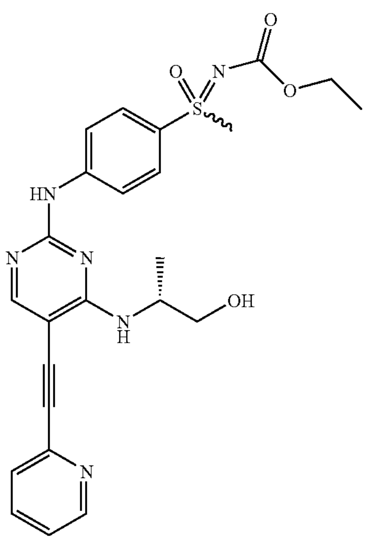 [SMILES: CCOC(=O)N=S(C)(=O)c1ccc(Nc2ncc(C#Cc3ccccn3)c(N[C@H](C)CO)n2)cc1] | (RS)-N-(Ethoxycarbonyl)-S-4-[4-((R)-2-Hydroxy-1-methyl-ethylamino)-5-(pyridin-2-ylethynyl)-pyrimidin-2-ylamino]-phenyl)-S-methyl-sulfoximide | $t_R$ (HPLC method A): 5.76 min. MS (ESI): $[M + H]^+$ = 495. |
| 2.9 | 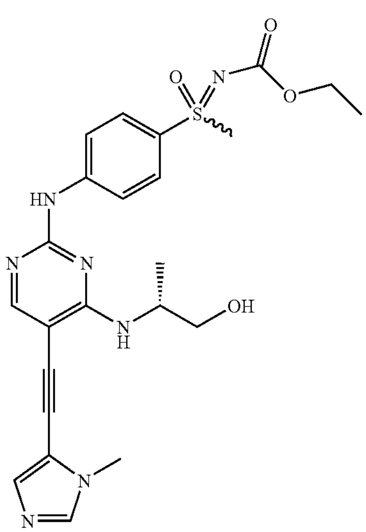 [SMILES: CCOC(=O)N=S(C)(=O)c1ccc(Nc2ncc(C#Cc3cncn3C)c(N[C@H](C)CO)n2)cc1] | (RS)-N-(Ethoxycarbonyl)-S-4-[4-((R)-2-Hydroxy-1-methyl-ethylamino)-5-(3-methyl-3H-imidazol-4-yl-ethynyl)-pyrimidin-2-ylamino]-phenyl)-S-methyl-sulfoximide | $t_R$ (HPLC method A): 4.94 min. MS (ESI): $[M + H]^+$ = 498. |

Example Compound 3.1

Preparation of (RS)—S-(3-[5-(4-Ethoxy-phenyl-ethynyl)-4-((R)-2-hydroxy-1-methyl-ethylamino)-pyrimidin-2-ylamino]-phenyl)-N-(isopropylcarbamoyl)-S-methylsulfoximide

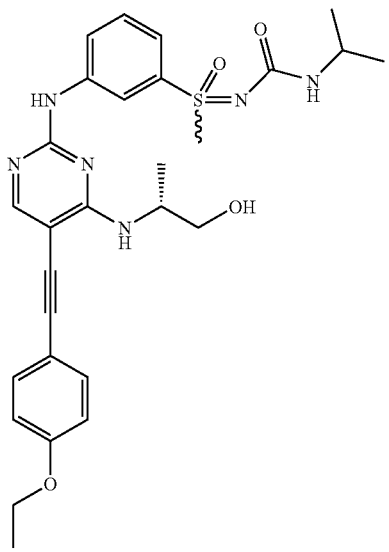 [SMILES: CCOc1ccc(C#Cc2cnc(Nc3cccc(S(C)(=O)=NC(=O)NC(C)C)c3)nc2N[C@H](C)CO)cc1]

PdCl$_2$(PPh$_3$)$_2$ (4.1 mg, 0.006 mmol, 3 mol %), 152 mg Intermediate 35.1 (0.29 mmol, 1.5 eq.), 41.5 mg (4-ethoxy-phenylethynyl)-trimethylsilane (0.19 mmol, 1 eq.) and 0.76 mL TBAF solution (1.0 M in THF, 0.76 mmol, 4 eq.) in 3 mL THF were heated to 80° C. for 40 min by microwave irradiation. The mixture was concentrated in vacuo. Flash column chromatography and subsequent HPLC purification provided 44 mg (0.08 mmol, 42% yield) of the target compound.

$^1$H-NMR (DMSO, 300 MHz): 9.88 (s, 1 H); 8.62 (s, 1 H); 8.14 (s, 1 H); 7.85 (d, 1H); 7.53 (t, 1 H); 7.50 (d, 2 H); 7.46 (d, 1 H); 6.98 (d, 2 H); 6.81 (d, 1 H); 6.56 (d, 1H); 4.35 (m, 1 H); 4.07 (q, 2 H); 3.61 (m, 1 H); 3.55 (m, 2 H); 3.34 (d, 3 H); 1.34 (t, 3 H); 1.23 (d, 3 H); 1.00 (m, 6 H).

MS (ESI): [M+H]$^+$=551.

Example Compound 3.2

Preparation of (RS)—S-(4-[5-(4-Ethoxy-phenyl-ethynyl)-4-((R)-2-hydroxy-1-methyl-ethylamino)-pyrimidin-2-ylamino]-phenyl)-S-methylsulfoximide

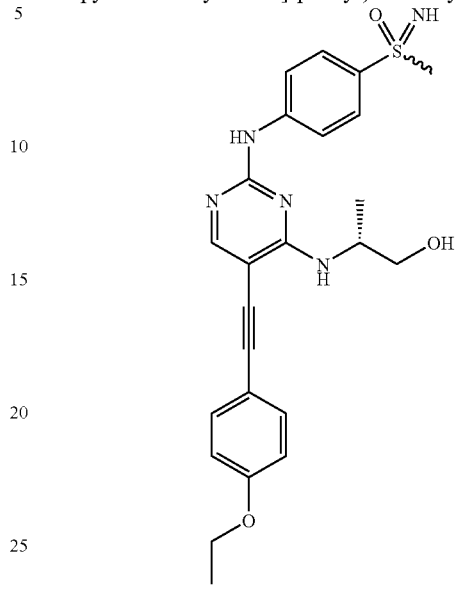

PdCl$_2$(PPh$_3$)$_2$ (4.2 mg, 0.006 mmol, 3 mol %), 134 mg Intermediate 37 (0.3 mmol, 1.5 eq.), 43.7 mg (4-ethoxy-phenylethynyl)-trimethylsilane (0.2 mmol, 1 eq.) and 0.8 mL TBAF solution (1.0 M in THF, 0.8 mmol, 4 eq.) in 3.5 mL THF were heated to 80° C. for 40 min by microwave irradiation. The mixture was concentrated in vacuo. Flash column chromatography and subsequent HPLC purification provided the target compound.

$^1$H-NMR (DMSO, 300 MHz): 9.79 (s, 1 H); 8.11 (s, 1 H); 7.93 (d, 2 H); 7.76 (d, 2 H); 7.45 (d, 2 H); 6.93 (d, 2 H); 6.43 (d, 1 H); 4.92 (d, 1 H); 4.24 (mc, 1 H); 4.02 (q, 2 H); 3.96 (s, 1 H); 3.52 (mc, 2 H); 2.98 (s, 3 H); 1.30 (t, 3 H); 1.20 (d, 3 H).

MS (ESI): [M+H]$^+$=466.

The synthesis of example compounds 3.3-3.6 was accomplished in a similar manner by applying GP8c to intermediate 37 and the respective trimethylsilyl alkynes 53, 54, 56, and 57, respectively.

| Example | Structure | Name | Analytical data |
|---|---|---|---|
| 3.3 | (structure shown) | 3-[(4-[(R)-2-hydroxy-1-methyl-ethylamino]-2-{[(RS)-4-(S-methyl sulfonimidoyl)phenyl]amino}pyrimidin-5-yl)ethynyl]-N-methylbenzamide | $^1$H-NMR: (d6-DMSO, 400 MHz) 9.84 (s, 1H); 8.52 (q br, 1H); 8.18 (s, 1H); 7.90-8.01 (m, 3H); 7.74-7.82 (m, 3H); 7.69 (d, 1H); 7.49 (t, 1H); 6.57 (d, 1H); 4.92 (t, 1H); 4.28 (mc, 1H); 3.97 (s, 1H); 3.44-3.60 (m, 2H); 2.99 (s, 3H); 2.76 (d, 3H); 1.22 (d, 3H). MS (ESI): [M + H]$^+$ = 479. |

| Example | Structure | Name | Analytical data |
|---|---|---|---|
| 3.4 | 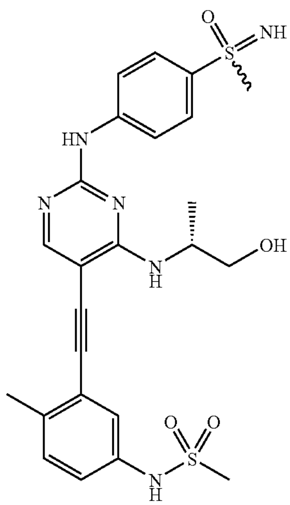 [SMILES: Cc1ccc(NS(C)(=O)=O)cc1C#Cc1cnc(Nc2ccc(S(C)(=N)=O)cc2)nc1N[C@H](C)CO] | N-{3-[(4-[(R)-2-hydroxy-1-methyl-ethyamino]-2-{[4-(S-methylsulfonimidoyl)phenyl]amino}pyrimidin-5-yl)ethynyl]-4-methylphenyl}methanesulfonamide | ¹H-NMR: (d6-DMSO, 300 MHz) 9.91 (s, 1H); 9.73 (s, 1H); 8.24 (s, 1H); 7.99 (d, 2H); 7.82 (d, 2H); 7.37 (d, 1H); 7.31 (d, 1H); 7.18 (dd, 1H); 6.39 (d, 1H); 4.96 (t, 1H); 4.33 (mc, 1H); 4.05 (s br, 1H); 3.52-3.62 (m, 2H); 3.04 (s, 3H); 2.98 (s, 3H); 2.38 (s, 3H); 1.25 (d, 3H). MS (ESI): [M + H]⁺ = 529. |
| 3.5 | 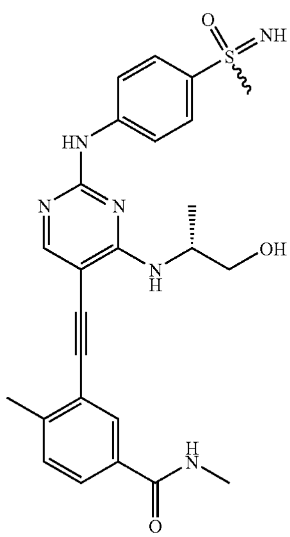 [SMILES: CNC(=O)c1ccc(C)c(C#Cc2cnc(Nc3ccc(S(C)(=N)=O)cc3)nc2N[C@H](C)CO)c1] | 3-[(4-[(R)-2-hydroxy-1-methyl-ethylamino]-2-{[4-(S-methylsulfonimidoyl)phenyl]amino}pyrimidin-5-yl)ethynyl]-N,4-dimethylbenzamide | ¹H-NMR: (d6-DMSO, 300 MHz) 9.90 (s, 1H); 8.48 (q br, 1H); 8.24 (s, 1H); 7.96-8.03 (, 3H); 7.83 (d, 2H); 7.76 (dd, 1H); 7.42 (d, 1H); 6.47 (d, 1H); 4.96 (t, 1H); 4.32 (mc, 1H); 4.00 (s, 1H); 3.53-3.64 (m, 2H); 3.02 (s, 3H); 2.80 (d, 3H); 1.25 (d, 3H). MS (ESI): [M + H]⁺ = 493. |
| 3.6 | 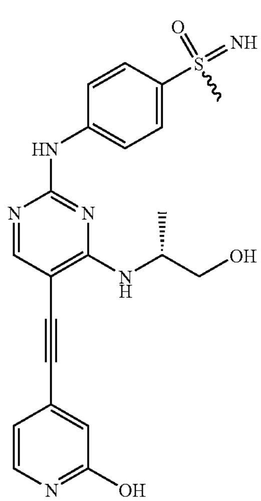 [SMILES: C[C@H](CO)Nc1nc(Nc2ccc(S(C)(=N)=O)cc2)ncc1C#Cc1ccnc(O)c1] | (RS)-S-(4-[4-((R)-2-Hydroxy-1-methyl-ethylamino)-5-(3-hydroxy-pyrid-4-yl-ethynyl)-pyrimidin-2-ylamino]-phenyl)-S-methylsulfoximide | ¹H-NMR: (d6-DMSO, 300 MHz) 11.64 (s br, 1H); 9.97 (s, 1H); 8.24 (s, 1H); 7.99 (d, 1H); 7.83 (d, 2H); 7.42 d, 1H); 6.64 (d, 1H); 6.57 (s, 1H); 6.29 (d br, 1H); 4.97 (t, 1H); 4.32 (mc, 1H); 4.02 (s, 1H); 3.48-3.68 (m, 2H); 3.02 (s, 3H); 1.26 (d, 3H). MS (ESI): [M + H]⁺ = 439. |

Example Compound 4.1

Preparation of (RS)—S-(3-[5-(4-methoxy-phenyl-ethynyl)-pyrimidin-2-ylamino]-phenyl)-S-methylsulfoximide

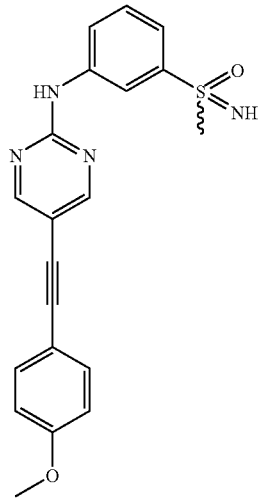 [SMILES: COc1ccc(C#Cc2cnc(Nc3cccc(S(C)(=N)=O)c3)nc2)cc1]

Example compound 4.1 was prepared in analogy to GP8c from Intermediate 49.2 and 4-methoxyphenylacetylene in 36% yield.

$^1$H-NMR (DMSO, 300 MHz): 10.30 (s, 1 H); 8.72 (s, 2 H); 8.36 (s br, 1 H); 8.00-8.11 (m, 1 H); 7.45-7.61 (m, 4 H); 7.01 (d, 2 H); 4.17 (s br, 1 H); 3.81 (s, 3 H); 3.06 (s, 3 H).

MS (ESI): [M+H]$^+$=379.

Example Compound 4.2

Preparation of (RS)—S-(3-[5-(3-hydroxy-phenyl-ethynyl)-pyrimidin-2-ylamino]-phenyl)-S-methylsulfoximide

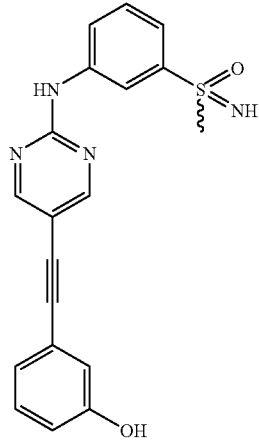 [SMILES: CS(=N)(=O)c1cccc(Nc2ncc(C#Cc3cccc(O)c3)cn2)c1]

Example compound 4.2 was prepared in analogy to GP8c from Intermediate 49.2 and 3-hydroxyphenylacetylene in 32% yield.

$^1$H-NMR (DMSO, 400 MHz): 10.32 (s, 1 H); 9.70 (s, 1 H); 8.68 (s, 2 H); 8.32 (s, 1 H); 7.97-8.05 (m, 1 H); 7.48-7.55 (m, 2 H); 7.21 (t, 1 H); 6.93 (d, 1 H); 6.88 (s br, 1 H); 6.79 (d br, 1 H); 3.07 (s, 3 H).

MS (ESI): [M+H]$^+$=365.

The following example compounds are accessible in analogy to the general descriptions of this invention and/or the exemplified procedures given above or from example compounds or intermediates by standard transformations known to the person skilled in the art.

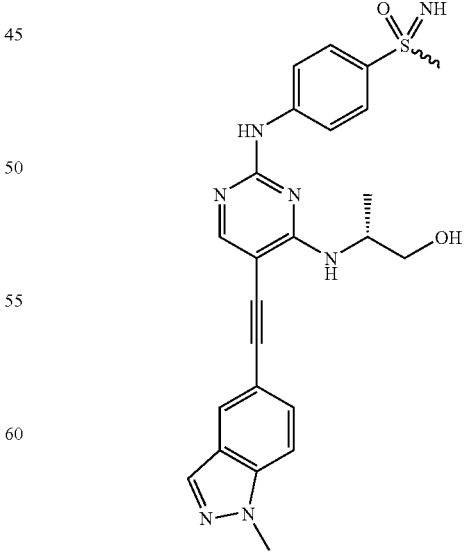

Example 5.1

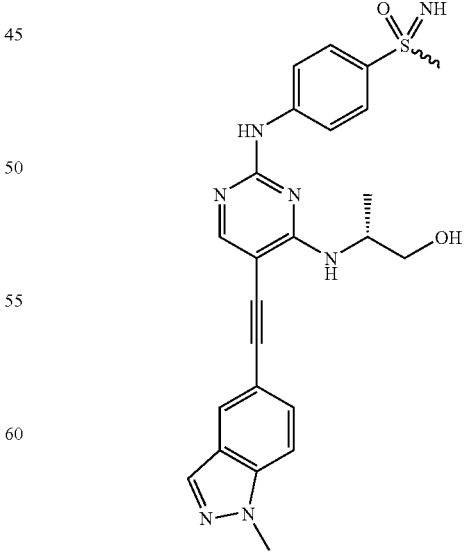

Example 5.2

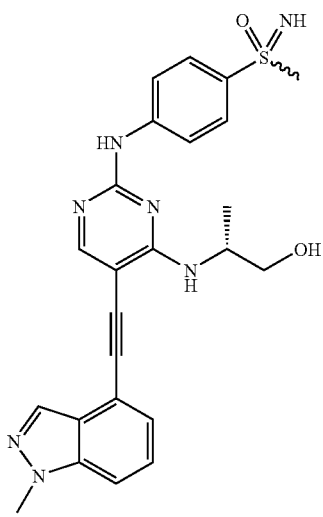 [SMILES: C[C@H](CO)Nc1nc(Nc2ccc(S(C)(=N)=O)cc2)ncc1C#Cc1cccc2c1cnn2C]

Example 5.3

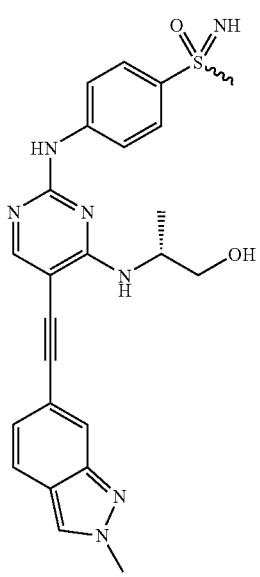 [SMILES: C[C@H](CO)Nc1nc(Nc2ccc(S(C)(=N)=O)cc2)ncc1C#Cc1ccc2cn(C)nc2c1]

Example 5.4

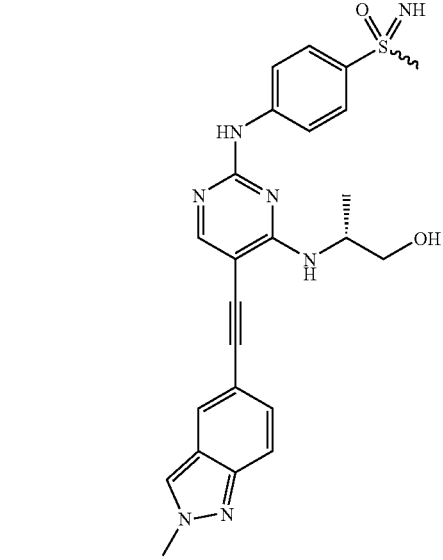

Example 5.5

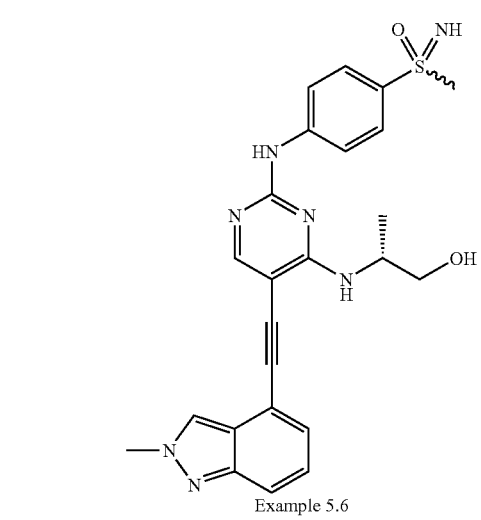

Example 5.6

DESCRIPTION OF BIOLOGICAL ASSAYS

A selection of assays to profile compounds of the present invention is described in the following paragraphs.

Assay 1: Tie2 ELISA Assay

Cellular activity of compounds of the present invention as inhibitors of Tie2 kinase activity was measured employing a Tie2 ELISA assay as described in the following paragraphs. Herein CHO cell-cultures, which are stably transfected by known techniques with Tie2 using DHFR deficiency as selection marker, are stimulated by angiopoietin-2. The specific autophosphorylation of Tie2 receptors is quantified with a sandwich-ELISA using anti-Tie2 antibodies for catch and anti-phosphotyrosine antibodies coupled to HRP for detection.

Materials:
  96well tissue culture plate, sterile, Greiner
  96well FluoroNunc plate MaxiSorp Surface C, Nunc
  96well plate polypropylene for compound dilution in DMSO
  CHO Tie2/DHFR (transfected cells)

PBS−; PBS++, DMSO
MEM alpha Medium with Glutamax-I without Ribo-
  nucleosides and
  Deoxyribonucleosides (Gibco #32561-029)
  with 10% FCS after dialysis! and 1% PenStrep
Lysis buffer: 1 Tablet "Complete" protease inhibitor
  1 cap Vanadate (1 mL>40 mg/mL; working solution 2
    mM)
  ad 50 mL with Duschl-Puffer
  pH 7.6
Anti-Tie2-antibody 1: 425 in Coating Buffer pH 9.6
  Stock solution: 1.275 mg/mL>working.: 3 µg/mL
PBST: 2 bottles PBS(10×)+10 ml Tween, fill up with VE-
  water
RotiBlock 1: 10 in VE-water
Anti-Phosphotyrosine HRP-Conjugated 1: 10000 in 3%
  TopBlock
  3% TopBlock in PBST
BM Chemiluminescence ELISA Substrate (POD)
  solution B 1: 100 solution A
SF9 cell culture medium
Ang2-Fc in SF9 cell culture medium
Cell Experiment:
  Dispense $5 \times 10^4$ cells/well/98 µL in 96well tissue culture
    plate
  Incubate at 37° C./5% $CO_2$
  After 24 h add compounds according to desired concentra-
    tions
  Add also to control and stimulated values without com-
    pounds 2 µL DMSO
  And mix for a few min at room temperature
  Add 100 µL Ang2-Fc to all wells except control, which
    receives insect medium
  Incubate 20 min at 37° C.
  Wash 3× with PBS++
  Add 100 µl Lysis buffer/well and shake a couple of min at
    room temperature
  Store lysates at 20° C. before utilizing for the ELISA
Performance of Sandwich-ELISA
  Coat 96well FluoroNunc Plate MaxiSorp Surface C with
    anti-Tie2 mAb 1: 425 in Coating buffer pH 9.6; 100
    µL/well overnight at 4° C.
  Wash 2× with PBST
  Block plates with 250 µL/well RotiBlock 1: 10 in VE-water
  Incubate for 2 h at room temperature or overnight at 4° C.
    shaking
  Wash 2× in PBST
  Add thawed lysates to wells and incubate overnight shak-
    ing at 4° C.
  Wash 2× with PBST
  Add 100 µL/well anti-Phosphotyrosine HRP-Conjugated
    1:10000 in 3% TopBlock (3% TopBlock in PBST) and
    incubate overnight under shaking
  Wash 6× with PBST
  Add 100 µL/well BM Chemiluminescence ELISA Sub-
    strate (POD)
    solutions 1 und 2 (1:100)
  Determine luminescence with the LumiCount.
Assay 2: Tie-2-Kinase HTRF-Assay without kinase preacti-
vation
  Tie2-inhibitory activity of compounds of the present inven-
tion was quantified employing two Tie2 HTRF assay as
described in the following paragraphs.
  A recombinant fusion protein of GST and the intracellular
domains of Tie-2, expressed in insect cells (Hi-5) and purified
by Glutathion-Sepharose affinity chromatography was used
as kinase. Alternatively, commercially available GST-Tie2-
fusion protein (Upstate Biotechnology, Dundee, Scotland)
can be used As substrate for the kinase reaction the biotiny-
lated peptide biotin-Ahx-EPKDDAYPLYSDFG (C-terminus
in amid form) was used which can be purchased e.g. from the
company Biosynthan GmbH (Berlin-Buch, Germany).
Detection of phosphorylated product is achieved specifically
by a trimeric detection complex consisting of the phosphory-
lated substrate, streptavidin-XLent (SA-XLent) which binds
to biotin, and Europium Cryptate-labeled anti-phosphoty-
rosine antibody PT66 which binds to phosphorylated
tyrosine.
  Tie-2 (3.5 ng/measurement point) was incubated for 60
min at 22° C. in the presence of 10 µM adenosine-tri-phos-
phate (ATP) and 1 µM substrate peptide (biotin-Ahx-EPKD-
DAYPLYSDFG-$NH_2$) with different concentrations of test
compounds (0 µM and concentrations in the range 0.001-20
µM) in 5 µl assay buffer [50 mM Hepes/NaOH pH 7, 10 mM
$MgCl_2$, 0.5 mM $MnCl_2$, 1.0 mM dithiothreitol, 0.01% NP40,
protease inhibitor mixture ("Complete w/o EDTA" from
Roche, 1 tablet per 2.5 ml), 1% (v/v) dimethylsulfoxide]. The
reaction was stopped by the addition of 5 µl of an aqueous
buffer (25 mM Hepes/NaOH pH 7.5, 0.28% (w/v) bovine
serum albumin) containing EDTA (90 mM) and the HTRF
(Homogeneous Time Resolved Fluorescence) detection
reagents streptavidine-XLent (0.2 µM, from Cis Biointerna-
tional, Marcoule, France) and PT66-Eu-Chelate (0.3 ng/µl; a
europium-chelate labelled anti-phospho-tyrosine antibody
from Perkin Elmer).
  The resulting mixture was incubated 1 h at 22° C. to allow
the binding of the biotinylated phosphorylated peptide to the
streptavidine-XLent and the PT66-Eu-Chelate. Subsequently
the amount of phosphorylated substrate peptide was evalu-
ated by measurement of the resonance energy transfer from
the PT66-Eu-Chelate to the streptavidine-XLent. Therefore,
the fluorescence emissions at 620 nm and 665 nm after exci-
tation at 350 nm was measured in a HTRF reader, e.g. a
Rubystar (BMG Labtechnologies, Offenburg, Germany) or a
Viewlux (Perkin-Elmer). The ratio of the emissions at 665 nm
and at 622 nm was taken as the measure for the amount of
phosphorylated substrate peptide. The data were normalised
(enzyme reaction without inhibitor=0% inhibition, all other
assay components but no enzyme=100% inhibition) and IC50
values were calculated by a 4 parameter fit using an inhouse
software.
Assay 3: Tie-2-Kinase HTRF-Assay with Kinase Preactiva-
tion
  A recombinant fusion protein of GST and the intracellular
domains of Tie-2, expressed in insect cells (Hi-5) and purified
by Glutathion-Sepharose affinity chromatography was used
as kinase. As substrate for the kinase reaction the biotinylated
peptide biotin-Ahx-EPKDDAYPLYSDFG (C-terminus in
amid form) was used which can be purchased e.g. from the
company Biosynthan GmbH (Berlin-Buch, Germany).
  For activation, Tie-2 was incubated at a conc. 12.5 ng/µl of
for 20 min at 22° C. in the presence of 250 µM adenosine-tri-
phosphate (ATP) in assay buffer [50 mM Hepes/NaOH pH 7,
10 mM $MgCl_2$, 0.5 mM $MnCl_2$, 1.0 mM dithiothreitol, 0.01%
NP40, protease inhibitor mixture ("Complete w/o EDTA"
from Roche, 1 tablet per 2.5 ml)].
  For the subsequent kinase reaction, the preactivated Tie-2
(0.5 ng/measurement point) was incubated for 20 min at 22°
C. in the presence of 10 µM adenosine-tri-phosphate (ATP)
and 1 µM substrate peptide (biotin-Ahx-EPKDDAYPLYS-
DFG-$NH_2$) with different concentrations of test compounds
(0 µM and concentrations in the range 0.001-20 µM) in 5 µl
assay buffer [50 mM Hepes/NaOH pH 7, 10 mM $MgCl_2$, 0.5
mM $MnCl_2$, 0.1 mM sodium ortho-vanadate, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and IC50 values were calculated by a 4 parameter fit using an inhouse software.

Assay 4: VEGFR2 Kinase (KDR) HTRF Assay

KDR inhibitory activity of compounds of the present invention was quantified employing the KDR HTRF assay as described in the following paragraphs.

GST-tagged recombinant kinase domain of the human KDR expressed in SF-9 cells was used as kinase. As substrate for the kinase reaction the biotinylated peptide biotin-Ahx-DFGLARDMYDKEYYSVG (C-terminus in acid form) was used which can be purchased e.g. form the company Biosynthan GmbH (Berlin-Buch, Germany). KDR was incubated for 45 min at 22° C. in the presence of different concentrations of test compounds in 5 µl assay buffer [50 mM Hepes/NaOH pH 7.0, 25 mM $MgCl_2$, 5 mM $MnCl_2$, 1.0 mM dithiothreitol, 0.1 mM sodium ortho-vanadate, 10 µM adenosine-tri-phosphate (ATP), 0.5 µM substrate, 0.001% (v/v) Nonidet-P40 (Sigma), 1% (v/v) dimethylsulfoxide]. The concentration of KDR was adjusted depending of the activity of the enzyme lot and was chosen appropriate to have the assay in the linear range. The reaction was stopped by the addition of 5 µL of a solution of HTRF detection reagents (0.1 µM streptavidine-XLent and 2 nM PT66-Eu-Chelate, an europium-chelate Labelled anti-phospho-tyrosine antibody from Perkin Elmer) in an aqueous EDTA-solution (125 mM EDTA, 0.2% (w/v) bovine serum albumin in 50 mM HEPES/NaOH pH 7.0).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a ViewLux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Assay 5: VEGF-Stimulated Endothelial Cell Proliferation Assay

MVECs are plated to collagen coated 48 well plates at a density of 30 000 cells per well in Earles's Medium M199 (complete with serum). After 4 h the medium is exchanged for medium containing 2% human serum without growth factors (200 µl) and cells are maintained overnight at low serum conditions. The other day the medium is exchanged for the same low serum medium containing in addition test compounds or vehicle in the appropriate concentrations using appropriate controls is exchanged. Five minutes later low serum medium containing 40 ng/ml VEGF is added (200 µl). Cells are cultured for 3 days before mixing with Alamar Blue® (dilution factor of 1: 20) and incubating it for 2 h at 37° C. Measurement of fluorescence intensity is done with the following filters: 528/25 Excitation, 590/35 Emission for the determination of the IC50 concentrations.

Culture Medium Composition

Earle's Medium 199 with stable Glutamine (PAA)+5 ml PenStrep (100×; 10000 Units/10 mg/ml) (PAA)+5 ml Non Essential Amino Acids (100×; without L-Glutamine) (PAA)+5 ml Sodium Pyruvat (100 mM) (PAA)+50 ml FCS (PAA)+50 ml HS+1 ml ECGS in Dulbecco's PBS without $Ca^{2+}+Mg^{2+}$+(5 mg/ml) (Sigma)+1 ml Heparin (2500 Units/ml)+2.5 ml Biotect-Protection medium (Biochrom AG)=complete Earle's M 199 medium Earle's Medium 199 (PAA) with stable Glutamine+5 ml PenStrep (100×; 10000 Units/10 mg/ml) (PAA)+5 ml Non Essential Amino Acids (100×; without L-Glutamine) (PAA)+5 ml Sodium Pyruvat (100 mM) (PAA), 2% HS+2.5 ml Biotect- Protection medium (Biochrom AG)

Assay 6: CDK2/Cyclin E Kinase Assay

CDK2/CyclinE—inhibitory activity of compounds of the present invention was quantified employing the CDK2/CycE HTRF assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

CDK2/CycE was incubated for 60 min at 22° C. in the presence of different concentrations of test compounds in 5 µl assay buffer [50 mM Tris/HCl pH 8.0, 10 mM $MgCl_2$, 1.0 mM dithiothreitol, 0.1 mM sodium ortho-vanadate, 10 µM adenosine-tri-phosphate (ATP), 0.75 µM substrate, 0.01% (v/v) Nonidet-P40 (Sigma), 1% (v/v) dimethylsulfoxide]. The concentration of CDK2/CycE was adjusted depending of the activity of the enzyme lot and was chosen appropriate to have the assay in the linear range, typical concentrations were in the range of 1 ng/ml. The reaction was stopped by the addition of 5 µl of a solution of HTRF detection reagents (0.2 µM streptavidine-XLent and 3.4 nM Phospho-(Ser) CDKs Substrate Antibody [product #2324B, Cell Signaling Technology, Danvers, Mass., USA} and 4 nM Prot-A-EuK [Protein A labeled with Europium Cryptate from Cis biointernational, France, product no. 61PRAKLB]) in an aqueous EDTA-solution (100 mM EDTA, 800 mM KF, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Prot-A-EuK to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Assay 7: Aurora-C Kinase Assay

Aurora-C inhibitory activity of compounds of the present invention was quantified employing the Aurora-C HTRF assay as described in the following paragraphs.

Recombinant fusion protein of GST and human Aurora-C was expressed in transiently transfected HEK293 cells (Sf9) and purified by Glutathion-Sepharose affinity chromatography. As substrate for the kinase reaction biotinylated peptide biotin-Ttds-FMRLRRLSTKYRT (C-terminus in amid form) was used which can be purchased e.g. form the company JERINI peptide technologies (Berlin, Germany). Aurora-C was incubated for 60 min at 22° C. in the presence of different concentrations of test compounds in 5 µl assay buffer [25 mM Hepes/NaOH pH 7.4, 0.5 mM $MnCl_2$, 2.0 mM dithiothreitol, 0.1 mM sodium ortho-vanadate, 10 µM adenosine-tri-phosphate (ATP), 0.5 µM/ml substrate, 0.01% (v/v) TritonX-100 (Sigma), 0.05% (w/v) bovine serum albumin, 1% (v/v) dimethylsulfoxide]. The concentration of Aurora-C was adjusted depending of the activity of the enzyme lot and was chosen appropriate to have the assay in the linear range, typical concentrations were in the range of 0.3 nM. The reaction was stopped by the addition of 5 µl of a solution of HTRF detection reagents (0.2 µM streptavidine-XLent and 1.4 nM Anti-Phospho-(Ser/Thr) Akt substrate-Cryptate (C is biointernational, France, product no. $61PO_2KAE$), a labeled Phospho-(Ser/Thr) Akt substrate antibody [product #9611B, Cell Signaling Technology, Danvers, Mass., USA] labeled with Europium Cryptate, in an aqueous EDTA-solution (40 mM EDTA, 400 mM KF, 0.05% (w/v) bovine serum albumin in 25 mM HEPES/NaOH pH 7.0).

The resulting mixture was incubated 1 h at 22° C. to allow the binding of the biotinylated phosphorylated peptide to the streptavidine-XLent and the Anti-Phospho-(Ser/Thr) Akt substrate-Cryptate. Subsequently the amount of phosphorylated substrate was evaluated by measurement of the resonance energy transfer from the Prot-A-EuK to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Assay 8: Chk1 Kinase Assay

Checkpoint kinase 1 (Chk1)-inhibitory activity of compounds of the present invention was quantified employing the Chk1 HTRF assay as described in the following paragraphs.

C-terminally $His_6$-tagged human Chk1 kinase domain (amino acids 1-289) was expressed in insect cells (Hi5) and purified by Ni-NTA affinity chromatography and consecutive size exclusion chromatography (Superdex 75, 35/60, column from Amersham Bioscience, #17-1041) and used as kinase. Alternatively commercially available Chk1 protein from Invitrogen or Millipore can be used. As substrate for the kinase reaction biotinylated peptide biotin-ALKLVRTPS-FVITAK (C-terminus in amid form, "Chk1-tide") was used which can be purchased e.g. form the company Biosyntan (Berlin-Buch, Germany). Chk1 was incubated for 60 min at 22° C. in the presence of different concentrations of test compounds in 5 µl assay buffer [50 mM HEPES/NaOH pH 7.5, 10 mM $MgCl_2$, 1 mM $MnCl_2$, 1.0 mM dithiothreitol, 0.1 mM sodium ortho-vanadate, 10 µM adenosine-tri-phosphate (ATP), 1 µM substrate, 0.01% (v/v) Nonidet-P40 (Sigma), 1% (v/v) dimethylsulfoxide]. The concentration of Chk1 was adjusted depending on the activity of the enzyme lot and was chosen appropriate to have the assay in the linear range, typical concentrations were in the range of 100 ng/ml. The reaction was stopped by the addition of 5 µl of a solution of HTRF detection reagents (0.2 µM streptavidine-XLent and 3.4 nM Phospho-(Ser) Akt Substrate Antibody [product #9611B, Cell Signaling Technology, Danvers, Mass., USA] and 4 nM Prot-A-EuK [Protein A labeled with Europium Cryptate from Cis biointernational, France, product no. 61PRAKLB]) in an aqueous EDTA-solution (100 mM EDTA, 800 mM KF, 0.2% (w/v) bovine serum albumin in 100 mM HEPES/NaOH pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Prot-A-EuK to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Biological Data

Compounds of the present invention were found to possess enzymatic and cellular activity as inhibitors of Tie2 and VEGFR2 kinase. Preferred compounds of the present invention inhibit Tie2 and VEGFR2 kinase activity, cellular Tie2 autophosphorylation and VEGF-induced MVEC proliferation with $IC_{50}$ values below 1 µM, more preferred compounds inhibit Tie2 autophosphorylation and VEGF-induced MVEC proliferation with $IC_{50}$ values below 0.5 µM. Dual targeting of these two endothelial cell signalling pathways by compounds of the present invention is highly advantageous since VEGFR2 and Tie2 signalling have been shown to control distinct processes in the angiogenic formation of new blood vessels thereby maximising the anti-angiogenic effect of such compounds. Compounds of the present invention possess inhibitory selectivity for Tie2/KDR kinases versus kinases which modulate the cell cycle of proliferating cells, such as, for example, CDK2, Aurora kinases and Chk1.

Selected data are given in the following table.
-- stands for IC50>10 µM
- stands for $IC_{50}$=1 to 10 µM
+ stands for $IC_{50}$=500 to 1000 nM
++ stands for $IC_{50}$<500 nM

| # | Tie2 activity (assay 1) | Tie2 activity (assay 2) | KDR activity (assay 4) | EC proliferation (assay 5) | CDK2 activity (assay 6) | Aurora C activity (assay 7) |
|---|---|---|---|---|---|---|
| 1.1 | ++ | ++ | ++ | ++ | -- | -- |
| 1.2 | ++ | ++ | ++ | ++ | -- | -- |
| 1.3 | ++ | ++ | ++ | ++ | - | -- |
| 1.5 | ++ | ++ | ++ | ++ | - | -- |
| 1.8 | ++ | ++ | ++ | | -- | -- |
| 1.9 | ++ | ++ | ++ | ++ | -- | -- |
| 1.13 | ++ | ++ | ++ | ++ | -- | -- |
| 1.15 | ++ | ++ | ++ | | - | -- |
| 1.17 | ++ | ++ | ++ | | -- | -- |
| 1.18 | ++ | ++ | ++ | ++ | - | -- |
| 1.19 | ++ | ++ | ++ | ++ | | -- |
| 1.20 | ++ | ++ | ++ | ++ | | -- |
| 1.24 | ++ | ++ | ++ | | -- | - |
| 1.26 | ++ | ++ | ++ | | -- | - |
| 2.7 | ++ | ++ | ++ | ++ | - | - |
| 4.2 | ++ | ++ | ++ | | -- | -- |

The invention claimed is:

1. A compound of general formula (I):

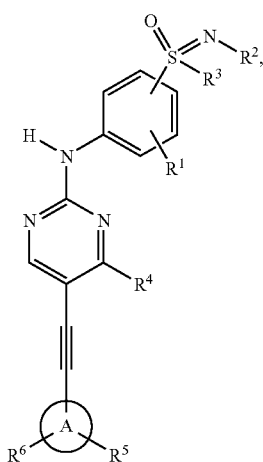

in which

R$^1$ is selected from the group consisting of hydrogen, halogen, nitro, cyano, —C$_1$-C$_6$-alkyl, —C$_1$-C$_6$-alkylthio, —C$_1$-C$_6$-haloalkyl, C$_3$-C$_{10}$-cycloalkyl, —(CH$_2$)$_m$OR$^c$, —(CH$_2$)$_m$NR$^{d1}$R$^{d2}$, and —(CH$_2$)$_m$C(O)R$^b$;

R$^2$ represents hydrogen, —C(O)R$^b$, —S(O)$_2$R$^b$, —P(O)(OR$^f$)$_2$, or —S(O)$_2$—(CH$_2$)$_2$—Si(R$^h$R$^k$R$^l$), or is selected from the group consisting of —C$_1$-C$_6$-alkyl, —C$_2$-C$_6$-alkenyl, —C$_2$-C$_6$-alkynyl, —C$_3$-C$_{10}$-cycloalkyl, aryl, heteroaryl and —C$_3$-C$_{10}$-heterocycloalkyl, wherein said residues are unsubstituted or substituted one or more times independently from each other with halogen, nitro, cyano, —C$_1$-C$_6$-alkyl, aryl, heteroaryl, —OR$^c$, —NR$^{d1}$R$^{d2}$—C$_1$-C$_6$-haloalkyl, —C(O)R$^b$, or —S(O)$_2$R$^b$;

R$^3$ is selected from the group consisting of —C$_1$-C$_6$-alkyl, —C$_2$-C$_6$-alkenyl, —C$_2$-C$_6$-alkynyl, aryl, heteraryl and —C$_3$-C$_{10}$-cycloalkyl, wherein said residues are unsubstituted or substituted one or more times independently from each other with halogen, nitro, cyano, —C$_1$-C$_6$-alkyl, aryl, heteraryl, —OR$^c$, —NR$^{d1}$R$^{d2}$, —C$_1$-C$_6$-haloalkyl, —C(O)R$^b$, or —S(O)$_2$R$^b$;

R$^4$ is selected from the group consisting of hydrogen, —OR$^7$, —SR$^7$ and —NR$^7$R$^8$;

R$^5$ is selected from the group consisting of hydrogen, halogen, nitro, cyano, —C$_1$-C$_6$-alkyl, —C$_3$-C$_{10}$-cycloalkyl, -C$_1$-C$_6$-haloalkyl, —C$_1$-C$_6$-alkylthio, —(CH$_2$)$_n$OR$^f$, —(CH$_2$)$_n$NR$^s$C(O)R$^m$, —(CH$_2$)$_n$NR$^s$S(O)$_2$R$^m$, —(CH$_2$)$_n$NR$^{g1}$R$^{g2}$, —(CH$_2$)$_n$C(O)R$^n$, and —(CH$_2$)$_n$S(O)$_2$R$^n$;

R$^6$ is selected from the group consisting of hydrogen, halogen, nitro, cyano, hydroxyl, -C$_1$-C$_6$-alkyl, C$_3$-C$_{10}$-cycloalkyl, —C$_1$-C$_6$-haloalkyl, —C$_1$-C$_6$-haloalkoxy, —C$_1$-C$_6$-alkoxy, and —C$_1$-C$_6$-alkylthio;

R$^7$, R$^8$ independently from each other are selected from the group consisting of hydrogen, —C$_1$-C$_6$-alkyl, —C$_2$-C$_6$-alkenyl, —C$_2$-C$_6$-alkynyl, —C$_3$-C$_{10}$-cycloalkyl, —(CH$_2$)$_p$-aryl, —(CH$_2$)$_p$-heteroaryl and —C$_3$-C$_{10}$-heterocycloalkyl, wherein said residues are unsubstituted or substituted one or more times independently from each other with halogen, nitro, cyano, —C$_1$-C$_6$-alkyl, —C$_3$-C$_{10}$-cycloalkyl, —C$_3$-C$_{10}$-heterocycloalkyl, aryl, heteroaryl, —OR$^c$, —NR$^{d1}$R$^{d2}$, —C$_1$-C$_6$-haloalkyl, —C(O)R$^b$, or —S(O)$_2$R$^b$; or R$^7$, R$^8$ in the context of a NR$^7$R$^8$ group together with the nitrogen atom to which they are attached, form a 3 to 10 membered heterocycloalkyl ring, which is optionally substituted one or more times, the same way or differently, with C$_1$-C$_6$-alkyl, —NR$^{g1}$R$^{g2}$—OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by NH, NR$^a$, oxygen or sulphur, and can optionally be interrupted one or more times, the same way or differently, with a —C(O)—, —S(O)—, and/or —S(O)$_2$-group, and can optionally contain one or more double bonds;

R$^a$ is selected from the group consisting of hydrogen, C$_1$-C$_6$-alkyl, C$_3$-C$_{10}$-cycloalkyl, C$_3$-C$_{10}$-heterocycloalkyl, aryl, and heteroaryl, wherein C$_1$-C$_6$-alkyl, and C$_3$-C$_{10}$-cycloalkyl are optionally substituted one or more times with hydroxyl, halogen, or C$_1$-C$_6$-alkoxy;

R$^b$ is selected from the group consisting of —OR$^c$, —SR$^c$, —NR$^{d1}$R$^{d2}$, aryl, heteroaryl, C$_1$-C$_6$-alkyl, and C$_3$-C$_{10}$-cycloalkyl, wherein C$_1$-C$_6$-alkyl, and C$_3$-C$_{10}$-cycloalkyl are optionally substituted one or more times with hydroxyl, halogen, —NR$^{g1}$R$^{g2}$or C$_1$-C$_6$-alkoxy;

R$^c$ is selected from the group consisting of hydrogen, —C(O)R$^e$, —S(O)$_2$R$^e$, —P(O)(OR$^f$)$_2$, C$_1$-C$_6$-alkyl, C$_1$-C$_6$-haloalkyl C$_3$-C$_{10}$-cycloalkyl, C$_3$-C$_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —$OR^f$, —$NR^{d1}R^{d2}$, or —$OP(O)(OR^f)_2$;

$R^{d1}$, $R^{d2}$ independently from each other are selected from the group consisting of hydrogen, $C_1$-$C_6$-alkyl, $C_3$-$C_{10}$-cycloalkyl, $C_3$-$C_{10}$-heterocycloalkyl, aryl, and heteroaryl, or a group —$C(O)R^e$ or —$S(O)_2R^e$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxyl, aryl, —$C_1$-$C_6$-alkyl, —$NR^{g1}R^{g2}$, —$OR^f$, —$C(O)R^e$, —$S(O)_2R^e$, or —$OP(O)(OR^f)_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^e$ is selected from the group consisting of, —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is selected from the group consisting of hydrogen, —$C(O)R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group consisting of hydrogen, $C_1$-$C_6$-alkyl, $C_3$-$C_{10}$-cycloalkyl, and $C_3$-$C_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^h$, $R^k$, and $R^l$ independently from each other represent —$C_1$-$C_6$-alkyl or phenyl;

$R^m$ is selected from the group consisting of $C_1$-$C_6$-alkyl, $C_3$-$C_{10}$-cycloalkyl and $C_3$-$C_{10}$-heterocycloalkyl;

$R^n$ is selected from the group consisting of —$NR^{g1}R^{g2}$, $C_1$-$C_6$-alkyl, $C_3$-$C_6$-cycloalkyl, hydroxyl and $C_1$-$C_6$-alkoxy;

$R^s$ represents hydrogen or $C_1$-$C_6$-alkyl

A represents aryl or heteroaryl;

m represent an integer of 0, 1 or 2;

n represent an integer of 0, 1 or 2;

p represent an integer of 0, 1 or 2;

wherein each occurrence of $R^a$, $R^b$, $R^c$, $R^{d1}$, $R^{d2}$, $R^e$, $R^f$, $R^{g1}$ or $R^{g2}$ may be the same or different;

or a salt or tautomer thereof.

2. The compound according to claim 1, wherein:

$R^1$ represents hydrogen;

$R^2$ represents hydrogen, —$C(O)R^b$, —$S(O)_2R^b$, —$P(O)(OR^f)_2$, or —$S(O)_2$—$(CH_2)_2$—$Si(R^hR^kR^l)$, or is selected from the group consisting of —$C_1$-$C_6$-alkyl, —$C_2$-$C_6$-alkenyl, —$C_2$-$C_6$-alkynyl, —$C_3$-$C_{10}$-cycloalkyl, aryl, heteroaryl and —$C_3$-$C_{10}$-heterocycloalkyl, wherein said residues are unsubstituted or substituted one or more times independently from each other with halogen, nitro, cyano, —$C_1$-$C_6$-alkyl, aryl, heteroaryl, —$OR^c$, —$NR^{d1}R^{d2}$, —$C_1$-$C_6$-haloalkyl, —$C(O)R^b$, or —$S(O)_2R^b$;

$R^3$ is selected from the group consisting of —$C_1$-$C_6$-alkyl, —$C_2$-$C_6$-alkenyl, —$C_2$-$C_6$-alkynyl, aryl, hetaryl and —$C_3$-$C_{10}$-cycloalkyl, wherein said residues are unsubstituted or substituted one or more times independently from each other with halogen, nitro, cyano, —$C_1$-$C_6$-alkyl, aryl hetaryl, —$OR^c$, —$NR^{d1}R^{d2}$, —$C_1$-$C_6$-haloalkyl, —$C(O)R^b$, or —$S(O)_2R^b$;

$R^4$ is selected from the group consisting of hydrogen, —$OR^7$, —$SR^7$ and —$NR^7R^8$;

$R^5$ is selected from the group consisting of hydrogen, halogen, nitro, cyano, —$C_1$-$C_6$-alkyl, —$C_3$-$C_{10}$-cycloalkyl, —$C_1$-$C_6$-haloalkyl, —$C_1$-$C_6$-alkylthio, —$(CH_2)_nOR^f$, —$(CH_2)_nNR^cC(O)R^m$, —$(CH_2)_nNR^sS(O)_2R^m$, —$(CH_2)_nNR^{g1}R^{g2}$, —$(CH_2)_nC(O)R^n$, and —$(CH_2)_nS(O)_2R^n$;

$R^6$ is selected from the group consisting of hydrogen, halogen, nitro, cyano, hydroxyl, —$C_1$-$C_6$-alkyl, —$C_3$-$C_{10}$-cycloalkyl, —$C_1$-$C_6$-haloalkyl, —$C_1$-$C_6$-haloalkoxy, —$C_1$-$C_6$-alkoxy, and —$C_1$-$C_6$-alkylthio;

$R^7$, $R^8$ independently from each other are selected from the group consisting of hydrogen, —$C_1$-$C_6$-alkyl, —$C_2$-$C_6$-alkenyl, —$C_2$-$C_6$-alkynyl, —$C_3$-$C_{10}$-cycloalkyl, —$(CH_2)_p$-aryl, -$(CH_2)_p$-heteroaryl and —$C_3$-$C_{10}$-heterocycloalkyl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, aryl, heteroaryl, —$OR^c$, —$NR^{d1}R^{d2}$, —$C_1$-$C_6$-haloalkyl, —$C(O)R^b$, or —$S(O)_2R^b$; or $R^7$, $R^8$ in the context of a $NR^7R^8$ group together with the nitrogen atom to which they are attached, form a 3 to 10 membered heterocycloalkyl ring, which is optionally substituted one or more times, the same way or differently, with $C_1$-$C_6$-alkyl, $NR^{g1}R^{g2}$, $OR^f$, $C(O)R^e$, —$S(O)_2R^e$, or —$OP(O)(OR^f)_2$; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a -C(O)—, —S(O)—, and/or -$S(O)_2$-group, and can optionally contain one or more double bonds;

$R^a$ is selected from the group consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^b$ is selected from the group consisting of —$OR^c$, —$SR^c$, —$NR^{d1}R^{d2}$, aryl, heteroaryl, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, —$NR^{g1}R^{g2}$ or $C_1$-$C_6$-alkoxy;

$R^c$ is selected from the group consisting of hydrogen, —$C(O)R^e$, —$S(O)_2R^e$, —$P(O)(OR^f)_2$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —$OR^f$, —$NR^{d1}R^{d2}$, or —$OP(O)(OR^f)_2$;

$R^{d1}$, $R^{d2}$ independently from each other are selected from the group consisting of hydrogen, $C_1$-$C_6$-alkyl, $C_3$-$C_{10}$-cycloalkyl, $C_3$-$C_{10}$-heterocycloalkyl, aryl, and heteroaryl, or for a group —$C(O)R^e$ or —$S(O)_2R^e$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$C_1$-$C_6$-alkyl, —$NR^{g1}R^{g2}$, —$OR^f$, —$C(O)R^e$, —$S(O)_2R^e$, or —$OP(O)(OR^f)_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^e$ is selected from the group consisting of —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is selected from the group consisting of hydrogen, —$C(O)R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group consisting of hydrogen, $C_1$-$C_6$-alkyl, $C_3$-$C_{10}$-cycloalkyl, and $C_3$-$C_{10}$-heterocycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^h$, $R^k$, and $R^i$ independently from each other represent —$C_1$-$C_6$-alkyl or phenyl;

$R^m$ is selected from the group consisting of $C_1$-$C_6$-alkyl, $C_3$-$C_{10}$-cycloalkyl and $C_3$-$C_{10}$-heterocycloalkyl;

$R^n$ is selected from the group consisting of —$NR^{g1}R^{g2}$, $C_1$-$C_6$-alkyl, $C_3$-$C_6$-cycloalkyl, hydroxyl and $C_1$-$C_6$-alkoxy;

$R^s$ represents hydrogen or $C_1$-$C_6$-alkyl

A represents aryl or heteroaryl;

n represent an integer of 0, 1 or 2;

p represent an integer of 0, 1 or 2;

wherein each occurrence of $R^a$, $R^b$, $R^c$, $R^{d1}$, $R^{d2}$, $R^e$, $R^f$, $R^{g1}$ or $R^{g2}$ may be the same or different;

or a salt or tautomer thereof.

3. The compound according to claim 1, wherein:

$R^1$ represents hydrogen;

$R^2$ represents hydrogen, —$C(O)R^b$, or is selected from the group consisting of —$C_1$-$C_6$-alkyl, —$C_3$-$C_6$-cycloalkyl, aryl and —$C_3$-$C_6$-heterocycloalkyl, wherein said residues are unsubstituted or substituted once with halogen, cyano, —$C_1$-$C_6$-alkyl, —$OR^c$, —$NR_{d1}R^{d2}$, —$C_1$-$C_6$-haloalkyl;

$R^3$ is selected from the group consisting of —$C_1$-$C_6$-alkyl, —$C_2$-$C_6$-alkenyl, —$C_2$-$C_6$-alkynyl, aryl, heteraryl and —$C_3$-$C_{10}$-cycloalkyl, wherein said residues are unsubstituted or substituted one or more times independently from each other with halogen, nitro, cyano, —$C_1$-$C_6$-alkyl, aryl, heteraryl, —$OR^c$, —$NR^{d1}R^{d2}$, —$C_1$-$C_6$-haloalkyl, —$C(O)R^b$, or —$S(O)_2R^b$;

$R^4$ is selected from the group consisting of hydrogen, —$OR^7$, —$SR^7$ and —$NR^7R^8$;

$R^5$ is selected from the group consisting of hydrogen, halogen, nitro, cyano, —$C_1$-$C_6$-alkyl, —$C_3$-$C_{10}$-cycloalkyl, —$C_1$-$C_6$-haloalkyl, —$C_1$-$C_6$-alkylthio, —$(CH_2)OR^f$, —$(CH_2)_nNR^cC(O)R^m$, —$(CH_2)_nNR^sS(O)_2R^m$, —$(CH_2)_nNR^{g1}R^{g2}$, —$(CH_2)_nC(O)R^n$, and —$(CH_2)_nS(O)_2R^n$;

$R^6$ is selected from the group consisting of hydrogen, halogen, nitro, cyano, hydroxyl, —$C_1$-$C_6$-alkyl, —$C_3$-$C_{10}$-cycloalkyl, —$C_1$-$C_6$-haloalkyl, —$C_1$-$C_6$-haloalkoxy, —$C_1$-$C_6$-alkoxy, and -$C_1$-$C_6$-alkylthio;

$R^7$, $R^8$ independently from each other are selected from the group consisting of hydrogen, —$C_1$-$C_6$-alkyl, —$C_2$-$C_6$-alkenyl, —$C_2$-$C_6$-alkynyl, —$C_3$-$C_{10}$-cycloalkyl, —$(CH_2)_p$-aryl, —$(CH_2)_p$-heteroaryl and —$C_3$-$C_{10}$-heterocycloalkyl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, aryl, heteroaryl, —$OR^c$, —$NR^{d1}R^{d2}$, $C_1$-$C_6$-haloalkyl, —$C(O)R^b$, or —$S(O)_2R^b$; or $R^7$, $R^8$ in the context of a $NR^7R^8$ group together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$—$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^a$ is selected from the group consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^b$ is selected from the group consisting of —$OR^c$, —$SR^c$, —$NR^{d1}R^{d2}$ aryl, heteroaryl, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, —$NR^{g1}R^{g2}$ or $C_1$-$C_6$-alkoxy;

$R^c$ is selected from the group consisting of hydrogen, —$C(O)R^e$, —$S(O)_2R^e$, —$P(O)(OR^f)_2$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —OR$^f$, —NR$^{d1}$R$^{d2}$, or —OP(O)(OR$^f$)$_2$;

R$^{d1}$, R$^{d2}$ independently from each other are selected from the group consisting of hydrogen, C$_1$-C$_6$-alkyl, C$_3$-C$_{10}$-cycloalkyl, C$_3$-C$_{10}$-heterocycloalkyl, aryl, and heteroaryl, or a group —C(O)R$^e$ or —S(O)$_2$R$^e$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —C$_1$-C$_6$-alkyl, —NR$^{g1}$R$^{g2}$, —OR$^f$, —C(O)R$^e$, —S(O)$_2$R$^e$, or —OP(O)(OR$^f$)$_2$; or R$^{d1}$ and R$^{d2}$ together with the nitrogen atom to which they are attached, form a 3 to 10 membered heterocycloalkyl ring, which is optionally substituted one or more times, the same way or differently, with C$_1$-C$_6$-alkyl, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by NH, NR$^a$, oxygen or sulphur, and can optionally be interrupted one or more times, the same way or differently, with a —C(O)—, —S(O)—, and/or —S(O)$_2$-group, and can optionally contain one or more double bonds;

R$^e$ is selected from the group consisting of —NR$^{g1}$R$^{g2}$, C$_1$-C$_6$-alkyl, C$_3$-C$_6$-cycloalkyl, C$_1$-C$_6$-alkoxy, aryl and heteroaryl;

R$^f$ is selected from the group consisting of hydrogen, —C(O)R$^e$, C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, C$_1$-C$_6$-alkoxy, aryl, or —NR$^{g1}$R$^{g2}$;

R$^{g1}$, R$^{g2}$ independently from each other are selected from the group consisting of hydrogen, C$_1$-C$_6$-alkyl, C$_3$-C$_{10}$-cycloalkyl, C$_3$-C$_{10}$-heterocycloalkyl; or R$^{g1}$ and R$^{g2}$ together with the nitrogen atom to which they are attached, form a 3 to 10 membered heterocycloalkyl ring, which is optionally substituted one or more times, the same way or differently, with C$_1$-C$_6$-alkyl, —C$_1$-C$_6$-alkoxy, or hydroxy; whereby the carbon backbone of this heterocycloalkyl ring can optionally be interrupted one or more times, the same way or differently, by NH, NR$^a$, oxygen or sulphur, and can optionally be interrupted one or more times, the same way or differently, with a —C(O)—, —S(O)—, and/or —S(O)$_2$-group, and can optionally contain one or more double bonds;

R$^m$ is selected from the group consisting of C$_1$-C$_6$-alkyl, C$_3$-C$_{10}$-cycloalkyl and C$_3$-C$_{10}$-heterocycloalkyl;

R$^n$ is selected from the group consisting of —NR$^{g1}$R$^{g2}$, —C$_1$-C$_6$-alkyl, C$_3$-C$_6$-cycloalkyl, hydroxyl and —C$_1$-C$_6$-alkoxy;

R$^s$ represents hydrogen or C$_1$-C$_6$-alkyl

A represents aryl or heteroaryl;

n represent an integer of 0, 1 or 2;

P represent an integer of 0, 1 or 2;

wherein each occurrence of R$^a$, R$^b$, R$^c$, R$^{d1}$, R$^{d2}$, R$^e$, R$^f$, R$^{g1}$ or R$^{g2}$ may be the same or different;

or a salt or tautomer thereof.

4. The compound according to any claim 1, wherein:

R$^1$ represents hydrogen;

R$^2$ represents hydrogen, —C(O)R$^b$, or is selected from the group consisting of —C$_1$-C$_6$-alkyl, —C$_3$-C$_6$-cycloalkyl, aryl and —C$_3$-C$_6$-heterocycloalkyl, wherein said residues are unsubstituted or substituted once with halogen, cyano, —C$_1$-C$_6$-alkyl, —OR$^c$, —NR$^{d1}$R$^{d2}$, C$_1$-C$_6$-haloalkyl;

R$^3$ is selected from the group consisting of —C$_1$-C$_6$-alkyl, phenyl and —C$_3$-C$_6$-cycloalkyl, wherein said residues are unsubstituted or substituted once with halogen, cyano, —C$_1$-C$_6$-alkyl, —OR$^c$, —NR$^{d1}$R$^{d2}$, —C$_1$-C$_6$-haloalkyl;

R$^4$ is selected from the group consisting of hydrogen, —OR$^7$, —SR$^7$ and —NR$^7$R$^8$;

R$^5$ is selected from the group consisting of hydrogen, halogen, nitro, cyano, —C$_1$-C$_6$-alkyl, —C$_3$-C$_{10}$-cycloalkyl, —C$_1$-C$_6$-haloalkyl, —C$_1$-C$_6$-alkylthio, —(CH$_2$)OR$^f$, —(CH$_2$)$_n$NR$^s$C(O)R$^m$, —(CH$_2$)$_n$NR$^s$S(O)$_2$R$^m$, —(CH$_2$)$_n$NR$^{g1}$R$^{g2}$, —(CH$_2$)$_n$C(O)R$^n$, and —(CH$_2$)$_n$S(O)$_2$R$^n$;

R$^6$ is selected from the group consisting of hydrogen, halogen, nitro, cyano, hydroxyl, —C$_1$-C$_6$-alkyl, —C$_3$-C$_{10}$-cycloalkyl, —C$_1$-C$_6$-haloalkyl, —C$_1$-C$_6$-haloalkoxy, —C$_1$-C$_6$-alkoxy, and —C$_1$-C$_6$-alkylthio;

R$^7$, R$^8$ independently from each other are selected from the group consisting of hydrogen, —C$_1$-C$_6$-alkyl, —C$_2$-C$_6$-alkenyl, —C$_2$-C$_6$-alkynyl, —C$_3$-C$_{10}$-cycloalkyl, —(CH$_2$)$_p$-aryl, —(CH$_2$)$_p$-heteroaryl and —C$_3$-C$_{10}$-heterocycloalkyl, wherein said residues are unsubstituted or substituted one or more times independently from each other with halogen, nitro, cyano, —C$_1$-C$_6$-alkyl, —C$_3$-C$_{10}$-cycloalkyl, —C$_3$-C$_{10}$-heterocycloalkyl, aryl, heteroaryl, —OR$^c$, —NR$^{d1}$R$^{d2}$, —C$_1$-C$_6$-haloalkyl, —C(O)R$^b$, or —S(O)$_2$R$^b$; or R$^7$, R$^8$ in the context of a NR$^7$R$^8$ group together with the nitrogen atom to which they are attached, form a 3 to 10 membered heterocycloalkyl ring, which is optionally substituted one or more times, the same way or differently, with C$_1$-C$_6$-alkyl, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by NH, NR$^a$, oxygen or sulphur, and can optionally be interrupted one or more times, the same way or differently, with a —C(O)—, —S(O)—, and/or —S(O)$_2$-group, and can optionally contain one or more double bonds;

R$^a$ is selected from the group consisting of hydrogen, C$_1$-C$_6$-alkyl, C$_3$-C$_{10}$-cycloalkyl, C$_3$-C$_{10}$-heterocycloalkyl, aryl, and heteroaryl, wherein C$_1$-C$_6$-alkyl, and C$_3$-C$_{10}$-cycloalkyl are optionally substituted one or more times with hydroxyl, halogen, or C$_1$-C$_6$-alkoxy;

R$^b$ is selected from the group consisting of —OR$^c$, —SR$^c$, —NR$^{d1}$R$^{d2}$, aryl, heteroaryl, C$_1$-C$_6$-alkyl, and C$_3$-C$_{10}$-cycloalkyl, wherein C$_1$-C$_6$-alkyl, and C$_3$-C$_{10}$-cycloalkyl are optionally substituted one or more times with hydroxyl, halogen, —NR$^{g1}$R$^{g2}$ or C$_1$-C$_6$-alkoxy;

R$^c$ is selected from the group consisting of hydrogen, —C(O)R$^e$, —S(O)$_2$R$^e$, —P(O)(OR$^f$)$_2$, C$_1$-C$_6$-alkyl, C$_1$-C$_6$-haloalkyl C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with halogen, aryl, —OR$^f$, —NR$^{d1}$R$^{d2}$, or —OP(O)(OR$^f$)$_2$;

R$_{d1}$, R$^{d2}$ independently from each other are selected from the group consisting of hydrogen, C$_1$-C$_6$-alkyl, C$_3$-C$_{10}$-cycloalkyl, C$_3$-C$_{10}$-heterocycloalkyl, aryl, and heteroaryl, or for a group —C(O)R$^e$ or —S(O)$_2$R$^e$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —$C_1$-$C_6$-alkyl, —$NR^{g1}R^{g2}$, —$OR^f$, —$C(O)R^e$, —$S(O)_2R^e$, or —$OP(O)(OR^f)_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^e$ is selected from the group consisting of —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is selected from the group consisting of hydrogen, —$C(O)R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group consisting of hydrogen, $C_1$-$C_6$-alkyl, $C_3$-$C_{10}$-cycloalkyl, $C_3$-$C_{10}$-hetero cycloalkyl; or $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, or hydroxy; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —$S(O)_2$-group, and can optionally contain one or more double bonds;

$R^m$ is selected from the group consisting of $C_1$-$C_6$-alkyl, $C_3$-$C_{10}$-cycloalkyl and $C_3$-$C_{10}$-heterocycloalkyl;

$R^n$ is selected from the group consisting of —$NR^{g1}R^{g2}$, $C_1$-$C_6$-alkyl, $C_3$-$C_6$-cycloalkyl, hydroxyl and $C_1$-$C_6$-alkoxy;

$R^s$ represents hydrogen or $C_1$-$C_6$-alkyl

A represents aryl or heteroaryl;

n represent an integer of 0, 1 or 2;

p represent an integer of 0, 1 or 2;

wherein each occurrence of $R^a$, $R^b$, $R^c$, $R^{d1}$, $R^{d2}$, $R^e$, $R^f$, $R^{g1}$ or $R^{g2}$ may be the same or different;

or a salt or tautomer thereof.

5. The compound according to claim 1, wherein:

$R^1$ represents hydrogen;

$R^2$ represents hydrogen, —$C(O)R^b$, or is selected from the group consisting of —$C_1$-$C_6$-alkyl, —$C_3$-$C_6$-cycloalkyl, wherein said residues are unsubstituted or substituted once with $C_1$-$C_6$-alkyl, —$OR^c$, or —$NR^{d1}R^{d2}$;

$R^3$ is selected from the group consisting of —$C_1$-$C_6$-alkyl, phenyl and —$C_3$-$C_6$-cycloalkyl, wherein said residues are unsubstituted or substituted once with halogen, —$C_1$-$C_6$-alkyl, —$OR^c$, or —$NR^{d1}R^{d2}$;

$R^4$ is selected from the group consisting of hydrogen, —$OR^7$, —$SR^7$ and —$NR^7R^8$;

$R^5$ is selected from the group consisting of hydrogen, halogen, nitro, cyano, —$C_1$-$C_6$-alkyl, —$C_3$-$C_{10}$-cycloalkyl, —$C_1$-$C_6$-haloalkyl, —$C_1$-$C_6$-alkylthio, —$(CH_2)OR^f$, —$(CH_2)_nNR^sC(O)R^m$, —$(CH_2)_nNR^sS(O)_2R^m$, —$(CH_2)_nNR^{g1}R^{g2}$, —$(CH_2)_nC(O)R^n$, and —$(CH_2)_nS(O)_2R^n$;

$R^6$ is selected from the group consisting of hydrogen, halogen, nitro, cyano, hydroxyl, —$C_1$-$C_6$-alkyl, —$C_3$-$C_{10}$-cycloalkyl, —$C_1$-$C_6$-haloalkyl, —$C_1$-$C_6$-haloalkoxy, —$C_1$-$C_6$-alkoxy, and -$C_1$-$C_6$-alkylthio;

$R^7$, $R^8$ independently from each other are selected from the group consisting of hydrogen, —$C_1$-$C_6$-alkyl, —$C_2$-$C_6$-alkenyl, —$C_2$-$C_6$-alkenyl, —$C_3$-$C_{10}$-cycloalkyl, —$(CH_2)_p$-aryl, —$(CH_2)_p$-heteroaryl and —$C_3$-$C_{10}$-heterocycloalkyl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, aryl, heteroaryl, —$OR^c$, —$NR_{d1}R_{d2}$, —$C_1$-$C_6$-haloalkyl, —$C(O)R^b$, or —$S(O)_2R^b$; or $R^7$, $R^8$ in the context of a $NR^7R^8$ group together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$, —$OR^f$, —$C(O)R^e$, —$S(O)_2R^e$, or —$OP(O)(OR^f)_2$; whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—,—S(O)—, and/or —$S(O)_2$-group, and can optionally contain one or more double bonds;

$R^a$ is selected from the group consisting of hydrogen, $C_1$-$C_6$-alkyl, $C_3$-$C_{10}$-cycloalkyl, $C_3C_{10}$-heterocycloalkyl, aryl, and heteroaryl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^b$ is selected from the group consisting of —$OR^c$, —$SR^c$, —$NR^{d1}R^{d2}$, aryl, heteroaryl, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, —$NR^{g1}R^{g2}$ or $C_1$-$C_6$-alkoxy;

$R^c$ is selected from the group consisting of hydrogen, —$C(O)R^e$, —$S(O)_2R^e$, —$P(O)(OR^f)_2$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with halogen, aryl, —$OR^f$, —$NR^{d1}R^{d2}$, or —$OP(O)(OR^f)_2$;

$R^{d1}$, $R^{d2}$ independently from each other are selected from the group consisting of hydrogen, $C_1$-$C_6$-alkyl, $C_3$-$C_{10}$-cycloalkyl, $C_3$-$C_{10}$-heterocycloalkyl, aryl, and heteroaryl, or for a group —$C(O)R^e$ or —$S(O)_2R^e$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$C_1$-$C_6$-alkyl, —$NR^{g1}R^{g2}OR^f$, —$C(O)R^e$, —$S(O)_2R^e$, or —$OP(O)(OR^f)_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, —$NR^{g1}R^{g2}$—$OR^f$, —$C(O)R^e$, —$S(O)_2R^e$, or —$OP(O)(OR^f)_2$;

whereby the carbon backbone of this heterocycloalkyl ring can optionally be interrupted one or more times, the same way or differently, by NH, $NR^a$, oxygen or sulphur, and can optionally be interrupted one or more times, the same way or differently, with a —C(O)—, —S(O)—, and/or —S(O)$_2$- group, and can optionally contain one or more double bonds;

$R^e$ is selected from the group consisting of —NR$^{g1}$R$^{g2}$, C$_1$-C$_6$-alkyl, C$_3$-C$_6$-cycloalkyl, C$_1$-C$_6$-alkoxy, aryl and heteroaryl;

$R^f$ is selected from the group consisting of hydrogen, —C(O)R$^e$, C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, C$_1$-C$_6$-alkoxy, aryl, or —NR$^{g1}$R$^{g2}$;

R$^{g1}$, R$^{g2}$ independently from each other are selected from the group consisting of hydrogen, C$_1$-C$_6$-alkyl, C$_3$-C$_{10}$-cycloalkyl, C$_3$-C$_{10}$-hetero cycloalkyl; or R$^{g1}$ and R$^{g2}$ together with the nitrogen atom to which they are attached, form a 3 to 10 membered heterocycloalkyl ring, which is optionally substituted one or more times, the same way or differently, with C$_1$-C$_6$-alkyl, —C$_1$-C$_6$-alkoxy, or hydroxy; whereby the carbon backbone of this heterocycloalkyl ring can optionally be interrupted one or more times, the same way or differently, by NH, NR$^a$, oxygen or sulphur, and can optionally be interrupted one or more times, the same way or differently, with a —C(O)—, —S(O)—, and/or —S(O)$_2$-group, and can optionally contain one or more double bonds;

R''' is selected from the group consisting of C$_1$-C$_6$-alkyl, C$_3$-C$_{10}$-cycloalkyl and C$_3$-C$_{10}$-heterocycloalkyl;

R'' is selected from the group consisting of —NR$^{g1}$R$^{g2}$, C$_1$-C$_6$-alkyl, C$_3$-C$_6$-cycloalkyl, hydroxyl and C$_1$-C$_6$-alkoxy;

R$^s$ represents hydrogen or C$_1$-C$_6$-alkyl

A represents aryl or heteroaryl;

n represent an integer of 0, 1 or 2;

p represent an integer of 0, 1 or 2;

wherein each occurrence of R$^a$, R$^b$, R$^c$, R$^{d1}$, R$^{d2}$, R$^e$, R$^f$, R$^{g1}$ or R$^{g2}$ may be the same or different;

or a salt or tautomer thereof.

6. The compound according to claim 1 selected from the group consisting of :

(RS)-S-(4-[4-((R)-2-Hydroxy-1-methyl-ethylamino)-5-(4-methoxy-phenylethynyl)-pyrimidin-2-ylamino]-phenyl)-S-methylsulfoximide;

(RS)-S-(4-[4-((R)-2-Hydroxy-1-methyl-ethylamino)-5-(phenylethynyl)-pyrimidin-2-ylamino]-phenyl)-S-methylsulfoximide;

(RS)-S-(4-[4-((R)-2-Hydroxy-1-methyl-ethylamino)-5-(2-methyl-phenylethynyl)-pyrimidin-2-ylamino]-phenyl)-S-methylsulfoximide;

(RS)-S-(4-[4-((R)-2-Hydroxy-1-methyl-ethylamino)-5-(3-methyl-phenylethynyl)-pyrimidin-2-ylamino]-phenyl)-S-methylsulfoximide;

(RS)-S-(4-[4-((R)-2-Hydroxy-1-methyl-ethylamino)-5-(4-methyl-phenylethynyl)-pyrimidin-2-ylamino]-phenyl)-S-methylsulfoximide;

(RS)-S-(4-[4-((R)-2-Hydroxy-1-methyl-ethylamino)-5-(2-methoxy-phenylethynyl)-pyrimidin-2-ylamino]-phenyl)-S-methylsulfoximide;

(RS)-S-(4-[4-((R)-2-Hydroxy-1-methyl-ethylamino)-5-(3-methoxy-phenylethynyl)-pyrimidin-2-ylamino]-phenyl)-S-methylsulfoximide;

(RS)-S-(4-[5-(4-Ethyl-phenylethynyl)-4-((R)-2-hydroxy-1-methyl-ethylamino)-pyrimidin-2-ylamino]-phenyl)-S-methylsulfoximide;

(RS)-S-(4-[5-(4-Fluoro-phenyl-ethynyl)-4-((R)-2-hydroxy-1-methyl-ethylamino)-pyrimidin-2-ylamino]-phenyl)-S-methylsulfoximide;

(RS)-S-(4-[5-(4-Cyano-phenyl-ethynyl)-4-((R)-2-hydroxy-1-methyl-ethylamino)-pyrimidin-2-ylamino]-phenyl)-S-methylsulfoximide;

(RS)-S-(4-[5-(3,5-Dimethoxy-phenylethynyl)-4-((R)-2-hydroxy-1-methyl-ethylamino)-pyrimidin-2-ylamino]-phenyl)-S-methylsulfoximide;

(RS)-S-(4-[4-((R)-2-Hydroxy-1-methyl-ethylamino)-5-(4-methoxy-2-methyl-phenylethynyl)-pyrimidin-2-ylamino]-phenyl)-S-methylsulfoximide;

(RS)-S-(4-[5-(4-Fluoro-3-methyl-phenyl-ethynyl)-4-((R)-2-hydroxy-1-methyl-ethylamino)-pyrimidin-2-ylamino]-phenyl)-S-methylsulfoximide;

(RS)-S-(4-[4-((R)-2-Hydroxy-1-methyl-ethylamino)-5-(3-hydroxy-phenylethynyl)-pyrimidin-2-ylamino]-phenyl)-S-methylsulfoximide;

(RS)-S-(3-[4-((R)-2-Hydroxy-1-methyl-ethylamino)-5-(3-hydroxy-phenylethynyl)-pyrimidin-2-ylamino]-phenyl)-N-(isopropylcarbamoyl)-S-methylsulfoximide;

(RS)-S-(3-[4-((R)-2-Hydroxy-1-methyl-ethylamino)-5-(phenylethynyl)-pyrimidin-2-ylamino]-phenyl)-S-methylsulfoximide;

(RS)-S-(3-[4-((R)-2-Hydroxy-1-methyl-ethylamino)-5-(4-methoxy-phenylethynyl)-pyrimidin-2-ylamino]-phenyl)-S-methylsulfoximide;

(RS)-S-(3-[4-((R)-2-Hydroxy-1-methyl-ethylamino)-5-(3-hydroxy-phenylethynyl)-pyrimidin-2-ylamino]-phenyl)-S-methylsulfoximide;

(RS)-S-(3-[4-((R)-2-Hydroxy-1-methyl-ethylamino)-5-(2-methyl-phenylethynyl)-pyrimidin-2-ylamino]-phenyl)-S-methylsulfoximide;

(RS)-S-(3-[5-(4-Fluoro-3-methyl-phenyl-ethynyl)-4-((R)-2-hydroxy-1-methyl-ethylamino)-pyrimidin-2-ylamino]-phenyl)-S-methylsulfoximide;

(RS)-S-(3-[4-((R)-2-Hydroxy-1-methyl-ethylamino)-5-(3-methoxy-phenylethynyl)-pyrimidin-2-ylamino]-phenyl)-S-methylsulfoximide;

(RS)-S-(3-[4-((R)-2-Hydroxy-1-methyl-ethylamino)-5-(4-methyl-phenylethynyl)-pyrimidin-2-ylamino]-phenyl)-S-methylsulfoximide;

(RS)-S-(4-[5-(4-Fluoro-3-methyl-phenyl-ethynyl)-4-methylamino-pyrimidin-2-ylamino]-phenyl)-S-methylsulfoximide;

(RS)-S-(4-[4-ethylamino-5-(4-fluoro-3-methyl-phenyl-ethynyl)-pyrimidin-2-ylamino]-phenyl)-S-methylsulfoximide;

(RS)-S-(4-[5-(4-methoxy-phenyl-ethynyl)-4-methylamino-pyrimidin-2-ylamino]-phenyl)-S-methylsulfoximide;

(RS)-S-(4-[4-ethylamino-5-(4-methoxy-phenyl-ethynyl)-pyrimidin-2-ylamino]-phenyl)-S-methylsulfoximide;

(RS)-S-4-[4-((R)-2-Hydroxy-1-methyl-ethylamino)-5-(1H-indazol-6-ylethynyl)-pyrimidin-2-ylamino]-phenyl)-S-methylsulfoximide;

(RS)-S-4-[4-((R)-2-Hydroxy-1-methyl-ethylamino)-5-(1H-indazol-5-ylethynyl)-pyrimidin-2-ylamino]-phenyl)-S-methylsulfoximide;

(RS)-S-4-[4-((R)-2-Hydroxy-1-methyl-ethylamino)-5-(1H-indazol-4-ylethynyl)-pyrimidin-2-ylamino]-phenyl)-S-methylsulfoximide;

(RS)-S-4-[5-(3-Benzyloxy-phenylethynyl)-4-((R)-2-hydroxy-1-methyl-ethylamino)-pyrimidin-2-ylamino]-S-methylsulfoximide;

(RS)-N-(Ethoxycarbonyl)-S-4-[4-((R)-2-Hydroxy-1-methyl-ethylamino)-5-(pyridin-3-ylethynyl)-pyrimidin-2-ylamino]-phenyl)-S-methyl-sulfoximide;

(RS)-N-(Ethoxycarbonyl)-S-(4-[4((R)-2-Hydroxy-1-methyl-ethylamino)-5-(2-methyl-phenylethynyl)-pyrimidin-2-ylamino]-phenyl)-S-methylsulfoximide;

(RS)-N-(Ethoxycarbonyl)-S-(4-[4-((R)-2-Hydroxy-1-methyl-ethylamino)-5-(4-methoxy-phenylethynyl)-pyrimidin-2-ylamino]-phenyl)-S-methylsulfoximide;

(RS)-N-(Ethoxycarbonyl)-S-(4-[4-((R)-2-Hydroxy-1-methyl-ethylamino)-5-(phenylethynyl)-pyrimidin-2-ylamino]-phenyl)-S-methylsulfoximide;

(RS)-N-(Ethoxycarbonyl)-S-(4-[5-(4-dimethyl-aminophenyl-ethynyl)-4((R)-2-hydroxy-1-methyl-ethylamino)-pyrimidin-2-ylamino]-phenyl)-S-methylsulfoximide;

(RS)-N-(Ethoxycarbonyl)-S-(4-[5-(4-cyanophenyl-ethynyl)-4-((R)-2-hydroxy-1-methyl-ethylamino)-pyrimidin-2-ylamino]-phenyl)-S-methylsulfoximide;

(RS)-N-(Ethoxycarbonyl)-S-4-[4-((R)-2-Hydroxy-1-methyl-ethylamino)-5-(3-hydroxyphenyl-ethynyl)-pyrimidin-2-ylamino]-phenyl)-S-methyl-sulfoximide;

(RS)-N-(Ethoxycarbonyl)-S-4-[4-((R)-2-Hydroxy-1-methyl-ethylamino)-5-(pyridin-2-ylethynyl)-pyrimidin-2-ylamino]-phenyl)-S-methyl-sulfoximide;

(RS)-N-(Ethoxycarbonyl)-S-4-[4-((R)-2-Hydroxy-1-methyl-ethylamino)-5-(3-methyl-3H-imidazol-4-yl-ethynyl)-pyrimidin-2-ylamino]-phenyl)-S-methyl-sulfoximide;

(RS)-S-(3-[5-(4-Ethoxy-phenyl-ethynyl)-4-((R)-2-hydroxy-1-methyl-ethylamino)-pyrimidin-2-ylamino]-phenyl)-N-(isopropylcarbamoyl)-S-methylsulfoximide;

(RS)-S-(4-[5-(4-Ethoxy-phenyl-ethynyl)-4-((R)-2-hydroxy-1-methyl-ethylamino)-pyrimidin-2-ylamino]-phenyl)-S-methylsulfoximide;

(RS)-S-(3-[5-(4-methoxy-phenylethynyl)-pyrimidin-2-ylamino]-phenyl)-S-methylsulfoximide; and (RS)-S-(3-[5-(3-hydroxy-phenylethynyl)-pyrimidin-2-ylamino]-phenyl)-S-methylsulfoximide.

7. A method of preparing a compound of general formula (I) according to claim 1, said method comprising the step of allowing an intermediate compound of general formula 6:

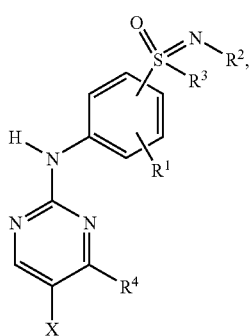

in which X stands for Br or I and $R^1$, $R^2$, $R^3$ and $R^4$ are as defined in claim 1, to undergo a transition metal mediated coupling reaction with a compound of formula 5:

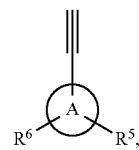

in which A, $R^5$ and $R^6$ are as defined in clam 1, thereby providing a compound of general formula I:

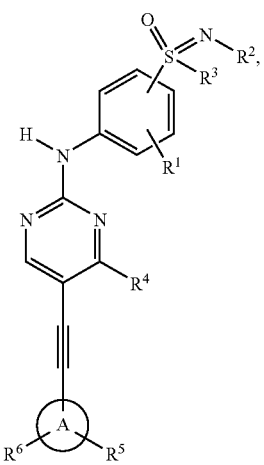

in which $R^1$, $R^2$, $R^3$, $R^4$, $R^5$, $R^6$, and A are defined as in claim 1.

8. A method of preparing a compound of general formula (I) according to claim 1, said method comprising the step of allowing an intermediate compound of general formula 6:

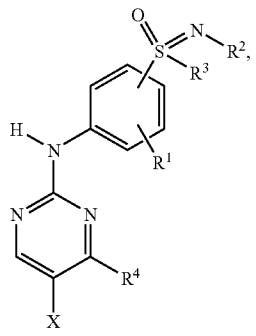

in which X stands for Br or I and $R^1$, $R^2$, $R^3$ and $R^4$ are as defined in claim 1, to undergo a transition metal mediated coupling reaction with a compound of formula 5':

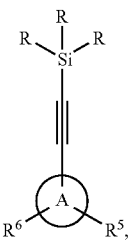

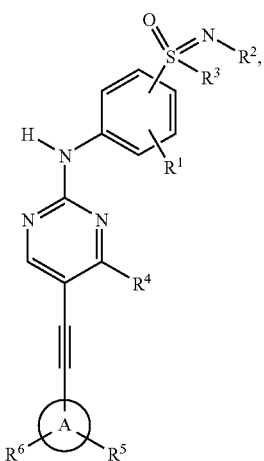

in which R stands for C1-C6 alkyl, preferably methyl, and A, $R^5$ and $R^6$ are as defined in claim 1,
thereby providing a compound of general formula I:

I in which $R^1$, $R^2$, $R^3$, $R^4$, $R^5$, $R^6$, and A are as defined in claim 1.

9. A method of preparing a compound of general formula (Ib) according to claim 1, said method comprising the step of allowing a compound of general formula Ia:

Ia

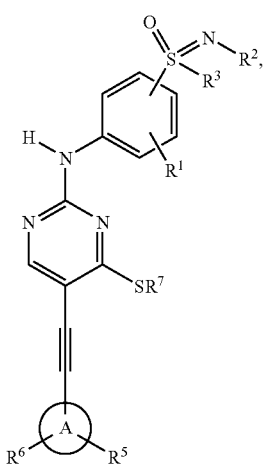

in which $R^1$, $R^2$, $R^3$, $R^5$, $R^6$, $R^7$ and A are as defined in claim 1, to react in the presence of an oxidizing agent, such as meta-chloroperbenzoic acid, with an amine of general formula 9:

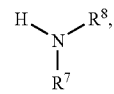

9 in which $R^7$ and $R^8$ are as defined in claim 1,
thereby providing a compound of general formula Ib:

Ib

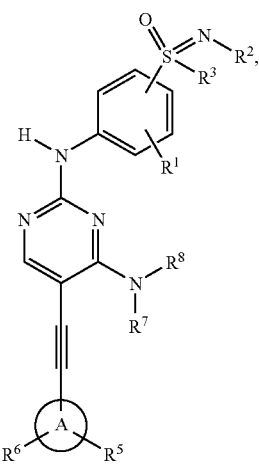

in which $R^1$, $R^2$, $R^3$, $R^5$, $R^6$, $R^7$, $R^8$ and A are as defined in claim 1.

10. A pharmaceutical composition which comprises a compound of general formula (I) according to claim 1, or a pharmaceutically acceptable salt or a tautomer of said compound, and a pharmaceutically acceptable diluent or carrier.

11. A method of treating a tumor and/or metastases thereof comprising administering an effective amount of a compound of general formula (I) according to claim 1.

12. The method according to claim 11, wherein said tumor and/or metastases thereof is a breast, colon, renal, ovarian, prostate, head, neck, pancreas, GI tract, thyroid, lung or brain tumor, melanoma, or metastases thereof.

13. A method of treating a disease selected from chronic myelogeneous leukaemia, acute myelogenous leukaemia, acute lymphatic leukaemia, acute lymphocytic leukaemia, chronic lymphocytic leukaemia, chronic lymphatic leukaemia, and other myeloid precursor hyperplasias comprising administering an effective amount of a compound of general formula (I) according to claim 1.

14. The compound according to claim 1 selected from the group consisting of:
(RS)-N-{3-[(4-{[(R)-2-hydroxy-1-methyl-ethylamino}-2-{[4-(S-methylsulfonimidoyl)phenyl]amino}pyrimidin-5-yl)ethynyl]phenyl}methanesulfonamide;
(RS)-S-4-[4-ethylamino-5-(1H-indazol-4-ylethynyl)-pyrimidin-2-ylamino]-phenyl)-S-methylsulfoximide;
(RS)-S-4-[5-(1H-indazol-4-ylethynyl)-4-methylamino-pyrimidin-2-ylamino]-phenyl)-S-methylsulfoximide;
3-[(4-[(R)-2-hydroxy-1-methyl-ethylamino]-2-{[(RS)-4-(S-methylsulfonimidoyl)phenyl]amino}pyrimidin-5-yl)ethynyl]-N-methylbenzamide;
N-{3-[(4-[(R)-2-hydroxy-1-methyl-ethyamino]-2-{[4-(S-methylsulfonimidoyl)phenyl]amino}pyrimidin-5-yl)ethynyl]-4-methylphenyl}methanesulfonamide;

3-[(4-[(R)-2-hydroxy-1-methyl-ethylamino]-2-{[4-(S-methylsulfonimidoyl)phenyl]amino}pyrimidin-5-yl)ethynyl]-N,4-dimethylbenzamide; and
(RS)-S-(4-[4-((R)-2-Hydroxy-1-methyl-ethylamino)-5-(3-hydroxy-pyrid-4-yl-ethynyl)-pyrimidin-2-ylamino]-phenyl)-S-methylsulfoximide.
15. The compound according to claim 1 selected from the group consisting of:
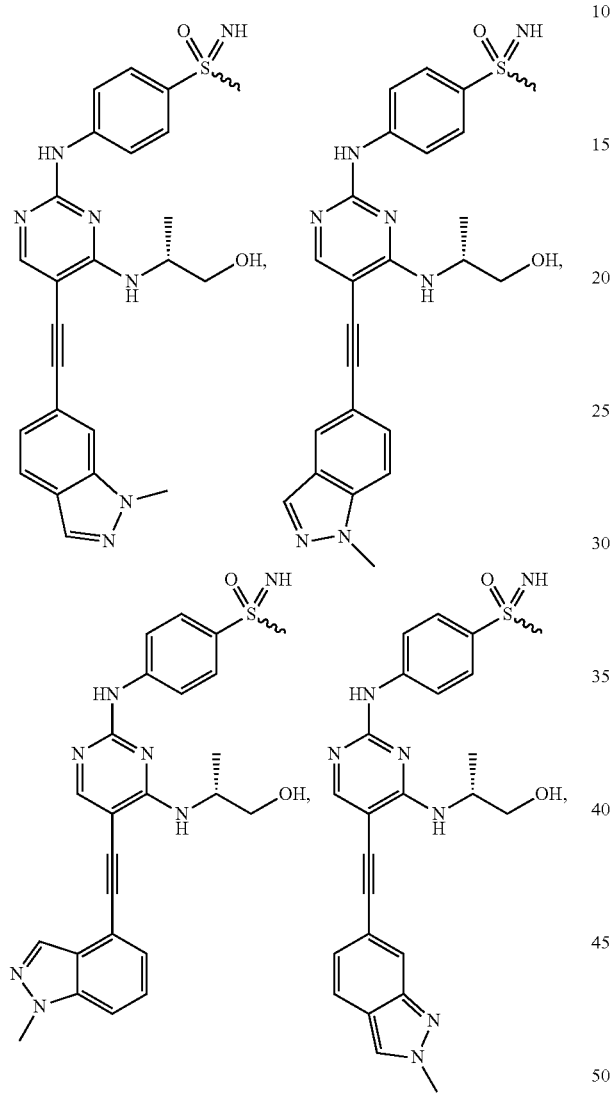
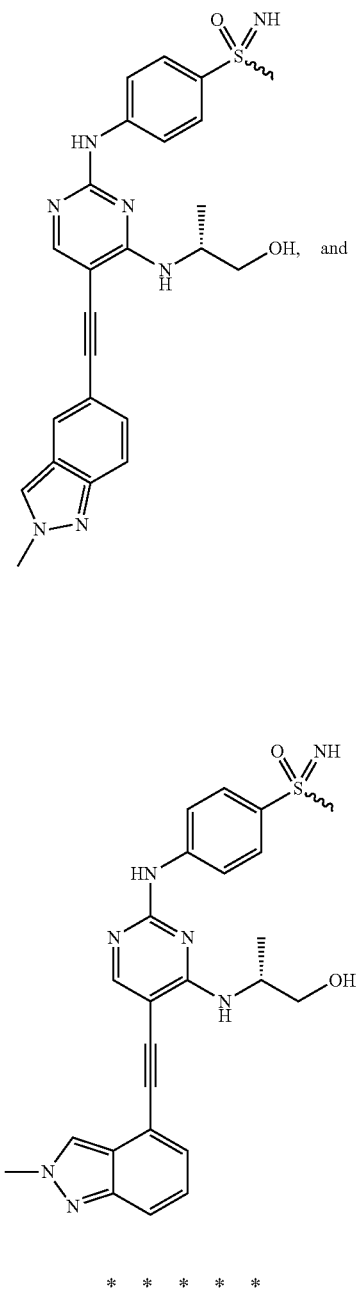
* * * * *